(12) United States Patent
Slassi et al.

(10) Patent No.: US 11,597,738 B2
(45) Date of Patent: Mar. 7, 2023

(54) PSILOCIN DERIVATIVES AS SEROTONERGIC PSYCHEDELIC AGENTS FOR THE TREATMENT OF CNS DISORDERS

(71) Applicant: Mindset Pharma Inc., Toronto (CA)

(72) Inventors: Abdelmalik Slassi, Mississauga (CA); Joseph Araujo, Grimsby (CA)

(73) Assignee: MINDSET PHARMA INC., Toronto (CA)

( * ) Notice: Subject to any disclaimer, the term of this patent is extended or adjusted under 35 U.S.C. 154(b) by 0 days.

(21) Appl. No.: 17/743,718

(22) Filed: May 13, 2022

(65) Prior Publication Data

US 2022/0289774 A1 Sep. 15, 2022

Related U.S. Application Data

(60) Division of application No. 17/387,845, filed on Jul. 28, 2021, now Pat. No. 11,427,604, which is a continuation of application No. PCT/CA2021/050123, filed on Feb. 4, 2021.

(60) Provisional application No. 62/969,934, filed on Feb. 4, 2020.

(51) Int. Cl.
C07D 209/16 (2006.01)
C07F 9/572 (2006.01)
C07D 401/14 (2006.01)
C07D 403/06 (2006.01)

(52) U.S. Cl.
CPC .......... *C07F 9/5728* (2013.01); *C07D 209/16* (2013.01); *C07D 401/14* (2013.01); *C07D 403/06* (2013.01); *C07B 2200/05* (2013.01)

(58) Field of Classification Search
CPC .................................................. C07D 209/16
See application file for complete search history.

(56) References Cited

U.S. PATENT DOCUMENTS

| | | | |
|---|---|---|---|
| 3,075,992 A | 1/1963 | Hofmann | |
| 7,429,575 B2 | 9/2008 | Yu et al. | |
| 7,572,776 B2 | 8/2009 | Yu et al. | |
| 7,776,844 B2 | 8/2010 | Yu et al. | |
| 11,000,534 B1 | 5/2021 | Sippy | |
| 11,242,318 B2 | 2/2022 | Nivorozhkin et al. | |
| 11,324,762 B2 | 5/2022 | Sippy | |
| 2021/0363104 A1 | 11/2021 | Nivorozhkin et al. | |
| 2021/0403425 A1 | 12/2021 | Bryson | |
| 2022/0110955 A1 | 4/2022 | Sippy | |
| 2022/0110956 A1 | 4/2022 | Sippy | |

FOREIGN PATENT DOCUMENTS

| | | | |
|---|---|---|---|
| CA | 2934061 A1 | 6/2015 | |
| CA | 3078765 A1 | 4/2019 | |
| WO | 2006047032 A2 | 5/2006 | |
| WO | 2009007421 A1 | 1/2009 | |
| WO | 2010012396 A1 | 2/2010 | |
| WO | 2010012397 A1 | 2/2010 | |
| WO | 2011019738 A1 | 2/2011 | |
| WO | 2016205304 A1 | 12/2016 | |
| WO | 2019073379 A1 | 4/2019 | |
| WO | 2019081764 A1 | 5/2019 | |
| WO | 2020041329 A1 | 2/2020 | |
| WO | 2020157569 A1 | 8/2020 | |
| WO | 2020181194 A1 | 9/2020 | |
| WO | 2021089873 A1 | 5/2021 | |
| WO | 2020245133 A2 | 6/2021 | |
| WO | 2021108911 A1 | 6/2021 | |
| WO | 2021116503 A2 | 6/2021 | |
| WO | 2021158888 A1 | 8/2021 | |
| WO | 2022000091 A1 | 1/2022 | |

OTHER PUBLICATIONS

Reexam U.S. Appl. No. 90/014,868, filed Sep. 23, 2021 Lenham Pharmaceuticals, Inc.*
International Search Report and Written Opinion of WO2021155470 dated Apr. 8, 2021.
Cerletti, A et al, "Pharmacologic studies on the structure-activity relationship of hydroxyindole alkylamines". Advances in Pharmacology, 1968, vol. 6, pp. 233-246.
Bartolucci, S et al, "Observations concerning the synthesis of tryptamine homologues and branched tryptamine derivatives via the borrowing hydrogen process: synthesis of psilocin, bufotenin, and serotonin", Tetrahedron, 2016, vol. 72, pp. 2233-2238.
Grandberg, I I et al, "Indoles. I. A new Method for the Synthesis of 2-Substituted Tryptamines". Chemistry of Heterocyclic Compounds, 1971, vol. 4, pp. 632-633.

(Continued)

*Primary Examiner* — Rebecca L Anderson
(74) *Attorney, Agent, or Firm* — Bereskin & Parr LLP/S.E.N.C.R.L., s.r.l.; Patricia Folkins

(57) ABSTRACT

The present application relates to psilocin derivatives of Formula (I), to processes for their preparation, to compositions comprising them and to their use in activation of a serotonin receptor in a cell, as well as to treating diseases, disorders or conditions by activation of a serotonin receptor in a cell.

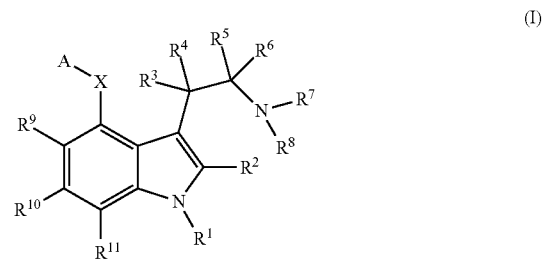

(I)

29 Claims, 1 Drawing Sheet

(56) References Cited

OTHER PUBLICATIONS

Palangsuntikul, R et al, "Holographic quantitative structure-activity relationships of tryptamine derivatives at NMDA, 5HT1A and 5HT2A receptors". Molecules, 2013, vol. 18, pp. 8799-8811.
International Search Report and Written Opinion of WO2021155468 dated Apr. 27, 2021.
Sard et al.,"SAR of philocybin analogs:Discovery of a selective 5-HTC2 agonist", Bioorganic & Medicinal Chemistry letters 15, 2005, pp. 4555-4559.
F. Hasler et al. "Determination of psilocin and 4-hydroxyindole 3 acetic acid in plasma by HPLC-ECD and pharmacokinetic profiles of oral and intravenous psilocybin in man", Pharmaceutica Acta Helvetiae, 1997 vol. 72, pp. 175-184.
Kristen C. Buteau "Deuterated Drugs: Unexpectedly Nonobvious?", 10 J. High Tech. Law 22. 2009, pp. 22-74.
CAS RN 1794789-72-2, Dec. 18, 2017 https://pubchem.ncbi.nlm.nih.gov/substance/348845401#section=2D-Structure.
CAS RN 1794759-76-4, Mar. 27, 2018 https://pubchem.ncbi.nlm.nih.gov/substance/355123594.
CAS RN 1246817-39-9, Mar. 27, 2018 https://pubchem.ncbi.nlm.nih.gov/substance/355191611.
CAS RN 1246816-52-3, Mar. 27, 2018 https://pubchem.ncbi.nlm.nih.gov/substance/355191609.
CAS RN 1216523-27-1, Mar. 27, 2018 https://pubchem.ncbi.nlm.nih.gov/substance/355123592.
Klein et al.,"Investigation of the Structure—Activity Relationships of Psilocybin Analogues", ACS Pharmacology & Translational Science 4(2) 533-542, 2020.
Sherwood et al., "Synthesis and Biological Evaulation of Tryptamines Found in Hallucinogenic Mushrooms: Norbaeocystin, Baeocystin, Norpsilocin, and Aeruginascin", Journal of Natural Products, 83(2), 461-467, 2020.
Raisanen, Martti, et al., "Deuterium Labelling of Tyrptamine, Serotonin and their N-Methylated Metabolites Using Solvent Exchange Reactions", Acta Chemica Scandinavica B 33, 1979, pp. 11-14.
Reexam U.S. Appl. No. 90/014,868, filed Sep. 23, 2021 Lennham Pharmaceuticals, Inc.
CAS RN 1435934-64-7 https://www.ceriliant.com/shopOnline/Item.Details.aspx?itemno=4973ed15-d59e-4a94-8cd4-ed45a8b6f249&item=P-099 dated Jun. 7, 2013.
CAS RN 1397192-09-4 dated Sep. 27, 2012.
CAS RN 1286546-49-3 dated Apr. 27, 2011.
CAS RN 1246819-43-1 dated Oct. 22, 2010.

* cited by examiner

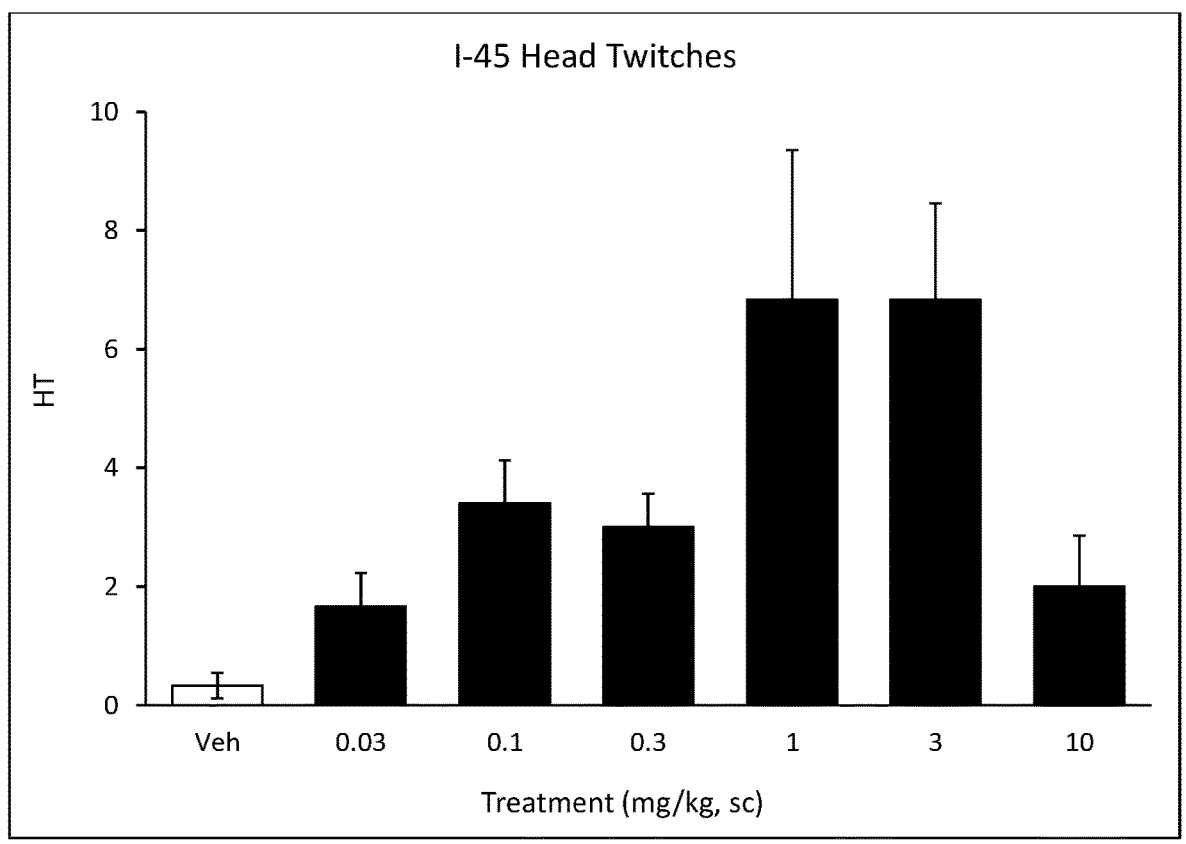

PSILOCIN DERIVATIVES AS SEROTONERGIC PSYCHEDELIC AGENTS FOR THE TREATMENT OF CNS DISORDERS

RELATED APPLICATIONS

The present application is a divisional of co-pending U.S. patent application Ser. No. 17/387,845 filed on Jul. 28, 2021, which is a continuation of co-pending International patent application no. PCT/CA2021/050123 filed Feb. 4, 2021 which claims the benefit of priority of U.S. provisional patent application No. 62/969,934 filed on Feb. 4, 2020 the contents of each of which are incorporated herein by reference in their entirety.

FIELD

The application relates to novel psilocin derivatives of Formula (I) for the treatment of different conditions that are treated by activation of serotonin receptor, for example, mental illnesses and other neurological diseases, disorders and conditions, in the fields of psychiatry, neurobiology and pharmacotherapy. The present application further comprises methods for making the compounds of Formula (I) and corresponding intermediates.

BACKGROUND OF THE APPLICATION

Mental health disorders, or mental illness, refer to a wide range of disorders that include, but are not limited to, depressive disorders, anxiety and panic disorders, schizophrenia, eating disorders, substance misuse disorders, post-traumatic stress disorder, attention deficit/hyperactivity disorder and obsessive compulsive disorder. The severity of symptoms varies such that some individuals experience debilitating disease that precludes normal social function, while others suffer with intermittent repeated episodes across their lifespan. Although the presentation and diagnostic criteria among mental illness conditions are distinct in part, there are common endophenotypes of note across the diseases, and often comorbidities exist. Specifically, there exist phenotypic endophenotypes associated with alterations in mood, cognition and behavior. Interestingly, many of these endophenotypes extend to neurological conditions as well. For example, attentional deficits are reported in patients with attention deficit disorder, attention deficit hyperactivity disorder, eating disorders, substance use disorders, schizophrenia, depression, obsessive compulsive disorder, traumatic brain injury, Fragile X, Alzheimer's disease, Parkinson's disease and frontotemporal dementia.

Many mental health disorders, as well as neurological disorders, are impacted by alterations, dysfunction, degeneration, and/or damage to the brain's serotonergic system, which may explain, in part, common endophenotypes and comorbidities among neuropsychiatric and neurological diseases. Many therapeutic agents that modulate serotonergic function are commercially available, including serotonin reuptake inhibitors, selective serotonin reuptake inhibitors, antidepressants, monoamine oxidase inhibitors, and, while primarily developed for depressive disorders, many of these therapeutics are used across multiple medical indications including, but not limited to, depression in Alzheimer's disease and other neurodegenerative disease, chronic pain, existential pain, bipolar disorder, obsessive compulsive disorder, anxiety disorders and smoking cessation. However, in many cases, the marketed drugs show limited benefit compared to placebo, can take six weeks to work and for some patients, and are associated with several side effects including trouble sleeping, drowsiness, fatigue, weakness, changes in blood pressure, memory problems, digestive problems, weight gain and sexual problems.

The field of psychedelic neuroscience has witnessed a recent renaissance following decades of restricted research due to their legal status. Psychedelics are one of the oldest classes of psychopharmacological agents known to man and cannot be fully understood without reference to various fields of research, including anthropology, ethnopharmacology, psychiatry, psychology, sociology, and others. Psychedelics (serotonergic hallucinogens) are powerful psychoactive substances that alter perception and mood and affect numerous cognitive processes. They are generally considered physiologically safe and do not lead to dependence or addiction. Their origin predates written history, and they were employed by early cultures in many sociocultural and ritual contexts. After the virtually contemporaneous discovery of (5R,8R)-(+)-lysergic acid-N,N-diethylamide (LSD) and the identification of serotonin in the brain, early research focused intensively on the possibility that LSD and other psychedelics had a serotonergic basis for their action. Today there is a consensus that psychedelics are agonists or partial agonists at brain serotonin 5-hydroxytryptamine 2A (5-HT2A) receptors, with particular importance on those expressed on apical dendrites of neocortical pyramidal cells in layer V, but also may bind with lower affinity to other receptors such as the sigma-1 receptor. Several useful rodent models have been developed over the years to help unravel the neurochemical correlates of serotonin 5-HT2A receptor activation in the brain, and a variety of imaging techniques have been employed to identify key brain areas that are directly affected by psychedelics.

Psychedelics have both rapid onset and persisting effects long after their acute effects, which includes changes in mood and brain function. Long lasting effects may result from their unique receptor affinities, which affect neurotransmission via neuromodulatory systems that serve to modulate brain activity, i.e., neuroplasticity, and promote cell survival, are neuroprotective, and modulate brain neuroimmune systems. The mechanisms which lead to these long-term neuromodulatory changes are linked to epigenetic modifications, gene expression changes and modulation of pre- and post-synaptic receptor densities. These, previously under-researched, psychedelic drugs may potentially provide the next-generation of neurotherapeutics, where treatment resistant psychiatric and neurological diseases, e.g., depression, post-traumatic stress disorder, dementia and addiction, may become treatable with attenuated pharmacological risk profiles.

Although there is a general perception that psychedelic drugs are dangerous, from a physiologic safety standpoint, they are one of the safest known classes of CNS drugs. They do not cause addiction, and no overdose deaths have occurred after ingestion of typical doses of classical psychotic agents, such as LSD, psilocybin, or mescaline (Scheme 1). Preliminary data show that psychedelic administration in humans results in a unique profile of effects and potential adverse reactions that need to be appropriately addressed to maximize safety. The primary safety concerns are largely psychologic, rather than physiologic, in nature. Somatic effects vary but are relatively insignificant, even at doses that elicit powerful psychologic effects. Psilocybin, when administered in a controlled setting, has frequently been reported to cause transient, delayed headache, with incidence, duration, and severity increased in a dose-related manner [Johnson et al., Drug Alcohol Depend (2012) 123 (1-3):132-140]. It has been found that repeated administration of psychedelics leads to a very rapid development of tolerance known as tachyphylaxis, a phenomenon believed to be mediated, in part, by 5-HT2A receptors. In fact, several studies have shown that rapid tolerance to psychedelics correlates with downregulation of 5-HT2A receptors. For example, daily LSD administration selectively decreased 5-HT2 receptor density in the rat brain [Buckholtz et al., Eur. J. Pharmacol. 1990, 109:421-425. 1985; Buckholtz et al., Life Sci. 1985, 42:2439-2445].

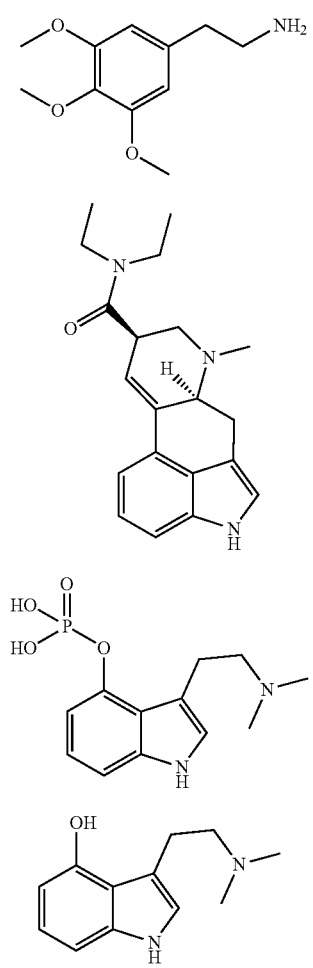

Scheme 1: Chemical Structures of or Mescaline (i), LSD (ii), Psilocybin (iii) and Psilocin (iv)

Classic psychedelics and dissociative psychedelics are known to have rapid onset antidepressant and anti-addictive effects, unlike any currently available treatment. Randomized clinical control studies have confirmed antidepressant and anxiolytic effects of classic psychedelics in humans. Ketamine also has well established antidepressant and anti-addictive effects in humans mainly through its action as an NMDA antagonist. Ibogaine has demonstrated potent anti-addictive potential in pre-clinical studies and is in the early stages of clinical trials to determine efficacy in robust human studies [Barsuglia et al., Prog Brain Res, 2018, 242:121-158; Corkery, Prog Brain Res, 2018, 242:217-257].

Psilocybin (4-phosphoryloxy-N,N-dimethyltrypatmine (iii, Scheme 1) has the chemical formula $C_{12}H_{17}N_2O_4P$. It is a tryptamine and is one of the major psychoactive constituents in mushrooms of the psilocybe species. It was first isolated from psilocybe mushrooms by Hofmann in 1957, and later synthesized by him in 1958 [Passie et al. Addict Biol., 2002, 7(4):357-364], and was used in psychiatric and psychological research and in psychotherapy during the early to mid-1960s up until its controlled drug scheduling in 1970 in the US, and up until the 1980s in Germany [Passie 2005; Passie et al. Addict Biol., 2002, 7(4):357-364]. Research into the effects of psilocybin resumed in the mid-1990s, and it is currently the preferred compound for use in studies of the effects of serotonergic hallucinogens [Carter et al. J. Cogn. Neurosci., 2005 17(10):1497-1508; Gouzoulis-Mayfrank et al. Neuropsychopharmacology 1999, 20(6):565-581; Hasler et al, Psychopharmacology (Berl) 2004, 172(2):145-156], likely because it has a shorter duration of action and suffers from less notoriety than LSD. Like other members of this class, psilocybin induces sometimes profound changes in perception, cognition and emotion, including emotional lability.

In humans as well as other mammals, psilocybin is transformed into the active metabolite psilocin, or 4-hydroxy-N,N-dimethyltryptamine (iv, Scheme 1). It is likely that psilocin partially or wholly produces most of the subjective and physiological effects of psilocybin in humans and non-human animals. Recently, human psilocybin research confirms the 5HT2A activity of psilocybin and psilocin, and provides some support for indirect effects on dopamine through 5HT2A activity and possible activity at other serotonin receptors. In fact, the most consistent finding for involvement of other receptors in the actions of psychedelics is the 5-HT1A receptor. That is particularly true for tryptamines and LSD, which generally have significant affinity and functional potency at this receptor. It is known that 5-HT1A receptors are colocalized with 5-HT2A receptors on cortical pyramidal cells [Martin-Ruiz et al. J Neurosci. 2001, 21(24):9856-986], where the two receptor types have opposing functional effects [Araneda et al. Neuroscience 1991, 40(2):399-412].

Although the exact role of the 5-HT2A receptor, and other 5-HT2 receptor family members, is not well understood with respect to the amygdala, it is evident that the 5-HT2A receptor plays an important role in emotional responses and is an important target to be considered in the actions of 5-HT2A agonist psychedelics. In fact, a majority of known 5HT2A agonists produce hallucinogenic effects in humans, and rodents generalize from one 5HT2A agonist to others, as between psilocybin and LSD [Aghajanian et al., Eur J Pharmacol., 1999, 367(2-3):197-206; Nichols at al., J Neurochem., 2004, 90(3):576-584]. Psilocybin has a stronger affinity for the human 5HT2A receptor than for the rat receptor and it has a lower K(i) for both 5HT2A and 5HT2C receptors than LSD. Moreover, results from a series of drug-discrimination studies in rats found that 5HT2A antagonists, and not 5HT1A antagonists, prevented rats from recognizing psilocybin [Winter et al., Pharmacol Biochem Behav., 2007, 87(4):472-480]. Daily doses of LSD and psilocybin reduce 5HT2 receptor density in rat brain.

Clinical studies in the 1960s and 1970s showed that psilocybin produces an altered state of consciousness with subjective symptoms such as "marked alterations in perception, mood, and thought, changes in experience of time, space, and self." Psilocybin was used in experimental research for the understanding of etiopathogenesis of selective mental disorders and showed psychotherapeutic potential [Rucker et al., Psychopharmacol., 2016, 30(12):1220-1229]. Psilocybin became increasingly popular as a hallucinogenic recreational drug and was eventually classed as a Schedule I controlled drug in 1970. Fear of psychedelic abuse led to a significant reduction in research being done in this area until the 1990s when human research of psilocybin was revived when conditions for safe administration were established [Johnson et al., Psychopharmacol., 2008, 22(6): 603-620]. Today, psilocybin is one of the most widely used psychedelics in human studies due to its relative safety, moderately long active duration, and good absorption in subjects. There remains strong research and therapeutic potential for psilocybin as recent studies have shown varying degrees of success in neurotic disorders, alcoholism, depression in terminally ill cancer patients, obsessive compulsive disorder, addiction, anxiety, post-traumatic stress disorder and even cluster headaches. It could also be useful as a psychosis model for the development of new treatments for psychotic disorders. [Dubovyk and Monahan-Vaughn, ACS Chem. Neurosci. (2018), 9(9):2241-2251].

Recent developments in the field have occurred in clinical research, where several double-blind placebo-controlled phase 2 studies of psilocybin-assisted psychotherapy in patients with treatment resistant, major depressive disorder and cancer-related psychosocial distress have demonstrated unprecedented positive relief of anxiety and depression. Two recent small pilot studies of psilocybin assisted psychotherapy also have shown positive benefit in treating both alcohol and nicotine addiction. Recently, blood oxygen level-dependent functional magnetic resonance imaging and magnetoencephalography have been employed for in vivo brain imaging in humans after administration of a psychedelic, and results indicate that intravenously administered psilocybin and LSD produce decreases in oscillatory power in areas of the brain's default mode network [Nichols D E. Pharmacol Rev., 2016, 68(2):264-355].

Preliminary studies using positron emission tomography (PET) showed that psilocybin ingestion (15 or 20 mg orally) increased absolute metabolic rate of glucose in frontal, and to a lesser extent in other, cortical regions as well as in striatal and limbic subcortical structures in healthy participants, suggesting that some of the key behavioral effects of psilocybin involve the frontal cortex [Gouzoulis-Mayfrank et al., Neuropsychopharmacology, 1999, 20(6):565-581; Vollenweider et al., Brain Res. Bull. 2001, 56(5):495-507]. Although 5HT2A agonism is widely recognized as the primary action of classic psychedelic agents, psilocybin has lesser affinity for a wide range of other pre- and post-synaptic serotonin and dopamine receptors, as well as the serotonin reuptake transporter [Tyls et al., Eur. Neuropsychopharmacol., 2014, 24(3):342-356]. Psilocybin activates 5HT1A receptors, which may contribute to antidepressant/anti-anxiety effects.

Depression and anxiety are two of the most common psychiatric disorders worldwide. Depression is a multifaceted condition characterized by episodes of mood disturbances alongside other symptoms such as anhedonia, psychomotor complaints, feelings of guilt, attentional deficits and suicidal tendencies, all of which can range in severity. According to the World Health Organization, the discovery of mainstream antidepressants has largely revolutionized the management of depression, yet up to 60% of patients remain inadequately treated. This is often due to the drugs' delayed therapeutic effect (generally 6 weeks from treatment onset), side effects leading to non-compliance, or inherent non-responsiveness to them. Similarly, anxiety disorders are a collective of etiologically complex disorders characterized by intense psychosocial distress and other symptoms depending on the subtype. Anxiety associated with life-threatening disease is the only anxiety subtype that has been studied in terms of psychedelic-assisted therapy. This form of anxiety affects up to 40% of individuals diagnosed with life-threatening diseases like cancer. It manifests as apprehension regarding future danger or misfortune accompanied by feelings of dysphoria or somatic symptoms of tension, and often coexists with depression. It is associated with decreased quality of life, reduced treatment adherence, prolonged hospitalization, increased disability, and hopelessness, which overall contribute to decreased survival rates. Pharmacological and psychosocial interventions are commonly used to manage this type of anxiety, but their efficacy is mixed and limited such that they often fail to provide satisfactory emotional relief. Recent interest into the use of psychedelic-assisted therapy may represent a promising alternative for patients with depression and anxiety that are ineffectively managed by conventional methods.

Generally, the psychedelic treatment model consists of administering the orally-active drug to induce a mystical experience lasting 4-9 h depending on the psychedelic [Halberstadt, Behav Brain Res., 2015, 277:99-120; Nichols, Pharmacol Rev., 2016, 68(2): 264-355]. This enables participants to work through and integrate difficult feelings and situations, leading to enduring anti-depressant and anxiolytic effects. Classical psychedelics like psilocybin and LSD are being studied as potential candidates. In one study with classical psychedelics for the treatment of depression and anxiety associated with life-threatening disease, it was found that, in a supportive setting, psilocybin, and LSD consistently produced significant and sustained anti-depressant and anxiolytic effects.

Psychedelic treatment is generally well-tolerated with no persisting adverse effects. Regarding their mechanisms of action, they mediate their main therapeutic effects biochemically via serotonin receptor agonism, and psychologically by generating meaningful psycho-spiritual experiences that contribute to mental flexibility. Given the limited success rates of current treatments for anxiety and mood disorders, and considering the high morbidity associated with these conditions, there is potential for psychedelics to provide symptom relief in patients inadequately managed by conventional methods.

Further emerging clinical research and evidence suggest psychedelic-assisted therapy, also shows potential as an alternative treatment for refractory substance use disorders and mental health conditions, and thus may be an important tool in a crisis where existing approaches have yielded limited success. A recent systematic review of clinical trials published over the last 25 years summarizes some of the anti-depressive, anxiolytic, and anti-addictive effects of classic psychedelics. Among these, are encouraging findings from a meta-analysis of randomized controlled trials of LSD therapy and a recent pilot study of psilocybin-assisted therapy for treating alcohol use disorder [dos Santos et al., Ther Adv Psychopharmacol., 2016, 6(3):193-213]. Similarly encouraging, are findings from a recent pilot study of psilocybin-assisted therapy for tobacco use disorder, demonstrating abstinence rates of 80% at six months follow-up and 67% at 12 months follow-up [Johnson et al., J Drug Alcohol Abuse, 2017, 43(1):55-60; Johnson et al., Psychopharmacol. 2014, 28(11):983-992], such rates are considerably higher than any documented in the tobacco cessation literature. Notably, mystical-type experiences generated from the psilocybin sessions were significantly correlated with positive treatment outcomes. These results coincide with bourgeoning evidence from recent clinical trials lending support to the effectiveness of psilocybin-assisted therapy for treatment-resistant depression and end-of-life anxiety [Carhart-Harris et al. Neuropsychopharmacology, 2017, 42(11):2105-2113]. Research on the potential benefits of psychedelic-assisted therapy for opioid use disorder (OUD) is beginning to emerge, and accumulating evidence supports a need to advance this line of investigation. Available evidence from earlier randomized clinical trials suggests a promising role for treating OUD: higher rates of abstinence were observed among participants receiving high dose LSD and ketamine-assisted therapies for heroin addiction compared to controls at long-term follow-ups. Recently, a large United States population study among 44,000 individuals found that psychedelic use was associated with 40% reduced risk of opioid abuse and 27% reduced risk of opioid dependence in the following year, as defined by DSM-IV criteria [Pisano et al., J Psychopharmacol., 2017, 31(5):606-613]. Similarly, a protective moderating effect of psychedelic use was found on the relationship between prescription opioid use and suicide risk among marginalized women [Argento et al., J Psychopharmacol., 2018, 32(12):1385-1391]. Despite the promise of these preliminary findings with classical psychedelic agents, further research is warranted to determine what it may contribute to the opioid crisis response given their potential toxicity. Meanwhile, growing evidence on the safety and efficacy of psilocybin for the treatment of mental and substance use disorders should help to motivate further clinical investigation into its use as a novel intervention for OUD.

Regular doses of psychedelics also ameliorate sleep disturbances, which are highly prevalent in depressive patients with more than 80% of them having complaints of poor sleep quality. The sleep symptoms are often unresolved by first-line treatment and are associated with a greater risk of relapse and recurrence. Interestingly, sleep problems often appear before other depression symptoms, and subjective sleep quality worsens before the onset of an episode in recurrent depression. Brain areas showing increased functional connectivity with poor sleep scores and higher depressive symptomatology scores included prefrontal and limbic areas, areas involved in the processing of emotions. Sleep disruption in healthy participants has demonstrated that sleep is indeed involved in mood, emotion evaluation processes and brain reactivity to emotional stimuli. An increase in negative mood and a mood-independent mislabeling of neutral stimuli as negative was for example shown by one study while another demonstrated an amplified reactivity in limbic brain regions in response to both negative and positive stimuli. Two other studies assessing electroencephalographic (EEG) brain activity during sleep showed that psychedelics, such as LSD, positively affect sleep patterns. Moreover, it has been shown that partial or a full night of sleep deprivation can alleviate symptoms of depression suggested by resetting circadian rhythms via modification of clock gene expression. It further was suggested that a single dose of a psychedelic causes a reset of the biological clock underlying sleep/wake cycles and thereby enhances cognitive-emotional processes in depressed people but also improving feelings of well-being and enhances mood in healthy individuals [Kuypers, Medical Hypotheses, 2019, 125:21-24].

In a systematic meta-analysis of clinical trials from 1960-2018 researching the therapeutic use of psychedelic treatment in patients with serious or terminal illnesses and related psychiatric illness, it was found that psychedelic therapy (mostly with LSD) may improve cancer-related depression, anxiety, and fear of death. Four randomized controlled clinical trials were published between 2011 and 2016, mostly with psilocybin treatment, that demonstrated psychedelic-assisted treatment can produce rapid, robust, and sustained improvements in cancer-related psychological and existential distress. [Ross S, Int Rev Psychiatry, 2018, 30(4):317-330]. Thus, the use of psychedelics in the fields of oncology and palliative care is intriguing for several reasons. First, many patients facing cancer or other life-threatening illnesses experience significant existential distress related to loss of meaning or purpose in life, which can be associated with hopelessness, demoralization, powerlessness, perceived burdensomeness, and a desire for hastened death. Those features are also often at the core of clinically significant anxiety and depression, and they can substantially diminish quality of life in this patient population. The alleviation of those forms of suffering should be among the central aims of palliative care. Accordingly, several manualized psychotherapies for cancer-related existential distress have been developed in recent years, with an emphasis on dignity and meaning-making. However, there are currently no pharmacologic interventions for existential distress per se, and available pharmacologic treatments for depressive symptoms in patients with cancer have not demonstrated superiority over placebo. There remains a need for additional effective treatments for those conditions [Rosenbaum et al., Curr. Oncol., 2019, 26(4): 225-226].

Recently, there has been growing interest in a new dosing paradigm for psychedelics such as psilocybin and LSD referred to colloquially as microdosing. Under this paradigm, sub-perceptive doses of the serotonergic hallucinogens, approximately 10% or less of the full dose, are taken on a more consistent basis of once each day, every other day, or every three days, and so on. Not only is this dosing paradigm more consistent with current standards in pharmacological care, but may be particularly beneficial for certain conditions, such as Alzheimer's disease and other neurodegenerative diseases, attention deficit disorder, attention deficit hyperactivity disorder, and for certain patient populations such as elderly, juvenile and patients that are fearful of or opposed to psychedelic assisted therapy. Moreover, this approach may be particularly well suited for managing cognitive deficits and preventing neurodegeneration. For example, subpopulations of low attentive and low motivated rats demonstrate improved performance on 5 choice serial reaction time and progressive ratio tasks, respectively, following doses of psilocybin below the threshold for eliciting the classical wet dog shake behavioral response associated with hallucinogenic doses (Blumstock et al., WO 2020/157569 A1). Similarly, treatment of patients with hallucinogenic doses of 5HT2A agonists is associated with increased BDNF and activation of the mTOR pathway, which are thought to promote neuroplasticity and are hypothesized to serve as molecular targets for the treatment of dementias and other neurodegenerative disorders (Ly et al. Cell Rep., 2018, 23(11):3170-3182). Additionally, several groups have demonstrated that low, non-hallucinogenic and non-psychomimetic, doses of 5HT2A agonists also show similar neuroprotective and increased neuroplasticity effects (neuroplastogens) and reduced neuroinflammation, which could be beneficial in both neurodegenerative and neurodevelopmental diseases and chronic disorders (Manfredi et al., WO 2020/181194, Flanagan et al., Int. Rev. Psychiatry, 2018, 13:1-13; Nichols et al., 2016, Psychedelics as medicines; an emerging new paradigm). This repeated, lower, dose paradigm may extend the utility of these compounds to additional indications and may prove useful for wellness applications.

Psychosis is often referred to as an abnormal state of mind that is characterized by hallucinatory experiences, delusional thinking, and disordered thoughts. Moreover, this state is accompanied by impairments in social cognition, inappropriate emotional expressions, and bizarre behavior. Most often, psychosis develops as part of a psychiatric disorder, of which, it represents an integral part of schizophrenia. It corresponds to the most florid phase of the illness. The very first manifestation of psychosis in a patient is referred to as first-episode psychosis. It reflects a critical transitional stage toward the chronic establishment of the disease, that is presumably mediated by progressive structural and functional abnormalities seen in diagnosed patients. [ACS Chem. Neurosci., 2018, 9, 2241-2251]. Anecdotal evidence suggests that low, non-hallucinogenic, doses (microdosing) of psychedelics that are administered regularly can reduce symptoms of schizophrenia and psychosis.

SUMMARY OF THE APPLICATION

The present application includes a compound of Formula (I) or a pharmaceutically acceptable salt, solvate and/or prodrug thereof:

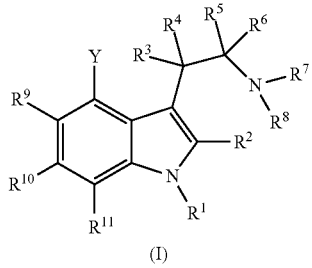

(I)

wherein $R^1$ is selected from hydrogen, $C_1$-$C_3$ alkyl, $C(O)R^{12}$, $CO_2R^{12}$, $C(O)N(R^{12})_2$, $S(O)R^{12}$ and $SO_2R^{12}$;

$R^3$, $R^4$, $R^5$ and $R^6$ are independently selected from hydrogen and $C_1$-$C_6$alkyl;

$R^7$ and $R^8$ are independently selected from hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$haloalkyl, substituted or unsubstituted $C_3$-$C_7$cycloalkyl, substituted or unsubstituted $C_3$-$C_7$heterocycloalkyl, substituted or unsubstituted aryl and substituted or unsubstituted heteroaryl, or $R^7$ and $R^8$ are taken together with the nitrogen atom therebetween to form a 3- to 7-membered heterocyclic ring optionally including 1 to 2 additional ring heteromoieties selected from O, S, S(O), $SO_2$, N and $NR^{13}$, wherein said $C_3$-$C_7$cycloalkyl and 3- to 7-membered heterocyclic ring are each further optionally substituted with a substituent selected from halogen, $CO_2R^{13}$, $C(O)N(R^{13})_2$, $SO_2R^{13}$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl and a 3- to 6-membered heterocyclic ring including 1 to 2 ring heteromoieties selected from O, S, N, S(O), $SO_2$ and $NR^{13}$;

$R^9$, $R^{10}$ and $R^{11}$ are independently selected from hydrogen, halogen, CN, $OR^{13}$, $N(R^{13})_2$, $SR^{13}$, $C_1$-$C_6$alkyl, $C_1$-$C_6$haloalkyl, $C_2$-$C_6$haloalkenyl, $CO_2R^{13}$, $C(O)N(R^{13})_2$, $SOR^{13}$, $SO_2R^{13}$, $C_2$-$C_6$alkenyl, $C_2$-$C_6$alkynyl, $C_2$-$C_6$haloalkynyl, $C_3$-$C_6$cycloalkyl and a 3- to 7-membered heterocyclic ring including 1 to 2 ring heteromoieties selected from O, S, S(O), $SO_2$, N and $NR^{13}$, wherein said $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl and 3- to 7-membered heterocyclic ring groups are optionally substituted by one or more substituents independently selected from CN, $OR^{13}$, $N(R^{13})_2$ and $SR^{13}$, and wherein said $C_3$-$C_6$cycloalkyl and 3- to 7-membered heterocyclic ring are each further optionally substituted with a substituent selected from halogen, $CO_2R^{13}$, $C(O)N(R^{13})_2$, $SO_2R^{13}$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl and a 3- to 6-membered heterocyclic ring including 1 to 2 ring heteromoieties selected from O, S, S(O), $SO_2$, N and $NR^{13}$;

Y is selected from halogen and X-A;

X is selected from O, $NR^{13}$, S, S(O) and $SO_2$;

A is selected from hydrogen, $C_1$-$C_{10}$alkyl, $C_2$-$C_{10}$alkenyl, $C_2$-$C_{10}$alkynyl, $C_3$-$C_6$cycloalkyl, $C_4$-$C_6$cycloalkenyl, heterocycloalkyl, aryl, heteroaryl, and $P(O)(OR^{12})_2$;

each $R^{12}$ is independently selected from hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$haloalkyl, substituted or unsubstituted $C_3$-$C_7$cycloalkyl, substituted or unsubstituted $C_3$-$C_7$heterocycloalkyl, substituted or unsubstituted aryl, substituted or unsubstituted heteroaryl, substituted or unsubstituted $C_1$-$C_6$alkylene$C_3$-$C_7$cycloalkyl, substituted or unsubstituted $C_1$-$C_6$alkylene$C_3$-$C_7$heterocycloalkyl, substituted or unsubstituted $C_1$-$C_6$alkylenearyl, and substituted or unsubstituted $C_1$-$C_6$alkyleneheteroaryl;

each $R^{13}$ is independently selected from hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, and a 3- to 7-membered heterocyclic ring including 1 to 2 ring heteromoieties selected from O, S, S(O), $SO_2$, N and $NR^{14}$, wherein said $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_7$cycloalkyl and 3- to 7-membered heterocyclic ring groups are optionally substituted by one or more substituents independently selected from CN, $OR^{14}$, $N(R^{14})_2$ and $SR^{14}$, and wherein said $C_3$-$C_7$cycloalkyl and 3- to 7-membered heterocyclic ring are each further optionally substituted with a substituent selected from halogen, $CO_2R^{14}$, $C(O)N(R^{14})_2$, $SO_2R^{14}$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl and a 3- to 6-membered heterocyclic ring including 1 to 2 ring heteromoieties selected from O, S, S(O), $SO_2$, N and $NR^{14}$, $R^{14}$ is selected from hydrogen, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$haloalkyl, substituted or unsubstituted $C_3$-$C_7$cycloalkyl, substituted or unsubstituted heterocycloalkyl, substituted or unsubstituted aryl and substituted or unsubstituted heteroaryl;

wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, the compounds of Formula (I) and pharmaceutically acceptable salts, solvates and/or prodrugs thereof, are isotopically enriched with deuterium. In some embodiments, one or more of A, X, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ comprises one or more deuterium or one or more of A, X, $R^1$, $R^2$, $R^3$, $R^4$, $R^5$, $R^6$, $R^7$ $R^8$, $R^9$, $R^{10}$, $R^{11}$, $R^{12}$, $R^{13}$ and $R^{14}$ is deuterium.

In a further embodiment, the compounds of the application are used as medicaments. Accordingly, the application also includes a compound of the application for use as a medicament.

The present application includes a method for activating a serotonin receptor in a cell, either in a biological sample or in a patient, comprising administering an effective amount of one or more compounds of the application to the cell.

The present application also includes a method of treating psychosis or psychotic symptoms comprising administering a therapeutically effective amount of one or more compounds of the application to a subject in need thereof.

The present application also includes a method of treating a mental illness comprising administering a therapeutically effective amount of one or more compounds of the application to a subject in need thereof.

The present application also includes a method of treating a CNS disease, disorder or condition and/or a neurological disease, disorder or condition comprising administering a therapeutically effective amount of one or more compounds of the application to a subject in need thereof.

The application additionally provides a process for the preparation of compounds of the application. General and specific processes are discussed in more detail below and set forth in the examples below.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1. is a graph showing the effect of various doses of exemplary compound of Formula I, I-45, on head-twitch response (HTR) in male C57BL6 mice. The mice were treated with compound I-45 (0.03-10 mg/kg, SC) by SC route (N=6 mice/dose), and the total number of head twitches were recorded over a 1 h period. Data is expressed as mean+SEM. The induction of head twitches elicited by 5-HT2A receptor agonists is believed to represent a behavioural proxy of their psychedelic effects.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "compound(s) of the application" or "compound(s) of the present application" and the like as used herein refers to a compound of Formula (I) and compounds of Formula (I-A) to (I-I) and pharmaceutically acceptable salts, solvates and/or prodrugs thereof.

The term "composition(s) of the application" or "composition(s) of the present application" and the like as used herein refers to a composition, such a pharmaceutical composition, comprising one or more compounds of the application.

The term "and/or" as used herein means that the listed items are present, or used, individually or in combination. In effect, this term means that "at least one of or "one or more" of the listed items is used or present. The term "and/or" with respect to pharmaceutically acceptable salts, solvates and/or prodrugs thereof means that the compounds of the application exist as individual salts, solvates and prodrugs, as well as a combination of, for example, a salt of a solvate of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers and/or steps and also exclude the presence of other unstated features, elements, components, groups, integers and/or steps.

The term "consisting essentially of", as used herein, is intended to specify the presence of the stated features, elements, components, groups, integers and/or steps as well as those that do not materially affect the basic and novel characteristic(s) of these features, elements, components, groups, integers and/or steps.

In embodiments comprising an "additional" or "second" component, such as an additional or second compound, the second component as used herein is chemically different from the other components or first component. A "third" component is different from the other, first and second components and further enumerated or "additional" components are similarly different.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical terms and abbreviations used by those skilled in the art. Nevertheless, definitions of selected terms are provided for clarity and consistency.

The term "solvate" as used herein means a compound, or a salt or prodrug of a compound, wherein molecules of a suitable solvent are incorporated in the crystal lattice. A suitable solvent is physiologically tolerable at the dosage administered.

The term "prodrug" as used herein means a compound, or salt of a compound, that, after administration, is converted into an active drug.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". Thus, for example, the term "$C_{1-6}$alkyl" (or "$C_1$-$C_6$alkyl") means an alkyl group having 1, 2, 3, 4, 5, or c carbon atoms and includes, for example, any of the hexyl alkyl and pentyl alkyl isomers as well as n-, iso-, sec- and ter-butyl, n- and iso-propyl, ethyl and methyl. As another example, "$C_4$alkyl" refers to n-, iso-, sec- and tert-butyl, n- and isopropyl, ethyl and methyl.

The term "alkenyl" whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms.

The term "cycloalkyl," as used herein, whether it is used alone or as part of another group, means a saturated carbocyclic group containing from 3 to 20 carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to carbocyclic groups containing at least one aromatic ring and contains either 6 to 20 carbon atoms.

The term "available", as in "available hydrogen atoms" or "available atoms" refers to atoms that would be known to a person skilled in the art to be capable of replacement by a substituent.

The term "heterocycloalkyl" as used herein, whether it is used alone or as part of another group, refers to cyclic groups containing at least one non-aromatic ring containing from 3 to 20 atoms in which one or more of the atoms are a heteromoiety selected from O, S, S(O), $SO_2$ and N and the remaining atoms are C. Heterocycloalkyl groups are either saturated or unsaturated (i.e. contain one or more double bonds). When a heterocycloalkyl group contains the prefix $C_{n1-n2}$ or "n1 to n2" this prefix indicates the number of carbon atoms in the corresponding carbocyclic group, in which one or more, suitably 1 to 5, of the ring atoms is replaced with a heteromoeity as selected from O, S, S(O), $SO_2$ and N and the remaining atoms are C. Heterocycloalkyl groups are optionally benzofused.

The term "heteroaryl" as used herein, whether it is used alone or as part of another group, refers to cyclic groups containing at least one heteroaromatic ring containing 5-20 atoms in which one or more of the atoms are a heteroatom selected from O, S and N and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heteroaryl groups are optionally benzofused.

All cyclic groups, including aryl, heteroaryl, heterocycloalkyl and cycloalkyl groups, contain one or more than one ring (i.e. are polycyclic). When a cyclic group contains more than one ring, the rings may be fused, bridged, spirofused or linked by a bond.

The term "benzofused" as used herein refers to a polycyclic group in which a benzene ring is fused with another ring.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "halogen" (or "halo") whether it is used alone or as part of another group, refers to a halogen atom and includes fluoro, chloro, bromo and iodo.

The term "haloalkyl" as used herein refers to an alkyl group as defined above in which one or more of the available hydrogen atoms have been replaced with a halogen. Thus, for example, "$C_{1-6}$haloalkyl" (or "$C_1$-$C_6$haloalkyl") refers to a $C_1$ to $C_6$ linear or branched alkyl group as defined above with one or more halogen substituents.

As used herein, the term "haloalkenyl" refers to an alkenyl group as defined above in which one or more of the available hydrogen atoms have been replaced with a halogen. Thus, for example, "$C_{1-6}$haloalkenyl" (or "$C_1$-$C_6$haloalkenyl") refers to a $C_1$ to $C_6$ linear or branched alkenyl group as defined above with one or more halogen substituents.

As used herein, the term "haloalkynyl" refers to an alkynyl group as defined above in which one or more of the available hydrogen atoms have been replaced with a halogen. Thus, for example, "$C_{1-6}$haloalkynyl" (or "$C_1$-$C_6$haloalkynyl") refers to a $C_1$ to $C_6$ linear or branched alkynyl group as defined above with one or more halogen substituents.

As used herein, the term "alkoxy" as used herein, alone or in combination, includes an alkyl group connected to an oxygen connecting atom.

As used herein, the term "one or more" item includes a single item selected from the list as well as mixtures of two or more items selected from the list.

The term "substituted" as used herein means, unless otherwise indicated, that the referenced group is substituted with one or more substituents independently selected from halogen, $CO_2H$, $CO_2CH_3$, $C(O)NH_2$, $C(O)N(CH_3)_2$, $C(O)NHCH_3$, $SO_2CH_3$, $SOCH_3$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl and a 3- to 6-membered heterocyclic ring including 1 to 2 ring heteromoieties selected from O, S, S(O), $SO_2$, N, NH and $NCH_3$.

The term "alternate isotope thereof" as used herein refers to an isotope of an element that is other than the isotope that is most abundant in nature.

In the compounds of general Formula (I) and pharmaceutically acceptable salts, solvates and/or prodrug thereof, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general Formula (I) and pharmaceutically acceptable salts, solvates and/or prodrug thereof. For example, different isotopic forms of hydrogen (H) include protium (1H), deuterium (2H) and tritium (3H). Protium is the predominant hydrogen isotope found in nature.

The term "all available atoms are optionally substituted with alternate isotope" as used herein means that available atoms are optionally substituted with an isotope of that atom of having the same atomic number, but an atomic mass or mass number different from the atomic mass or mass number predominantly found in nature.

The term "compound" refers to the compound and, in certain embodiments, to the extent they are stable, any hydrate or solvate thereof. A hydrate is the compound complexed with water and a solvate is the compound complexed with a solvent, which may be an organic solvent or an inorganic solvent. A "stable" compound is a compound that can be prepared and isolated and whose structure and properties remain or can be caused to remain essentially unchanged for a period of time sufficient to allow use of the compound for the purposes described herein (e.g., therapeutic administration to a subject). The compounds of the present application are limited to stable compounds embraced by general Formula (I), or pharmaceutically acceptable salts, solvates and/or prodrug thereof.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "subject" as used herein includes all members of the animal kingdom including mammals, and suitably refers to humans. Thus the methods of the present application are applicable to both human therapy and veterinary applications.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alliteratively comprise a series of administrations.

As used herein, the term "effective amount" or "therapeutically effective amount" means an amount of one or more compounds of the application that is effective, at dosages and for periods of time necessary to achieve the desired result. For example, in the context of treating a disease, disorder or condition mediated or treated by agonism or activation of serotonergic receptors and downstream second messengers, an effective amount is an amount that, for example, increases said activation compared to the activation without administration of the one or more compounds.

"Palliating" a disease, disorder or condition means that the extent and/or undesirable clinical manifestations of a disease, disorder or condition are lessened and/or time course of the progression is slowed or lengthened, as compared to not treating the disorder.

The term "administered" as used herein means administration of a therapeutically effective amount of one or more compounds or compositions of the application to a cell, tissue, organ or subject.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The "disease, disorder or condition" as used herein refers to a disease, disorder or condition treated or treatable by activation a serotonin receptor, for example $5-HT_{2A}$ and particularly using a serotonin receptor agonist, such as one or more compounds of the application herein described.

The term "treating a disease, disorder or condition by activation of a serotonin receptor" as used herein means that the disease, disorder or condition to be treated is affected by, modulated by and/or has some biological basis, either direct or indirect, that includes serotonergic activity, in particular increases in serotonergic activity. These diseases respond favourably when serotonergic activity associated with the disease, disorder or condition is agonized by one or more of the compounds or compositions of the application.

The term "activation" as used herein includes agonism, partial agonist and positive allosteric modulation of a serotonin receptor.

The term "5-HT$_{2A}$" as used herein mean the 5-HT$_{2A}$ receptor subtype of the 5-HT$_2$ serotonin receptor.

The term "therapeutic agent" as used herein refers to any drug or active agent that has a pharmacological effect when administered to a subject.

II. Compounds

The present application includes a compound of Formula (I) or a pharmaceutically acceptable salt, solvate and/or prodrug thereof:

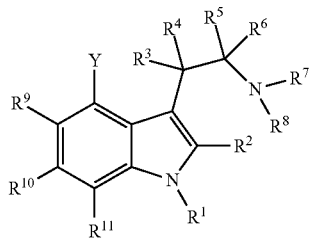

(I)

wherein R$^1$ is selected from hydrogen, C$_1$-C$_3$ alkyl, C(O) R$^{12}$, CO$_2$OR$^{12}$, C(O)N(R$^{12}$)$_2$, S(O)R$^{12}$ and SO$_2$R$^{12}$;

R$^3$, R$^4$, R$^5$ and R$^6$ are independently selected from hydrogen and C$_1$-C$_6$alkyl;

R$^7$ and R$^8$ are independently selected from hydrogen, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$haloalkyl, substituted or unsubstituted C$_3$-C$_7$cycloalkyl, substituted or unsubstituted C$_3$-C$_7$heterocycloalkyl, substituted or unsubstituted aryl and substituted or unsubstituted heteroaryl, or R$^7$ and R$^8$ are taken together with the nitrogen atom therebetween to form a 3- to 7-membered heterocyclic ring optionally including 1 to 2 additional ring heteromoieties selected from O, S, S(O), SO$_2$, N and NR$^{13}$, wherein said C$_3$-C$_7$cycloalkyl and 3- to 7-membered heterocyclic ring are each further optionally substituted with a substituent selected from halogen, CO$_2$R$^{13}$, C(O)N(R$^{13}$)$_2$, SO$_2$R$^{13}$, C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and a 3- to 6-membered heterocyclic ring including 1 to 2 ring heteromoieties selected from O, S, N, S(O), SO$_2$ and NR$^{13}$;

R$^9$, R$^{10}$ and R$^{11}$ are independently selected from hydrogen, halogen, CN, OR$^{13}$, N(R$^{13}$)$_2$, SR$^{13}$, C$_1$-C$_6$alkyl, C$_1$-C$_6$haloalkyl, C$_2$-C$_6$haloalkenyl, CO$_2$R$^{13}$, C(O)N(R$^{13}$)$_2$, SOR$^{13}$, SO$_2$R$^{13}$, C$_2$-C$_6$alkenyl, C$_2$-C$_6$alkynyl, C$_2$-C$_6$haloalkynyl, C$_3$-C$_7$cycloalkyl and a 3- to 7-membered heterocyclic ring including 1 to 2 ring heteromoieties selected from O, S, S(O), SO$_2$, N and NR$^{13}$, wherein said C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and 3- to 7-membered heterocyclic ring groups are optionally substituted by one or more substituents independently selected from CN, OR$^{13}$, N(R$^{13}$)$_2$ and SR$^{13}$, and wherein said C$_3$-C$_6$cycloalkyl and 3- to 7-membered heterocyclic ring are each further optionally substituted with a substituent selected from halogen, CO$_2$R$^{13}$, C(O)N(R$^{13}$)$_2$, SO$_2$R$^{13}$, C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and a 3- to 6-membered heterocyclic ring including 1 to 2 ring heteromoieties selected from O, S, S(O), SO$_2$, N and NR$^{13}$;

Y is selected from halogen and X-A;
X is selected from O, NR$^{13}$, S, S(O) and SO$_2$;
A is selected from hydrogen, C$_1$-C$_{10}$alkyl, C$_2$-C$_{10}$alkenyl, C$_2$-C$_{10}$alkynyl, C$_3$-C$_6$cycloalkyl, C$_4$-C$_6$cycloalkenyl, heterocycloalkyl, aryl, heteroaryl and P(O)(OR$^{12}$)$_2$;

each R$^{12}$ is independently selected from hydrogen, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$haloalkyl, substituted or unsubstituted C$_3$-C$_7$cycloalkyl, substituted or unsubstituted C$_3$-C$_7$heterocycloalkyl, substituted or unsubstituted aryl, substituted or unsubstituted heteroaryl, substituted or unsubstituted C$_1$-C$_6$alkyleneC$_3$-C$_7$cycloalkyl, substituted or unsubstituted C$_1$-C$_6$alkyleneC$_3$-C$_7$heterocycloalkyl, substituted or unsubstituted C$_1$-C$_6$alkylenearyl, and substituted or unsubstituted C$_1$-C$_6$alkyleneheteroaryl;

each R$^{13}$ is independently selected from hydrogen, C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, and a 3- to 7-membered heterocyclic ring including 1 to 2 ring heteromoieties selected from O, S, S(O), SO$_2$, N and NR$^{14}$, wherein said C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and 3- to 7-membered heterocyclic ring groups are optionally substituted by one or more substituents independently selected from CN, OR$^{14}$, N(R$^{14}$)$_2$ and SR$^{14}$, and wherein said C$_3$-C$_6$cycloalkyl and 3- to 7-membered heterocyclic ring are each further optionally substituted with a substituent selected from halogen, CO$_2$R$^{14}$, C(O)N(R$^{14}$)$_2$, SO$_2$R$^{14}$, C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and a 3- to 6-membered heterocyclic ring including 1 to 2 ring heteromoieties selected from O, S, S(O), SO$_2$, N and NR$^{14}$, R$^{14}$ is selected from hydrogen, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$haloalkyl, substituted or unsubstituted C$_3$-C$_7$cycloalkyl, substituted or unsubstituted heterocycloalkyl, substituted or unsubstituted aryl and substituted or unsubstituted heteroaryl;

wherein at least one of R$^3$, R$^4$, R$^5$ and R$^6$ is deuterium or at least one of R$^3$, R$^4$, R$^5$ and R$^6$ comprises deuterium, and wherein all available hydrogen atoms are optionally substituted with a halogen atom and/or all available atoms are optionally substituted with an alternate isotope thereof.

The present application includes a compound of Formula (I) or a pharmaceutically acceptable salt, solvate and/or prodrug thereof:

Formula (I)

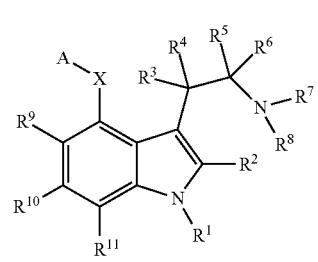

wherein:

$R^1$ is selected from the group consisting of hydrogen, $C_1$-$C_3$ alkyl, —$(CH_2)P(O)(OR^{12})$; $CO(R^{12})$, $COO(R^{12})$, $C(O)N(R^{12})_2$, $SO(R^{12})$ and $SO_2(R^{12})$;

$R^2$ to $R^6$ are independently selected from the group consisting of hydrogen and lower alkyl;

$R^7$ and $R^8$ are independently selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, $R^7$ and $R^8$ may be taken together with the atoms to which they are attached form a 3- or 7-membered heterocyclic ring including 1 to 2 ring members selected from the group consisting of O, S, $SO_2$, N, and $N(R^{13})$ wherein said $C_3$-$C_7$ cycloalkyl and 3 to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, SR6, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl;

$R^9$, $R^{10}$ and, $R^{11}$ are independently selected from the group consisting of hydrogen, halogen, CN, $OR^{13}$, $N(R^{13})_2$, $SR^{13}$, $C_1$-$C_6$ alkyl, $C_1$-$C_6$ haloalkyl, $C_1$-$C_6$ alkyl substituted by $OR^{13}$, $C_1$-$C_6$ alkyl substituted by $SR^{13}$, $C_1$-$C_6$ alkyl substituted by $N(R^{13})_2$, $C_2$-$C_6$ haloalkyl, $COOR^{13}$, $C(O)N(R^{13})_2$, $SO_2R^{13}$, $COOR^{13}$, $C(O)N(R^{13})_2$, $SO_2R^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 67-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl;

X is selected from O, $NR^{13}$, S, SO and $SO_2$;

wherein $R^{12}$ is selected from hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

$R^{13}$ is selected from the group consisting of hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C_1$-$C_6$ alkyl substituted by $OR^{13}$, $C_1$-$C_6$ alkyl substituted by $SR^{13}$, $C_1$-$C_6$ alkyl substituted by $N(HR^{13})$, $N(R^{13})_2$, $C_2$-$C_6$ haloalkyl, $COOR^{13}$, $C(O)N(R^{13})_2$, $SO_2R^{13}$, $COOR^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl; and A is selected from hydrogen, alkyl, alkenyl, alkynyl, cycloalkyl, cycloalkenyl, heterocycloalkyl, heterocycloalkenyl, heterocycloalkynyl, heterocycloalkynyl aryl, heteroaryl, $C_0$-$C_1$ $P(O)(OR^{12})_2$, $CO(Q')$, $COO(Q')$, $C(O)N(Q')_2$, $SO(Q')$, $SO_2(Q')$, wherein Q' is selected from hydrogen, $C_1$-$C_{20}$ alkyl, $C_1$-$C_{20}$ haloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_{20}$ alkyl, $C_2$-$C_{20}$ haloalkyl, $C_2$-$C_6$ alkenyl, $C_2$-$C_{20}$ haloalkenyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$cycloalkyl and 3- to 7-membered heterocyclic ring are each further optionally substituted with a member of the group consisting of $C_1$-$C_3$ alkyl and $C_1$-$C_3$ haloalkyl; and wherein $R^{12}$ and $R^{13}$ are independently defined as above.

In some embodiments, when, in the compounds of Formula I, all available hydrogen atoms in a group are optionally replaced with a halogen atom, the halogen atom is F, Cl or Br. In some embodiments, when all available hydrogen atoms in a group are optionally replaced with a halogen atom, the halogen atom is F or Br. In some embodiments, when all available hydrogen atoms in a group are optionally replaced with a halogen atom, the halogen atom is F.

Therefore, in some embodiments, all available hydrogen atoms are optionally substituted with a fluorine, chlorine or bromine atom and/or all available atoms are optionally substituted with an alternate isotope thereof. In some embodiments, all available hydrogen atoms are optionally substituted with a halogen or bromine atom and/or all available atoms are optionally substituted with an alternate isotope thereof. In some embodiments, all available hydrogen atoms are optionally substituted with a halogen or chlorine atom and/or all available atoms are optionally substituted with an alternate isotope thereof. In some embodiments, all available hydrogen atoms are optionally substituted with a halogen atom and/or all available atoms are optionally substituted with an alternate isotope thereof. In some embodiments, all available hydrogen atoms are optionally substituted with a halogen atom and/or all available hydrogen atoms are optionally substituted with deuterium. In some embodiments, all available hydrogen atoms are optionally substituted with a fluorine atom and/or all available atoms are optionally substituted with deuterium. In some embodiments, all available atoms are optionally substituted with deuterium.

In some embodiments, all available hydrogen atoms are optionally substituted with an alternate isotope thereof. In some embodiments, the alternate isotope of hydrogen is deuterium. Accordingly, in some embodiments, the compounds of the application are isotopically enriched with deuterium. In some embodiments, one or more of A, X, $R^1$, $R^2$, $R^3$, $R^4$, $R^5$, $R^6$, $R^7$ $R^8$, $R^9$, $R^{10}$, $R^{11}$, $R^{12}$, $R^{13}$ and $R^{14}$ comprises one or more deuterium or one or more of A, X, $R^1$, $R^2$, $R^3$, $R^4$, $R^5$, $R^6$, $R^7$ $R^8$, $R^9$, $R^{10}$, $R^{11}$, $R^{12}$, $R^{13}$ and $R^{14}$ is deuterium.

In some embodiments, $R^1$ is selected from hydrogen, $C_1$-$C_3$alkyl, $C(O)R^{12}$, $CO_2R^{12}$, $C(O)N(R^{12})_2$, $S(O)R^{12}$ and $SO_2R^{12}$; wherein all available hydrogen atoms are optionally substituted with a halogen and/or all available atoms are optionally substituted with an alternate isotope thereof. In some embodiments, $R^1$ is selected from $S(O)R^{12}$ and $SO_2R^{12}$, wherein all available hydrogen atoms are optionally substituted with a halogen and/or all available atoms are optionally substituted with an alternate isotope thereof. In some embodiments, $R^1$ is selected from hydrogen, $C_1$-$C_3$alkyl, $C(O)R^{12}$, $CO_2R^{12}$ and $C(O)N(R^{12})_2$, wherein all available hydrogen atoms are optionally substituted with a halogen and/or all available atoms are optionally substituted with an alternate isotope thereof. In some embodiments, $R^1$ is selected from hydrogen, $C_1$-$C_3$alkyl, $C(O)R^{12}$ and $CO_2R^{12}$, wherein all available hydrogen atoms are optionally substituted with a halogen and/or all available atoms are optionally substituted with an alternate isotope thereof. In some embodiments, $R^1$ is selected from hydrogen, $CH_3$, $CH_2CH_3$, and $CH(CH_3)_2$, wherein all available hydrogen atoms are optionally substituted with a halogen and/or all available atoms are optionally substituted with an alternate isotope thereof. In some embodiments, $R^1$ is selected from hydrogen, deuterium, Br, F, $CH_3$, $CF_3$, $CD_3$, $CH_2CH_3$, $CD_2CD_3$, $CF_2CF_3$, $CH(CH_3)_2$, $CD(CD_3)_2$, $CF(CF_3)_2$, $C(CD_3)_3$, $C(CF_3)_3$, and $C(CH_3)_2$. In some embodiments, $R^1$ is selected from hydrogen, deuterium, $CH_3$, $CF_3$ and $CD_3$. In some embodiments, $R^1$ is hydrogen.

In some embodiments, $R^2$ is selected from hydrogen and $C_1$-$C_4$alkyl, wherein all available hydrogen atoms are optionally substituted with a halogen atom and/or all available atoms are optionally substituted with an alternate isotope thereof. In some embodiments, $R^2$ is selected from hydrogen, $CH_3$, $CH_2CH_3$, $CH(CH_3)_2$ and $C(CH_3)_3$, wherein all available hydrogen atoms are optionally substituted with a halogen atom and/or all available atoms are optionally substituted with an alternate isotope thereof. In some embodiments, $R^2$ is selected from hydrogen, $CH_3$, $CH_2CH_3$, $CH(CH_3)_2$ and $C(CH_3)_3$, wherein all available hydrogen atoms are optionally substituted with a halogen atom and/or all available atoms are optionally substituted with deuterium. In some embodiments, $R^2$ is selected from hydrogen and deuterium, F, Br, $CH_3$, $CF_3$, $CD_3$, $CH_2CH_3$, $CD_2CD_3$, $CF_2CF_3$, $CH(CH_3)_2$, $CD(CD_3)_2$, $CF(CF_3)_2$, $C(CD_3)_3$, $C(CF_3)_3$, and $C(CH_3)_3$. In some embodiments, $R^2$ is selected from hydrogen and deuterium. In some embodiments, $R^2$ is hydrogen.

In some embodiments, $R^3$, $R^4$, $R^5$ and $R^6$ are independently selected from hydrogen and $C_1$-$C_4$alkyl, wherein at least one of $R^3$, $R^4$, $R^5$ and $R^6$ is deuterium or at least one of $R^3$, $R^4$, $R^5$ and $R^6$ comprises deuterium and wherein all available hydrogen atoms are optionally substituted with a halogen atom and/or all available atoms are optionally substituted with an alternate isotope thereof. In some embodiments, $R^3$, $R^4$, $R^5$ and $R^6$ are independently selected from hydrogen, $CH_3$, $CH_2CH_3$, $CH(CH_3)_2$ and $C(CH_3)_3$, wherein all available hydrogen atoms are optionally substituted with a halogen atom and/or all available atoms are optionally substituted with an alternate isotope thereof and wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, $CH_3$, $CH_2CH_3$, $CH(CH_3)_2$ and $C(CH_3)_3$, wherein all available hydrogen atoms are optionally substituted with a halogen atom and/or all available hydrogen atoms are optionally substituted with deuterium and wherein at least one of $R^3$, $R^4$, $R^5$ and $R^6$ is deuterium or at least one of $R^3$, $R^4$, $R^5$ and $R^6$ comprises deuterium. In some embodiments, at least one of $R^3$ and $R^4$ or $R^5$ and $R^6$ is deuterium or at least one of $R^3$ and $R^4$ or $R^5$ and $R^6$ comprises deuterium. In some embodiments, $R^3$, $R^4$, $R^5$ and $R^6$ are independently selected from hydrogen, deuterium, F, Br, $CH_3$, $CD_2H$, $CDH_2$, $CD_3$, $CH_2CH_3$, $CH_2CH_2D$, $CH_2CD_2H$ and $CD_2CD_3$, wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, deuterium, F, $CH_3$, $CD_2H$, $CDH_2$ and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, deuterium, F, $CH_3$ and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, deuterium, $CH_3$ and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, at least one of $R^3$, $R^4$, $R^5$ and $R^6$ is F, and wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, deuterium and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, at least one of $R^3$ and $R^4$ or $R^5$ and $R^6$ is $CD_3$. In some embodiments, $R^3$ and $R^4$ are both $CD_3$, or $R^5$ and $R^6$ are both $CD_3$. In some embodiments, $R^3$, $R^4$, $R^5$ and $R^6$ are all $CD_3$. In some embodiments, at least one of $R^3$ and $R^4$ or $R^5$ and $R^6$ is deuterium. In some embodiments, $R^3$ and $R^4$ are both deuterium, or $R^5$ and $R^6$ are both deuterium. In some embodiments, $R^3$, $R^4$, $R^5$ and $R^6$ are all deuterium.

In some embodiments, $R^7$ and $R^8$ are independently selected from hydrogen, substituted or unsubstituted $C_1$-$C_4$alkyl, substituted or unsubstituted $C_2$-$C_6$alkenyl, substituted or unsubstituted $C_2$-$C_6$alkynyl, substituted or unsubstituted $C_1$-$C_4$haloalkyl, substituted or unsubstituted $C_3$-$C_7$cycloalkyl, substituted or unsubstituted heterocycloalkyl, substituted or unsubstituted aryl and substituted or unsubstituted heteroaryl, wherein all available hydrogen atoms are optionally substituted with a halogen atom and/or all available atoms are optionally substituted with an alternate isotope thereof.

In some embodiments, the $C_3$-$C_7$cycloalkyl in $R^7$ and $R^8$ is independently selected from cyclopropyl, cyclobutyl, cyclopentyl and cyclohexyl, wherein all available hydrogen atoms are optionally substituted with a halogen atom and/or all available atoms are optionally substituted with an alternate isotope thereof.

In some embodiments, the heterocycloalkyl in $R^7$ and $R^8$ is, independently, a saturated or unsaturated heterocycle. In some embodiments heterocycloalkyl in $R^7$ and $R^8$ is, independently, a saturated or unsaturated bridged bicyclic heterocycle. In some embodiments, the saturated or unsaturated bridged bicyclic heterocycle is independently selected from azabicyclohexanyl, diazabicycloheptanyl, oxobicyclohexanyl, oxobicycloheptanyl and oxobicycloheptanenyl, wherein all available hydrogen atoms are optionally substituted with a halogen atom and/or all available atoms are optionally substituted with an alternate isotope thereof.

In some embodiments, the heterocycloalkyl in $R^7$ and $R^8$ independently, a saturated or unsaturated heterocycle. In some embodiments, heterocycloalkyl in $R^7$ and $R^8$ is, independently, a saturated or unsaturated bridged bicyclic heterocycle. In some embodiments, the saturated or unsaturated bridged bicyclic heterocycle is independently, selected from azabicyclohexanyl, diazabicycloheptanyl, oxobicyclohexanyl, oxobicycloheptanyl and oxobicycloheptanenyl, wherein all available hydrogen atoms are optionally substituted with a halogen atom and/or all available atoms are optionally substituted with an alternate isotope thereof.

In some embodiments, the heterocycloalkyl in $R^7$ and $R^8$ independently selected from aziridinyl, oxiranyl, thiiranyl, oxaxiridinyl, dioxiranyl, azetidinyl, oxetanyl, theitanyl, diazetidinyl, dioxetanyl, dithietanyl, tetrahydrofuranyl, tetrahydrothiophenyl, pyrrolidinyl, imidazolidinyl, pyrazolidinyl, isoxthiolidinyl, thiazolidinyl, isothiazolidinyl, dioxolanyl, dithiolanyl, piperidinyl, triazolyl, furazanyl, oxadiazolyl, thiadiazolyl, dioxazolyl, dithiazolyl, tetrazolyl, oxatetrazolyl, tetrahydropyranyl, diazinanyl (e.g. piperazinyl), morpholinyl, thiomorpholinyl, dioxanyl, dithianyl, azepanyl, oxepanyl, thiepanyl and diazepanyl, wherein all available hydrogen atoms are optionally substituted with a halogen atom and/or all available atoms are optionally substituted with an alternate isotope thereof.

In some embodiments, the heteroaryl in $R^7$ and $R^8$ is independently selected from, azepinyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl, wherein all available hydrogen atoms are optionally substituted with a halogen atom and/or all available atoms are optionally substituted with an alternate isotope thereof.

In some embodiments, $R^7$ and $R^8$ are independently selected from hydrogen, $C_1$-$C_4$alkyl and $C_2$-$C_6$alkenyl, wherein all available hydrogen atoms are optionally substituted with a halogen atom and/or all available atoms are optionally substituted with an alternate isotope thereof. In some embodiments, $R^7$ and $R^8$ are independently selected from hydrogen and $C_1$-$C_4$alkyl, wherein all available hydrogen atoms are optionally substituted with a halogen atom and/or all available atoms are optionally substituted with an alternate isotope thereof. In some embodiments, $R^7$ and $R^8$ are independently from hydrogen and $C_1$-$C_4$alkyl, wherein all available hydrogen atoms are optionally substituted with a halogen atom and/or all available hydrogens atoms are optionally substituted with deuterium. In some embodiments, $R^7$ and $R^8$ are independently selected from hydrogen, deuterium, F, Br, $CH_3$, $CF_3$, $CD_2H$, $CDH_2$, $CD_3$, $CH_2CH_3$, $CF_2CF_3$, and $CD_2CD_3$. In some embodiments, $R^7$ and $R^8$ are independently selected from hydrogen, deuterium, $CH_3$, $CD_2H$, $CDH_2$, $CD_3$, $CH_2CH_3$ and $CD_2CD_3$. In some embodiments, $R^7$ and $R^8$ are independently selected from hydrogen, deuterium, $CH_3$, $CD_3$, $CH_2CH_3$ and $CD_2CD_3$. In some embodiments, $R^7$ and $R^8$ are independently selected from $CH_3$, $CD_3$, $CH_2CH_3$ and $CD_2CD_3$. In some embodiments, $R^7$ and $R^3$ are both $CH_3$, $CD_3$, $CH_2CH_3$ or $CD_2CD_3$. In some embodiments, $R^7$ and $R^8$ are both $CH_3$. In some embodiments, $R^7$ and $R^8$ are both CDs. In some embodiments, $R^7$ and $R^8$ are both $CH_2CH_3$. In some embodiments, $R^7$ and $R^8$ are both $CD_2CD_3$.

In some embodiments, $R^7$ and $R^8$ are taken together with the nitrogen atom therebetween to form a 3- to 7-membered heterocyclic ring optionally including 1 to 2 additional ring heteromoieties selected from O, S, S(O), $SO_2$, N and $NR^{13}$, wherein all available hydrogen atoms are optionally substituted with a halogen atom and/or all available atoms are optionally substituted with an alternate isotope thereof. In some embodiments, $R^7$ and $R^8$ are taken together with the nitrogen atom therebetween to form a 4- to 7-membered heterocyclic ring optionally including 1 to 2 additional ring heteromoieties selected from O, S, S(O), $SO_2$, N and $NR^{13}$, wherein all available hydrogen atoms are optionally substituted with a halogen atom and/or all available atoms are optionally substituted with an alternate isotope thereof. In some embodiments, $R^7$ and $R^8$ may be taken together with the nitrogen atom therebetween to form azetidinyl, diazetidinyl, pyrrolidinyl, imidazolidinyl, pyrazolidinyl, thiazolidinyl, isothiozolidinyl, piperidinyl, diazinanyl (e.g. piperazinyl), morpholinyl or azepanyl ring, wherein all available hydrogen atoms are optionally substituted with a halogen atom and/or all available atoms are optionally substituted with an alternate isotope thereof. In some embodiments, $R^7$ and $R^8$ are taken together with the nitrogen atom therebetween to form pyrrolidinyl, piperidinyl or diazinanyl, wherein all available hydrogen atoms are optionally substituted with a halogen atom and/or all available atoms are optionally substituted with an alternate isotope thereof. In some embodiments, $R^7$ and $R^8$ are taken together with the nitrogen atom therebetween to form pyrrolidinyl, piperidinyl or diazinanyl, wherein all available hydrogen atoms are optionally substituted with a halogen atom and/or all available hydrogens are optionally substituted with deuterium. In some embodiments, $R^7$ and $R^8$ are taken together with the nitrogen atom therebetween to form pyrrolidinyl, piperidinyl or diazinanyl, wherein all available hydrogens are optionally substituted with deuterium.

When $R^7$ and $R^8$ are substituted, in some embodiments, the substituents are independently selected from one or more of Br, Cl, F, $CO_2H$, $CO_2CH_3$, $C(O)NH_2$, $C(O)N(CH_3)_2$, $C(O)NHCH_3$, $SO_2CH_3$, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl, $C_2$-$C_6$fluoroalkynyl, $C_3$-$C_6$cycloalkyl and a 3- to 6-membered heterocyclic ring including 1 to 2 ring heteromoieties selected from O, S, S(O), $SO_2$, N, NH and $NCH_3$. In some embodiments, the substituents on $R^7$ and $R^8$ are independently selected from one to three of Br, Cl, F, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl and $C_2$-$C_6$fluoroalkynyl. In some embodiments, the substituents on $R^7$ and $R^8$ are independently selected from one or two of Br, Cl, F, $CH_3$ and $CF_3$.

In some embodiments, $R^9$, $R^{10}$ and $R^{11}$ are independently selected from hydrogen, halogen, CN, $OR^{13}$, $N(R^{13})_2$, $SR^{13}$, $C_1$-$C_4$alkyl, $C_1$-$C_4$haloalkyl, $C_2$-$C_6$haloalkenyl, $CO_2R^{13}$, C(O)N(R$^{13}$)$_2$, S(O)R$^{13}$, SO$_2$R$^{13}$, C$_2$-C$_6$alkenyl, C$_2$-C$_6$alkynyl, C$_2$-C$_6$haloalkynyl, C$_3$-C$_7$cycloalkyl and a 3- to 7-membered heterocyclic ring including 1 to 2 ring heteromoieties selected from O, S, S(O), SO$_2$, N and NR$^{13}$, wherein said C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_7$cycloalkyl and 3- to 7-membered heterocyclic ring groups are optionally substituted by one or more substituents independently selected from CN, OR$^{13}$, N(R$^{13}$)$_2$ and SR$^{13}$ and wherein said C$_3$-C$_7$cycloalkyl and 3- to 7-membered heterocyclic ring are each further optionally substituted with a substituent selected from halogen, CO$_2$R$^{13}$, C(O)N(R$^{13}$)$_2$, SO$_2$R$^{13}$, C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl and a 3- to 6-membered heterocyclic ring including 1 to 2 ring heteromoieties selected from O, S, S(O), SO$_2$, N and NR$^{13}$; wherein all available hydrogen atoms are optionally substituted with a halogen atom and/or all available atoms are optionally substituted with an alternate isotope thereof.

In some embodiments, R$^9$, R$^{10}$ and R$^{11}$ are independently selected from hydrogen, halogen, CN, OR$^{13}$, N(R$^{13}$)$_2$, SR$^{13}$, C$_1$-C$_4$alkyl, C$_1$-C$_4$haloalkyl, C$_2$-C$_6$haloalkenyl, CO$_2$R$^{13}$, C(O)N(R$^{13}$)$_2$, S(O)R$^{13}$, SO$_2$R$^{13}$, C$_2$-C$_6$alkenyl, C$_2$-C$_6$alkynyl and C$_2$-C$_6$haloalkynyl, wherein said C$_1$-C$_4$alkyl, C$_1$-C$_4$haloalkyl, C$_2$-C$_6$alkenyl, C$_2$-C$_6$haloalkenyl, C$_2$-C$_6$alkynyl and C$_2$-C$_6$haloalkynyl groups are optionally substituted by one or more substituents independently selected from CN, OR$^{13}$, N(R$^{13}$)$_2$ and SR$^{13}$, and wherein all available hydrogen atoms are optionally substituted with a halogen atom and/or all available atoms are optionally substituted with an alternate isotope thereof. In some embodiments, R$^9$, R$^{10}$ and R$^{11}$ are independently selected from hydrogen, F, Cl, Br, CN, OR$^{13}$, N(R$^{13}$)$_2$, SR$^{13}$, C$_1$-C$_4$alkyl, C$_1$-C$_4$haloalkyl, C$_2$-C$_6$haloalkenyl, CO$_2$R$^{13}$, C(O)N(R$^{13}$)$_2$, S(O)R$^{13}$, SO$_2$R$^{13}$, C$_2$-C$_6$alkenyl, C$_2$-C$_6$alkynyl and C$_2$-C$_6$haloalkynyl, wherein said C$_1$-C$_4$alkyl, C$_1$-C$_4$haloalkyl, C$_2$-C$_6$alkenyl, C$_2$-C$_6$haloalkenyl, C$_2$-C$_6$alkynyl and C$_2$-C$_6$haloalkynyl groups are optionally substituted by one to three substituents independently selected from CN, OR$^{13}$, N(R$^{13}$)$_2$ and SR$^{13}$, wherein all available hydrogen atoms are optionally substituted with a halogen atom and/or all available atoms are optionally substituted with an alternate isotope thereof. In some embodiments, R$^9$, R$^{10}$ and R$^{11}$ are independently selected from hydrogen, F, Cl, Br, CN, OR$^{13}$, N(R$^{13}$)$_2$, SR$^{13}$, CH$_3$, CH$_2$CH$_3$, CH(CH$_3$)$_2$, C(CH$_3$)$_3$, C$_1$-C$_4$haloalkyl, C$_2$-C$_6$haloalkenyl, CO$_2$R$^{13}$, S(O)R$^{13}$, SO$_2$R$^{13}$, C(O)N(R$^{13}$)$_2$, C$_2$-C$_6$alkenyl and C$_2$-C$_6$alkynyl, wherein said C$_1$-C$_4$alkyl, C$_1$-C$_4$haloalkyl, C$_2$-C$_6$alkenyl, C$_2$-C$_6$haloalkenyl and C$_2$-C$_6$alkynyl groups are optionally substituted by one or two substituents independently selected from CN, OR$^{13}$, N(R$^{13}$)$_2$ and SR$^{13}$, wherein all available hydrogen atoms are optionally substituted with a halogen atom and/or all available atoms are optionally substituted with an alternate isotope thereof. In some embodiments, R$^9$, R$^{10}$ and R$^{11}$ are independently selected from hydrogen, F, Cl, Br, CN, OR$^{13}$, N(R$^{13}$)$_2$, SR$^{13}$, CH$_3$, CH$_2$CH$_3$, CH(CH$_3$)$_2$, C(CH$_3$)$_3$, C$_1$-C$_4$haloalkyl, C$_2$-C$_6$haloalkenyl, CO$_2$R$^{13}$, S(O)R$^{13}$, SO$_2$R$^{13}$ and C$_2$-C$_6$alkenyl, wherein all available hydrogen atoms are optionally substituted with a halogen atom and/or all available atoms are optionally substituted with an alternate isotope thereof. In some embodiments, R$^9$, R$^{10}$ and R$^{11}$ are independently selected from hydrogen, F, Cl, Br and CN wherein all available hydrogen atoms are optionally substituted with a halogen atom and/or all available atoms are optionally substituted with an alternate isotope thereof. In some embodiments, R$^9$, R$^{10}$ and R$^{11}$ are independently selected from hydrogen, deuterium, F, Cl, Br and CN. In some embodiments, R$^9$, R$^{10}$ and R$^{11}$ are independently selected from hydrogen and deuterium. In some embodiments, R$^9$, R$^{10}$ and R$^{11}$ are all hydrogen. In some embodiments, R$^9$, R$^{10}$ and R$^{11}$ are all deuterium. In some embodiments, R$^{10}$ is selected from hydrogen, deuterium, F, Cl, Br and CN and R$^9$ and R$^{11}$ are selected from hydrogen and deuterium. In some embodiments, R$^{10}$ is selected from hydrogen, deuterium, F and CN and R$^9$ and R$^{11}$ are selected from hydrogen and deuterium. In some embodiments, R$^{10}$ is selected from hydrogen, F and CN and R$^9$ and R$^{11}$ are selected from hydrogen and deuterium. In some embodiments, R$^{10}$ is selected from hydrogen, F and CN and R$^9$ and R$^{11}$ both hydrogen.

In some embodiments, the C$_3$-C$_7$cycloalkyl in R$^9$, R$^{10}$ and R$^{11}$ is independently selected from cyclopropyl, cyclobutyl, cyclopentyl and cyclohexyl, wherein all available hydrogen atoms are optionally substituted with a halogen atom and/or all available atoms are optionally substituted with an alternate isotope thereof.

In some embodiments, the 3- to 7-membered heterocyclic ring in R$^9$, R$^{10}$ and R$^{11}$ is, independently, a saturated or unsaturated heterocycle. In some embodiments, the 3 to 7-membered heterocyclic ring in R$^9$, R$^{10}$ and R$^{11}$ is, independently, a saturated or unsaturated bridged bicyclic heterocycle. In some embodiments, the saturated or unsaturated bridged bicyclic heterocycle is independently selected from azabicyclohexanyl, diazabicycloheptanyl, oxobicyclohexanyl, oxobicycloheptanyl and oxobicycloheptanenyl, wherein all available hydrogen atoms are optionally substituted with a halogen atom and/or all available atoms are optionally substituted with an alternate isotope thereof.

In some embodiments, the 3- to 7-membered heterocyclic ring in R$^9$, R$^{10}$ and R$^{11}$ is, independently, a saturated or unsaturated heterocycle. In some embodiments, the 3 to 7-membered heterocyclic ring in R$^9$, R$^{10}$ and R$^{11}$ is, independently, a saturated or unsaturated bridged bicyclic heterocycle. In some embodiments, the saturated or unsaturated bridged bicyclic heterocycle is independently, selected from azabicyclohexanyl, diazabicycloheptanyl, oxobicyclohexanyl, oxobicycloheptanyl and oxobicycloheptanenyl, wherein all available hydrogen atoms are optionally substituted with a halogen atom and/or all available atoms are optionally substituted with an alternate isotope thereof.

In some embodiments, the 3- to 7-membered heterocyclic ring in R$^9$, R$^{10}$ and R$^{11}$ is independently selected from aziridinyl, oxiranyl, thiiranyl, oxaxiridinyl, dioxiranyl, azetidinyl, oxetanyl, theitanyl, diazetidinyl, dioxetanyl, dithietanyl, tetrahydrofuranyl, tetrahydrothiophenyl, pyrrolidinyl, imidazolidinyl, pyrazolidinyl, isoxthiolidinyl, thiazolidinyl, isothiazolidinyl, dioxolanyl, dithiolanyl, piperidinyl, triazolyl, furazanyl, oxadiazolyl, thiadiazolyl, dioxazolyl, dithiazolyl, tetrazolyl, oxatetrazolyl, tetrahydropyranyl, diazinanyl (e.g., piperazinyl), morpholinyl, thiomorpholinyl, dioxanyl, dithianyl, azepanyl, oxepanyl, thiepanyl and diazepanyl, wherein all available hydrogen atoms are optionally substituted with a halogen atom and/or all available atoms are optionally substituted with an alternate isotope thereof.

In some embodiments, each R$^{12}$ is independently selected from hydrogen, substituted or unsubstituted C$_1$-C$_4$alkyl, substituted or unsubstituted C$_2$-C$_6$alkenyl, substituted or unsubstituted C$_2$-C$_6$alkynyl, substituted or unsubstituted C$_1$-C$_4$haloalkyl, substituted or unsubstituted C$_3$-C$_7$cycloalkyl, substituted or unsubstituted heterocycloalkyl, substituted or unsubstituted aryl, substituted or unsubstituted heteroaryl, substituted or unsubstituted $C_1$-$C_4$alkylene$C_3$-$C_7$cycloalkyl, substituted or unsubstituted $C_1$-$C_4$alkylene$C_3$-$C_7$heterocycloalkyl, substituted or unsubstituted $C_1$-$C_4$alkylenearyl and substituted or unsubstituted $C_1$-$C_4$alkyleneheteroaryl, wherein all available hydrogen atoms are optionally substituted with a halogen atom and/or all available atoms are optionally substituted with an alternate isotope thereof.

In some embodiments, the $C_3$-$C_7$cycloalkyl in each $R^{12}$ is independently selected from cyclopropyl, cyclobutyl, cyclopentyl and cyclohexyl, wherein all available hydrogen atoms are optionally substituted with a halogen atom and/or all available atoms are optionally substituted with an alternate isotope thereof.

In some embodiments, the heterocycloalkyl in each $R^{12}$ is independently a saturated or unsaturated heterocycle. In some embodiments heterocycloalkyl in each $R^{12}$ is independently a saturated or unsaturated bridged bicyclic heterocycle. In some embodiments, the saturated or unsaturated bridged bicyclic heterocycle is independently selected from azabicyclohexanyl, diazabicycloheptanyl, oxobicyclohexanyl, oxobicycloheptanyl and oxobicycloheptanenyl, wherein all available hydrogen atoms are optionally substituted with a halogen atom and/or all available atoms are optionally substituted with an alternate isotope thereof.

In some embodiments, the heterocycloalkyl in each $R^{12}$ is independently selected from aziridinyl, oxiranyl, thiiranyl, oxaxiridinyl, dioxiranyl, azetidinyl, oxetanyl, theitanyl, diazetidinyl, dioxetanyl, dithietanyl, tetrahydrofuranyl, tetrahydrothiophenyl, pyrrolidinyl, imidazolidinyl, pyrazolidinyl, isoxthiolidinyl, thiazolidinyl, isothiazolidinyl, dioxolanyl, dithiolanyl, piperidinyl, triazolyl, furazanyl, oxadiazolyl, thiadiazolyl, dioxazolyl, dithiazolyl, tetrazolyl, oxatetrazolyl, tetrahydropyranyl, diazinanyl (e.g, piperazinyl), morpholinyl, thiomorpholinyl, dioxanyl, dithianyl, azepanyl, oxepanyl, thiepanyl and diazepanyl, wherein all available hydrogen atoms are optionally substituted with a halogen atom and/or all available atoms are optionally substituted with an alternate isotope thereof.

In some embodiments, the heteroaryl in each $R^{12}$ is independently selected from, azepinyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl, wherein all available hydrogen atoms are optionally substituted with a halogen atom and/or all available atoms are optionally substituted with an alternate isotope thereof.

In some embodiments, each $R^{12}$ is independently selected from hydrogen, $C_1$-$C_4$alkyl and $C_2$-$C_6$alkenyl, wherein all available hydrogen atoms are optionally substituted with a halogen atom and/or all available atoms are optionally substituted with an alternate isotope thereof. In some embodiments, each $R^{12}$ is independently selected from hydrogen and $C_1$-$C_4$alkyl, wherein all available hydrogen atoms are optionally substituted with a halogen atom and/or all available atoms are optionally substituted with an alternate isotope thereof. In some embodiments, each $R^{12}$ is independently selected from hydrogen and $C_1$-$C_4$alkyl, wherein all available hydrogen atoms are optionally substituted with a halogen atom and/or all available hydrogen atoms are optionally substituted with deuterium. In some embodiments, $R^{12}$ is selected from hydrogen, deuterium, CHs, $CD_2H$, $CDH_2$, $CD_3$, $CH_2CH_3$ and $CD_2CD_3$. In some embodiments, each $R^{12}$ is independently selected from hydrogen, deuterium, $CH_3$, $CD_3$, $CH_2CH_3$ and $CD_2CD_3$. In some embodiments, each $R^{12}$ is independently selected from hydrogen, $CH_3$, $CD_3$, $CH_2CH_3$ and $CD_2CD_3$. In some embodiments, each $R^{12}$ in $R^1$ and/or A are both $CH_3$. In some embodiments, each $R^{12}$ in $R^1$ and/or A are both CDs. In some embodiments, each $R^{12}$ in $R^1$ and/or in A are both $CH_2CH_3$. In some embodiments, each $R^{12}$ in $R^1$ and/or in A are both $CD_2CD_3$. In some embodiments, each $R^{12}$ in $R^1$ and/or in A are both $CH_2CH_3$. In some embodiments, each $R^{12}$ in $R^1$ and/or in A are both hydrogen.

In some embodiments, each $R^{12}$ is independently selected from substituted or unsubstituted $C_1$-$C_4$alkylene$C_3$-$C_7$cycloalkyl, substituted or unsubstituted $C_1$-$C_4$alkylene$C_3$-$C_7$heterocycloalkyl, substituted or unsubstituted $C_1$-$C_4$alkylenearyl, substituted or unsubstituted $C_1$-$C_4$alkyleneheteroaryl, wherein all available hydrogen atoms are optionally substituted with a halogen atom and/or all available atoms are optionally substituted with an alternate isotope thereof. In some embodiments, each $R^{12}$ is independently selected from substituted or unsubstituted $C_1$-$C_4$alkylenearyl and substituted or unsubstituted $C_1$-$C_4$alkyleneheteroaryl, wherein all available hydrogen atoms are optionally substituted with a halogen atom and/or all available atoms are optionally substituted with an alternate isotope thereof. In some embodiments, each $R^{12}$ is independently substituted or unsubstituted $C_1$-$C_4$alkylenearyl wherein all available hydrogen atoms are optionally substituted with a halogen atom and/or all available atoms are optionally substituted with an alternate isotope thereof. In some embodiments, each $R^{12}$ is independently substituted or unsubstituted $CH_2$aryl wherein all available hydrogen atoms are optionally substituted with a halogen atom and/or all available atoms are optionally substituted with an alternate isotope thereof. In some embodiments, each $R^{12}$ is independently substituted or unsubstituted $CH_2$phenyl.

When $R^{12}$ is substituted, in some embodiments, the substituents are independently selected from one or more of Br, Cl, F, $CO_2H$, $CO_2CH_3$, $C(O)NH_2$, $C(O)N(CH_3)_2$, $C(O)NHCH_3$, $SO_2CH_3$, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl, $C_2$-$C_6$fluoroalkynyl, $C_3$-$C_6$cycloalkyl and a 3- to 6-membered heterocyclic ring including 1 to 2 ring heteromoieties selected from O, S, S(O), $SO_2$, N, NH and $NCH_3$. In some embodiments, the substituents on $R^{12}$ are independently selected from one to three of Br, Cl, F, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl and $C_2$-$C_6$fluoroalkynyl. In some embodiments, the substituents on $R^{12}$ are independently selected from one or two of Cl, F, $CH_3$ and $CF_3$.

In some embodiments, Y is halogen. In some embodiments, the halogen in Y is selected from F, Cl, Br and I. In some embodiments, the halogen in Y is selected from F, Cl and Br. In some embodiments, the halogen in Y is selected from F and Cl. In some embodiments, the halogen in Y is F.

In some embodiments, Y is X-A.

In some embodiments, X is selected from S, S(O) and $SO_2$. In some embodiments, X is selected from O, $NR^{13}$ and S, wherein all available hydrogen atoms are optionally substituted with a halogen atom and/or all available atoms are optionally substituted with an alternate isotope thereof. In some embodiments, X is selected from $NR^{13}$ and O. In some embodiments, X is O.

In some embodiments, A is selected from hydrogen, $C_1$-$C_6$alkyl, $C_2$-$C_6$alkenyl, $C_2$-$C_6$alkynyl, $C_3$-$C_7$cycloalkyl, $C_4$-$C_6$cycloalkenyl, heterocycloalkyl, aryl, heteroaryl and $P(O)(OR^{12})_2$, wherein all available hydrogen atoms are optionally substituted with a halogen atom and/or all available atoms are optionally substituted with an alternate isotope thereof. In some embodiments, A is selected from hydrogen, $C_1$-$C_6$alkyl, $C_2$-$C_6$alkenyl, $C_2$-$C_6$alkynyl, $C_3$-$C_7$cycloalkyl, $C_4$-$C_6$cycloalkenyl, heterocycloalkyl, aryl and heteroaryl, wherein all available hydrogen atoms are optionally substituted with a halogen atom and/or all available atoms are optionally substituted with an alternate isotope thereof. In some embodiments, A is selected from hydrogen, $C_1$-$C_4$alkyl and $C_2$-$C_6$alkenyl, wherein all available hydrogen atoms are optionally substituted with a halogen atom and/or all available atoms are optionally substituted with an alternate isotope thereof. In some embodiments, A selected from hydrogen and $C_1$-$C_4$alkyl wherein all available hydrogen atoms are optionally substituted with a halogen atom and/or all available atoms are optionally substituted with an alternate isotope thereof. In some embodiments, A is H. In some embodiments, A is $P(O)(OR^{12})_2$, wherein all available hydrogen atoms are optionally substituted with a halogen atom and/or all available atoms are optionally substituted with an alternate isotope thereof.

In some embodiments, each $R^{13}$ is independently selected from hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_7$cycloalkyl, and a 3- to 7-membered heterocyclic ring including 1 to 2 ring heteromoieties selected from O, S, S(O), $SO_2$, N and $NR^{14}$, wherein said $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_7$cycloalkyl and 3- to 7-membered heterocyclic ring groups are optionally substituted by one or more substituents independently selected from CN, $OR^{14}$, $N(R^{14})_2$ and $SR^{14}$, and wherein said $C_3$-$C_7$cycloalkyl and 3- to 7-membered heterocyclic ring are each further optionally substituted with a substituent selected from halogen, $CO_2R^{14}$, $C(O)N(R^{14})_2$, $SO_2R^{14}$, $C_1$-$C_6$alkyl, $C_1$-$C_6$haloalkyl, $C_2$-$C_6$alkenyl, $C_2$-$C_6$haloalkenyl, $C_2$-$C_6$alkynyl, and $C_2$-$C_6$haloalkynyl wherein all available hydrogen atoms are optionally substituted with a halogen atom and/or all available atoms are optionally substituted with an alternate isotope thereof.

In some embodiments, each $R^{13}$ is independently selected from hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_7$cycloalkyl, and a 3- to 7-membered heterocyclic ring including 1 to 2 ring heteromoieties selected from O, S, S(O), $SO_2$, N and $N(R^{14})$, wherein all available hydrogen atoms are optionally substituted with a halogen atom and/or all available atoms are optionally substituted with an alternate isotope thereof.

In some embodiments, each $R^{13}$ is independently selected from hydrogen, $C_1$-$C_6$alkyl, $C_2$-$C_6$alkenyl, $C_2$-$C_6$alkynyl, $C_3$-$C_7$cycloalkyl, and a 3- to 7-membered heterocyclic ring including 1 to 2 ring heteromoieties selected from O, S, S(O), $SO_2$, N and $N(R^{14})$, wherein all available hydrogen atoms are optionally substituted with a halogen atom and/or all available atoms are optionally substituted with an alternate isotope thereof. In some embodiments, each $R^{13}$ is independently selected from hydrogen, $C_1$-$C_6$alkyl, $C_2$-$C_6$alkenyl and $C_2$-$C_6$alkynyl, wherein all available hydrogen atoms are optionally substituted with a halogen atom and/or all available atoms are optionally substituted with an alternate isotope thereof. In some embodiments, each $R^{13}$ is independently selected from hydrogen, $C_1$-$C_6$alkyl, $C_2$-$C_6$alkenyl and $C_2$-$C_6$alkynyl, wherein all available hydrogen atoms are optionally substituted with a halogen atom and/or all available hydrogen atoms are optionally substituted with deuterium. In some embodiments, each $R^{13}$ is independently selected from hydrogen and $C_1$-$C_6$alkyl wherein all available hydrogen atoms are optionally substituted with a halogen atom and/or all available hydrogen atoms are optionally substituted with deuterium. In some embodiment, each $R^{13}$ is independently selected from hydrogen, deuterium, F, $CH_3$, $CF_3$, $CD_2H$, $CDH_2$, $CD_3$, $CH_2CH_3$, $CF_2CF_3$, and $CD_2CD_3$. In some embodiment, each $R^{13}$ is independently selected from hydrogen, deuterium, $CH_3$, $CD_2H$, $CDH_2$, $CD_3$, $CH_2CH_3$, and $CD_2CD_3$. In some embodiment, each $R^{13}$ is hydrogen. In some embodiment, each $R^{13}$ is independently $CH_3$ or $CD_3$.

In some embodiments, $R^{14}$ is selected from hydrogen, substituted or unsubstituted $C_1$-$C_4$alkyl, substituted or unsubstituted $C_2$-$C_6$alkenyl, substituted or unsubstituted $C_2$-$C_6$alkynyl, substituted or unsubstituted $C_1$-$C_4$haloalkyl, substituted or unsubstituted $C_3$-$C_7$cycloalkyl, substituted or unsubstituted heterocycloalkyl, substituted or unsubstituted aryl and substituted or unsubstituted heteroaryl, wherein all available hydrogen atoms are optionally substituted with a halogen atom and/or all available atoms are optionally substituted with an alternate isotope thereof.

In some embodiments, $R^{14}$ is selected from hydrogen, $C_1$-$C_4$alkyl and $C_2$-$C_6$alkenyl, wherein all available hydrogen atoms are optionally substituted with a halogen atom and/or all available atoms are optionally substituted with an alternate isotope thereof. In some embodiments, $R^{14}$ is selected from hydrogen and $C_1$-$C_4$alkyl, wherein all available hydrogen atoms are optionally substituted with a halogen atom and/or all available atoms are optionally substituted with an alternate isotope thereof. In some embodiments, $R^{14}$ is selected from hydrogen and $C_1$-$C_4$alkyl, wherein all available hydrogen atoms are optionally substituted with a halogen atom and/or all available hydrogen atoms are optionally substituted with deuterium. In some embodiments, $R^{14}$ is hydrogen, deuterium, F, Br, $CH_3$, $CF_3$, $CD_2H$, $CDH_2$, $CD_3$, $CH_2CH_3$, $CF_2CF_3$, and $CD_2CD_3$. In some embodiments, $R^{14}$ is selected is from hydrogen, deuterium, $CH_3$, $CD_2H$, $CDH_2$, $CD_3$, $CH_2CH_3$ and $CD_2CD_3$. In some embodiments, $R^{14}$ is selected from hydrogen, deuterium, $CH_3$ and $CD_3$. In some embodiments, $R^{14}$ is hydrogen.

When $R^{14}$ is substituted, in some embodiments, the substituents are independently selected from one or more of Br, C, F, $CO_2H$, $CO_2CH_3$, $C(O)NH_2$, $C(O)N(CH_3)_2$, $C(O)NHCH_3$, $SO_2CH_3$, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl, $C_2$-$C_6$fluoroalkynyl, $C_3$-$C_6$cycloalkyl and a 3- to 6-membered heterocyclic ring including 1 to 2 ring heteromoieties selected from O, S, S(O), $SO_2$, N, NH and $NCH_3$. In some embodiments, the substituents on $R^4$ are independently selected from one to three of Br, C, F, $C_1$-$C_4$alkyl, $C_1$-$C_4$fluoralkyl, $C_2$-$C_6$alkenyl, $C_2$-$C_6$fluoroalkenyl, $C_2$-$C_6$alkynyl and $C_2$-$C_6$fluoroalkynyl. In some embodiments, the substituents on $R^4$ are independently selected from one or two of Br, C, F, $CH_3$ and $CF_3$.

In some embodiments, when Y is X-A, X is O and A is $P(O)(OR^{12})_2$ the compound of Formula (I) is a compound of Formula (I-A). Accordingly, in another embodiment, the application includes a compound of Formula (I-A) or a pharmaceutically acceptable salt, solvate or prodrug thereof:

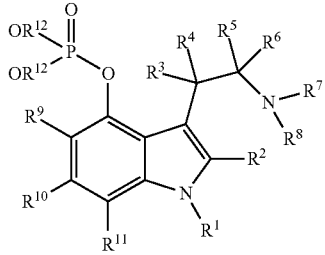

(I-A)

wherein:
$R^1$, $R^2$, $R^3$, $R^4$, $R^5$, $R^6$, $R^7$, $R^8$, $R^9$, $R^{10}$, $R^{11}$ and $R^{12}$ are as defined in Formula (I), wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, when Y is X-A, X is O and A is $P(O)(OR^{12})_2$, and $R^9$ and $R^{11}$ are both H, the compound of Formula (I) is a compound of Formula (I-B). Accordingly, in some embodiments, the application includes a compound of Formula (I-B) or a pharmaceutically acceptable salt, solvate and/or prodrug thereof:

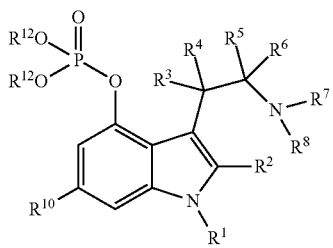

(I-B)

wherein
$R^1$, $R^2$, $R^3$, $R^4$, $R^5$, $R^6$, $R^7$, $R^8$, $R^{10}$ and $R^{12}$ are as defined in Formula (I), wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, when Y is X-A, X is O and A is $P(O)(OH)_2$, $R^9$ and $R^1$ are both H and $R^1$ is H, the compound of Formula (I) is a compound of Formula (I-D). Accordingly, in an embodiment, the application includes a compound of Formula (I-D) or a pharmaceutically acceptable salt, solvate and/or prodrug thereof:

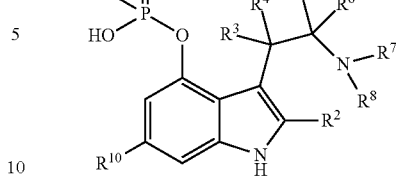

(I-D)

wherein:
$R^2$, $R^3$, $R^4$, $R^5$, $R^6$, $R^7$, $R^8$ and $R^{10}$ are as defined in Formula (I), wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, Y is X-A and the compound of Formula (I) is a compound of Formula (I-H). Accordingly, in some embodiments, the application includes a compound of Formula (I-H) or a pharmaceutically acceptable salt, solvate and/or prodrug thereof:

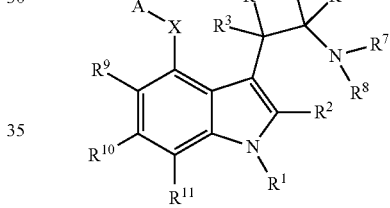

(I-H)

wherein:
A, X, $R^1$, $R^2$, $R^3$, $R^4$, $R^5$, $R^6$, $R^7$ $R^8$, $R^9$, $R^{10}$ and $R^{11}$ are as defined in Formula (I), and wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, Y is halogen and the compound of Formula (I) is a compound of Formula (I-I). Accordingly, in some embodiments, the application includes a compound of Formula (I-I) or a pharmaceutically acceptable salt, solvate and/or prodrug thereof:

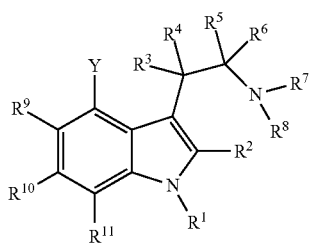

(I-I)

wherein:

Y is halogen; and $R^1$, $R^2$, $R^3$, $R^4$, $R^5$, $R^6$, $R^7$ $R^8$, $R^9$, $R^{10}$ and $R^1$ are as defined in Formula (I), and wherein at least one of $R^3$, $R^4$, $R^5$ and $R^6$ is deuterium or at least one of $R^3$, $R^4$, $R^5$ and $R^6$ comprises deuterium, and wherein all available hydrogen atoms are optionally substituted with a halogen atom and/or all available atoms are optionally substituted with an alternate isotope thereof.

In some embodiments, in the compounds of Formula (I-I), Y is selected from F, Cl and Br. In some embodiments, in the compounds of Formula (I-I), Y is selected from F and Br. In some embodiments, in the compounds of Formula (I-I), Y is F.

In some embodiments, Y is X-A and A is $C_{1-6}$ alkyl and the compound of Formula (I) is a compound of Formula (I-J). Accordingly, in some embodiments, the application includes a compound of Formula (I-H) or a pharmaceutically acceptable salt, solvate and/or prodrug thereof:

(I-J)

[chemical structure]

wherein:

A is $C_{1-6}$ alkyl; and

X, $R^1$, $R^2$, $R^3$, $R^4$, $R^5$, $R^6$, $R^7$ $R^8$, $R^9$, $R^{10}$ and $R^{11}$ are as defined in Formula (I), and wherein all available hydrogen atoms are optionally substituted with a halogen atom and/or all available atoms are optionally substituted with an alternate isotope thereof.

In some embodiments, A in the compound of Formula (I-J) is selected from $CH_3$, $CD_2H$, $CDH_2$, $CD_3$, $CH_2CH_3$, $CH_2CH_2D$, $CH_2CD_2H$ and $CD_2CD_3$. In some embodiments, A in the compound of Formula (I-J) selected from $CH_3$, $CD_3$, $CH_2CH_3$ and $CD_2CD_3$. In some embodiments, A in the compound of Formula (I-J) selected from $CH_3$, and $CD_3$.

In some embodiments, in the compounds of Formula (I-A), (I-B) and (I-H) to (I-J), $R^1$ is selected from hydrogen, $C_1$-$C_3$alkyl, $C(O)R^{12}$, $CO_2OR^{12}$, $C(O)N(R^{12})_2$, $S(O)R^{12}$ and $SO_2R^{12}$; wherein all available hydrogen atoms are optionally substituted with a halogen atom and/or all available atoms are optionally substituted with an alternate isotope thereof. In some embodiments, in the compounds of Formula (I-A), (I-B) and (I-H) to (I-J), $R^1$ is selected from hydrogen, $C_1$-$C_3$alkyl, $C(O)R^9$ and $CO_2R^9$, wherein all available hydrogen atoms are optionally substituted with a halogen atom and/or all available atoms are optionally substituted with an alternate isotope thereof. In some embodiments, in the compounds of Formula (I-A), (I-B) and (I-H) to (I-J), $R^1$ is selected from hydrogen, $CH_3$, $CH_2CH_3$, and $CH(CH_3)_2$, wherein all available hydrogen atoms are optionally substituted with a halogen atom and/or all available atoms are optionally substituted with an alternate isotope thereof. In some embodiments, in the compounds of Formula (I-A), (I-B) and (I-H) to (I-J), $R^1$ is selected from hydrogen, deuterium, Br, F, $CH_3$, $CF_3$, $CD_3$, $CH_2CH_3$, $CD_2CD_3$, $CF_2CF_3$, $CH(CH_3)_2$, $CD(CD_3)_2$, $CF(CF_3)_2$, $C(CD_3)_3$, $C(CF_3)_3$, and $C(CH_3)_2$. In some embodiments, in the compounds of Formula (I-A), (I-B) and (I-H) to (I-J), $R^1$ is selected from hydrogen, deuterium, $CH_3$, $CF_3$ and $CD_3$. In some embodiments, in the compounds of Formula(I-A), (I-B) and (I-H) to (I-J), $R^1$ is hydrogen.

In some embodiments, in the compounds of Formula (I-A), (I-B), (I-D), (I-H) to (I-J), $R^2$ is selected from hydrogen and $C_1$-$C_4$alkyl, wherein all available hydrogen atoms are optionally substituted with a halogen atom and/or all available atoms are optionally substituted with an alternate isotope thereof. In some embodiments, in the compounds of Formula (I-A), (I-B), (I-D), (I-H) to (I-J), $R^2$ is selected from hydrogen, $CH_3$, $CH_2CH_3$, $CH(CH_3)_2$ and $C(CH_3)_3$, wherein all available hydrogen atoms are optionally substituted with a halogen atom and/or all available hydrogen atoms are optionally substituted with deuterium. In some embodiments, in the compounds of Formula (I-A), (I-B), (I-D), (I-H) to (I-J), $R^2$ is selected from hydrogen and deuterium, F, $CH_3$, $CF_3$, $CD_3$, $CH_2CH_3$, $CD_2CD_3$, $CF_2CF_3$, $CH(CH_3)_2$, $CD(CD_3)_2$, $CF(CF_3)_2$, $C(CD_3)_3$, $C(CF_3)_3$, and $C(CH_3)_3$. In some embodiments, in the compounds of Formula (I-A), (I-B), (I-D), (I-H) to (I-J), $R^2$ is selected from hydrogen and deuterium. In some embodiments, $R^2$ is hydrogen.

In some embodiments, in the compounds of Formula (I-A), (I-B), (I-D), (I-H) to (I-J), $R^3$, $R^4$, $R^5$ and $R^6$ are independently selected from hydrogen and $C_1$-$C_4$alkyl, wherein at least one of $R^3$, $R^4$, $R^5$ and $R^6$ is deuterium or at least one of $R^3$, $R^4$, $R^5$ and $R^6$ comprises deuterium and wherein all available hydrogen atoms are optionally substituted with a halogen atom and/or all available atoms are optionally substituted with an alternate isotope thereof. In some embodiments, in the compounds of Formula (I-A), (I-B), (I-D), (I-H) to (I-J), $R^3$, $R^4$, $R^5$ and $R^6$ are independently selected from hydrogen, $CH_3$, $CH_2CH_3$, $CH(CH_3)_2$ and $C(CH_3)_3$, wherein all available hydrogen atoms are optionally substituted with a halogen atom and/or all available hydrogen atoms are optionally substituted with deuterium and wherein at least one of $R^3$, $R^4$, $R^5$ and $R^6$ is deuterium or at least one of $R^3$, $R^4$, $R^5$ and $R^6$ comprises deuterium. In some embodiments, in the compounds of Formula (I-A), (I-B), (I-D), (I-H) to (I-J), $R^3$, $R^4$, $R^5$ and $R^6$ are independently selected from hydrogen, deuterium, Br, F, $CH_3$, $CD_2H$, $CDH_2$, $CD_3$, $CH_2CH_3$, $CH_2CH_2D$, $CH_2CD_2H$ and $CD_2CD_3$, wherein at least one of $R^3$, $R^4$, $R^5$ and $R^6$ is deuterium or at least one of $R^3$, $R^4$, $R^5$ and $R^6$ comprises deuterium. In some embodiments, $R^3$, $R^4$, $R^5$ and $R^6$ are independently selected from hydrogen, deuterium, F, $CH_3$, $CD_2H$, $CDH_2$ and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, in the compounds of Formula (I-A), (I-B), (I-D), (I-H), to (I-J) $R^3$, $R^4$, $R^5$ and $R^6$ are independently selected from hydrogen, deuterium, $CH_3$ and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, in the compounds of Formula (I-A), (I-B), (I-D), (I-H) to (I-J), $R^3$, $R^4$, $R^5$ and $R^6$ are independently selected from hydrogen, deuterium and $CD_3$, wherein at least one of $R^3$, $R^4$, $R^5$ and $R^6$ is deuterium or at least one of $R^3$, $R^4$, $R^5$ and $R^6$ comprises deuterium. In some embodiments, in the compounds of Formula (I-A), (I-B), (I-D), (I-H) to (I-J) at least one of $R^3$ and $R^4$ or $R^5$ and $R^6$ is $CD_3$. In some embodiments, in the compounds of Formula (I-A), (I-B), (I-D), (I-H) to (I-J), $R^3$ and $R^4$ are both $CD_3$, or $R^5$ and $R^6$ are both $CD_3$. In some embodiments, in the compounds of Formula (I-A), (I-B), (I-D), (I-H) to (I-J), $R^3$, $R^4$, $R^5$ and $R^6$ are all $CD_3$. In some embodiments, in the compounds of Formula (I-A), (I-B), (I-D), (I-H) to (I-J), $R^3$ and $R^4$ are both deuterium, or $R^5$ and $R^6$ are both deuterium. In some embodiments, in the compounds of Formula (I-A), (I-B), (I-D), (I-H) to (I-J), $R^3$, $R^4$, $R^5$ and $R^6$ are all deuterium.

In some embodiments in the compounds of Formula (I-A), (I-B), (I-D), (I-H) to (I-J), $R^7$ and $R^8$ are independently selected from hydrogen, deuterium, Br, F, $CH_3$, $CF_3$, $CD_2H$, $CDH_2$, $CD_3$, $CH_2CH_3$, $CF_2CF_3$, and $CD_2CD_3$. In some embodiments, in the compounds of Formula (I-A), (I-B), (I-D), (I-H) to (I-J), $R^7$ and $R^8$ are independently selected from hydrogen, deuterium, $CH_3$, $CD_3$, $CH_2CH_3$ and $CD_2CD_3$. In some embodiments. in the compounds of Formula (I-A), (I-B), (I-D), (I-H) to (I-J), $R^7$ and $R^8$ are both hydrogen, deuterium, $CH_3$, $CD_3$, $CH_2CH_3$ or $CD_2CD_3$. In some embodiments, in the compounds of Formula (I-A), (I-B), (I-D), (I-H) to (I-J), $R^7$ and $R^8$ are both hydrogen. In some embodiments, in the compounds of Formula (I-A), (I-B), (I-D), (I-H) to (I-J), $R^7$ and $R^8$ are both $CH_3$. In some embodiments, in the compounds of Formula (I-A), (I-B), (I-D), (I-H) and (I-K), $R^7$ and $R^8$ are both $CD_3$. In some embodiments, in the compounds of Formula (I-A), (I-B), (I-D), (I-H) to (I-J), $R^7$ and $R^8$ are both $CH_2CH_3$. In some embodiments, in the compounds of Formula (I-A), (I-B), (I-D), (I-H) to (I-J), $R^7$ and $R^8$ are both $CD_2CD_3$.

In some embodiments, in the compounds of Formula (I-A), (I-B), (I-D), (I-H) to (I-J), at least one of $R^3$, $R^4$, $R^5$ and $R^6$ is deuterium or at least one of $R^3$, $R^4$, $R^5$ and $R^6$ comprises deuterium and $R^7$ and $R^8$ are independently selected from hydrogen, deuterium, $CH_3$, $CD_3$, $CH_2CH_3$ and $CD_2CD_3$. In some embodiments, in the compounds of Formula (I-A), (I-B), (I-D), (I-H) to (I-J), at least one of $R^3$ and $R^4$ or $R^5$ and $R^6$ is deuterium and $R^7$ and $R^8$ are both hydrogen, deuterium, $CH_3$, $CD_3$, $CH_2CH_3$ or $CD_2CD_3$. In some embodiments, in the compounds of Formula (I-A), (I-B), (I-D), (I-H) to (I-J), $R^3$, $R^3$, $R^4$, $R^5$ and $R^6$ are all deuterium and $R^7$ and $R^8$ are both hydrogen, deuterium, $CH_3$, $CD_3$, $CH_2CH_3$ or $CD_2CD_3$.

In some embodiments, in the compounds of Formula (I-A), (I-B), (I-D), (I-H) to (I-J), $R^7$ and $R^8$ are taken together with the nitrogen atom therebetween to form pyrrolidinyl, piperidinyl or diazinanyl, wherein all available hydrogen atoms are optionally substituted with a halogen atom and/or all available hydrogens are optionally substituted with deuterium. In some embodiments, in the compounds of Formula (I-A), (I-B), (I-D), (I-H) to (I-J), $R^3$, $R^4$, $R^5$ and $R^6$ are all hydrogen or $R^3$, $R^4$, $R^5$ and $R^6$ are all deuterium and $R^7$ and $R^8$ are taken together with the nitrogen atom therebetween to form pyrrolidinyl, piperidinyl or diazinanyl, wherein all available hydrogen atoms are optionally substituted with a halogen atom and/or all available hydrogens are optionally substituted with deuterium.

In some embodiments, in the compound of Formula (I-A), (I-H) to (I-J), $R^9$, $R^{10}$ and $R^{11}$ are independently selected from hydrogen, F, Cl, Br, CN, $OR^{13}$, $N(R^{13})_2$, $SR^{13}$, $CH_3$, $CH_2CH_3$, $CH(CH_3)_2$, $C(CH_3)_3$, $C_1$-$C_4$haloalkyl, $C_2$-$C_6$haloalkenyl, $CO_2R^{13}$, $S(O)R^{13}$, $SO_2R^{13}$ and $C_2$-$C_6$alkenyl, wherein all available hydrogen atoms are optionally substituted with a halogen atom and/or all available atoms are optionally substituted with an alternate isotope thereof. In some embodiments, in the compound of Formula (I-A), (I-H) to (I-J), $R^9$, $R^{10}$ and $R^1$ are independently selected from hydrogen, F, Cl, Br and CN wherein all available hydrogen atoms are optionally substituted with a halogen atom and/or all available atoms are optionally substituted with an alternate isotope thereof. In some embodiments, in the compound of Formula (I-A), (I-H) to (I-J), $R^9$, $R^{10}$ and $R^{11}$ are independently selected from hydrogen, deuterium, F, Cl, Br and CN. In some embodiments, in the compound of Formula (I-A), (I-H) to (I-J), $R^9$, $R^{10}$ and $R^{11}$ are independently selected from hydrogen and deuterium. In some embodiments, in the compound of Formula (I-A), (I-H) to (I-J), $R^9$, $R^{10}$ and $R^{11}$ are all hydrogen. In some embodiments, in the compound of Formula (I-A), (I-H) to (I-J), $R^9$, $R^{10}$ and $R^{11}$ are all deuterium. In some embodiments, in the compound of Formula (I-A), (I-H) to (I-J), $R^{10}$ is selected from hydrogen, deuterium, F, Cl, Br and CN and $R^9$ and $R^{11}$ are selected from hydrogen and deuterium. In some embodiments, in the compound of Formula (I-A), (I-H) to (I-J), $R^{10}$ is selected from hydrogen, deuterium, F and CN and $R^9$ and $R^{11}$ are selected from hydrogen and deuterium. In some embodiments, in the compound of Formula (I-A), (I-H) to (I-J), $R^{10}$ is selected from hydrogen, F and CN and $R^9$ and $R^{11}$ are selected from hydrogen and deuterium. In some embodiments, in the compound of Formula (I-A), (I-H) to (I-J), $R^{10}$ is selected from hydrogen, F and CN and $R^9$ and $R^{11}$ both hydrogen. In some embodiments, in the compound of Formula (I-A), (I-H) to (I-J), $R^{10}$ is selected from hydrogen, deuterium, F, C, Br and CN.

In some embodiments, the compounds of Formula (I) are selected from:
3-(2-(bis(methyl-d3)amino)ethyl-1,1,2,2-d4)-1H-indol-4-yl dihydrogen phosphate
2-(4-fluoro-1H-indol-3-yl)-N,N-bis(methyl-d3)ethan-1-amine-1,1,2,2-d4
2-(4-methoxy-1H-indol-3-yl)-N,N-bis(methyl-d3)ethan-1-amine-1,1,2,2-d4; and
3-(2-(bis(methyl-d3)amino)ethyl-1,1,2,2-d4)-1H-indol-4-ol, or a pharmaceutically acceptable salt, solvate and/or prodrug thereof.

In some embodiments, the compound of Formula (I) is:

| Compound ID # | IUPAC Name | Chemical Formula/ Molecular Weight | Chemical Structure |
|---|---|---|---|
| I-3 | 3-(2-(bis(methyl-d3)amino)ethyl-1,1,2,2-d4)-1H-indol-4-yl dihydrogen phosphate | C12H7D10N2O4P 294.31 | 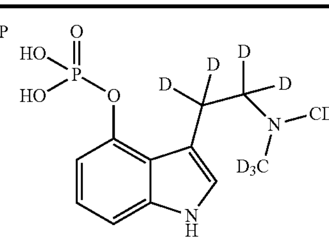 |

-continued

| Compound ID # | IUPAC Name | Chemical Formula/ Molecular Weight | Chemical Structure |
|---|---|---|---|
| I-43 | 2-(4-fluoro-1H-indol-3-yl)-N,N-bis(methyl-d3)ethan-1-amine-1,1,2,2-d4 | C12H5D10FN2 216.33 | 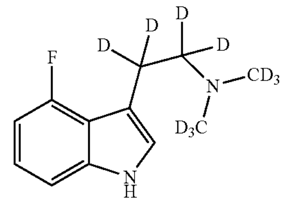 [SMILES: [2H]C([2H])([2H])N(C([2H])([2H])[2H])C([2H])([2H])C([2H])([2H])c1c[nH]c2cccc(F)c12] |
| I-44 | 2-(4-methoxy-1H-indol-3-yl)-N,N-bis(methyl-d3)ethan-1-amine-1,1,2,2-d4 | C13H8D10N2O 228.36 | and |
| I-45 | 3-(2-(bis(methyl-d3)amino)ethyl-1,1,2,2-d4)-1H-indol-4-ol | C12H6D10N2O 214.33 | | or a pharmaceutically acceptable salt, solvate and/or prodrug thereof.

In another embodiment, the application includes a compound of Formula (IA) or a pharmaceutically acceptable salt, solvate or prodrug thereof:

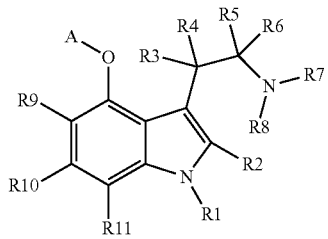

Formula (IA)

or a pharmaceutically acceptable salt thereof,
wherein $R^1$ is selected from the group consisting of hydrogen, $C_1$-$C_3$ alkyl, —$(CH_2)P(O)(OR^{12})$; $CO(R^{12})$, $COO(R^{12})$, $C(O)N(R^{12})_2$, $SO(R^{12})$ and $SO_2(R^{12})$;
$R^2$ to $R^6$ are independently selected from the group consisting of hydrogen and lower alkyl;
$R^7$ and $R^8$ are independently selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, wherein $R^7$ and $R^8$ may be taken together with the atoms to which they are attached form a 3- or 7-membered heterocyclic ring including 1 to 2 ring members selected from the group consisting of O, S, $SO_2$, N, and $N(R^{13})$ wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, SR6, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl;
$R^9$, $R^{10}$, and $R^{11}$ are independently selected from the group consisting of hydrogen, halogen, CN, $OR^{13}$, $N(R^{13})_2$, $SR^{13}$, $C_1$-$C_6$ alkyl, $C_1$-$C_6$ haloalkyl, $C_1$-$C_6$ alkyl substituted by $OR^{13}$, $C_1$-$C_6$ alkyl substituted by $SR^{13}$, $C_1$-$C_6$ alkyl substituted by $N(R^{13})_2$, $C_2$-$C_6$ haloalkyl, $COOR^{13}$, $C(O)N(R^{13})_2$, $SO_2R^{13}$, $COOR^{13}$, $C(O)N(R^{13})_2$, $SO_2R^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl;

wherein $R^{12}$ is selected from hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

$R^{13}$ is selected from the group consisting of hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C_1$-$C_6$ alkyl substituted by $OR^{13}$, $C_1$-$C_6$ alkyl substituted by $SR^{13}$, $C_1$-$C_6$ alkyl substituted by $N(HR^{13})$, $N(R^{13})_2$, $C_2$-$C_6$ haloalkyl, $COOR^{13}$, $C(O)N(R^{13})_2$, $SO_2R^{13}$, $COOR^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl; and A is selected from hydrogen, alkyl, alkenyl, alkynyl, cycloalkyl, cycloalkenyl, heterocycloalkyl, heterocycloaalkenyl, heterocycloaalkynyl, heterocycloalkynyl aryl, heteroaryl, $C_0$-$C_1$ $P(O)(OR^{12})_2$, $CO(Q')$, $COO(Q')$, $C(O)N(Q')_2$, $SO(Q')$, $SO_2(Q')$, where Q' is selected from hydrogen, $C_1$-$C_{20}$ alkyl, $C_1$-$C_{20}$ haloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_{20}$ alkyl, $C_2$-$C_{20}$ haloalkyl, $C_2$-$C_6$ alkenyl, $C_2$-$C_{20}$ haloalkenyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl; and wherein $R^{12}$ and $R^{13}$ are independently defined as above.

In one embodiment, the compounds of general formula (I), and pharmaceutically acceptable salts of the foregoing, the compounds are isotopically enriched with deuterium. In aspects of these embodiments, one or more of $R^1$, $R^2$, $R^3$, $R^4$, $R^5$, $R^6$, $R^7$, $R^8$, $R^9$, $R^{10}$, $R^{11}$, $R^{12}$ and $R^{13}$ may include deuterium;

In an embodiment, the application includes a compound of Formula (IB) or Formula (1C) or a pharmaceutically acceptable salt, solvate or prodrug thereof:

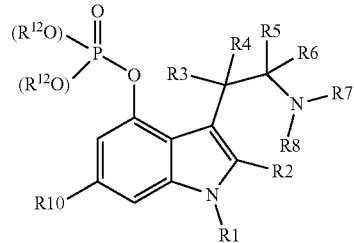

(IB)

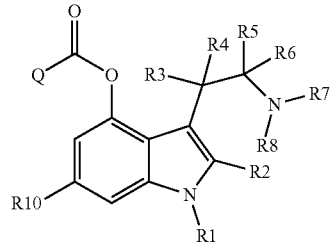

(IC)

wherein $R^1$ is selected from the group consisting of hydrogen, $C_1$-$C_3$ alkyl, —$(CH_2)P(O)(OR^{12})$; $CO(R^{12})$, $COO(R^{12})$, $C(O)N(R^{12})_2$, $SO(R^{12})$ and $SO_2(R^{12})$;

$R^2$ to $R^6$ are independently selected from the group consisting of hydrogen and lower alkyl;

$R^7$ and $R^8$ are independently selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, wherein $R^7$ and $R^8$ may be taken together with the atoms to which they are attached form a 3- or 7-membered cyclic or heterocyclic ring;

$R^{10}$ is selected from the group consisting of hydrogen, halogen, CN, $OR^{13}$, $N(R^{13})_2$, $SR^{13}$, $C_1$-$C_6$ alkyl, $C_1$-$C_6$ haloalkyl, where $R^{13}$ is selected from the group consisting of hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, wherein $R^{12}$ is selected from hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

$R^{13}$ is selected from the group consisting of hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C_1$-$C_6$ alkyl substituted by $OR^{13}$, $C_1$-$C_6$ alkyl substituted by $SR^{13}$, $C_1$-$C_6$ alkyl substituted by $N(HR^{13})$, $N(R^{13})_2$, $C_2$-$C_6$ haloalkyl, $COOR^{13}$, $C(O)N(R^{13})_2$, $SO_2R^{13}$, $COOR^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl;

Q is selected from hydrogen, $C_1$-$C_{20}$ alkyl, $C_1$-$C_{20}$ haloalkyl, $C_2$-$C_{20}$ alkenyl, $C_2$-$C_{20}$ haloalkenyl, $C_2$-$C_{20}$ alkynyl, $C_2$-$C_{20}$ haloalkynyl, $C_3$-$C_7$ cycloalkyl, and a 3- to 7-membered heterocyclic ring including 1 to 2 ring members selected from the group consisting of O, S, N, and $N(R^{10})$, wherein said $C_1$-$C_{20}$ alkyl, $C_2$-$C_{20}$ haloalkyl, $C_2$-$C_6$ alkenyl, $C_2$-$C_{20}$ haloalkenyl, $C_3$-$C_7$ cycloalkyl, and 3- to 7-membered heterocyclic ring groups are optionally substituted by one or more substituents independently selected from the group consisting of CN, $OR^{10}$, $N(R^{10})_2$, and $SR^{10}$, and wherein said $C_3$-$C_7$cycloalkyl and 3- to 7-membered heterocyclic ring are each further optionally substituted with a member of the group consisting of $C_1$-$C_3$ alkyl and $C_1$-$C_3$ haloalkyl;

wherein $R^9$ and $R^{10}$ are independently defined as above; and wherein $R^{12}$ and $R^{13}$ are independently defined as above;

In one embodiment, the compounds of general formula (Ia), and pharmaceutically acceptable salts of the foregoing, the compounds are isotopically enriched with deuterium. In aspects of these embodiments, one or more of $R^1$, $R^2$, $R^3$, $R^4$, $R^5$, $R^6$, $R^7$, $R^8$, $R^{10}$, $R^{12}$ and $R^{13}$ may include deuterium;

In an embodiment, the present application includes a compound of Formula (ID), (IE) and (IF) or a pharmaceutically acceptable salt, solvate or prodrug thereof:

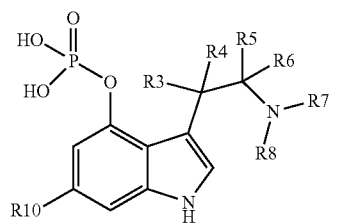
(ID)

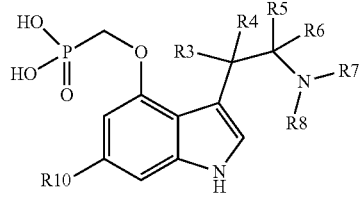
(IE)

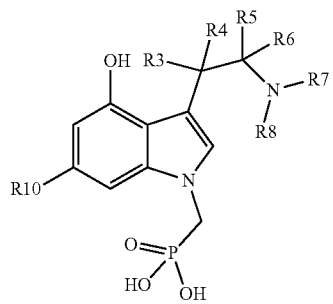
(IF)

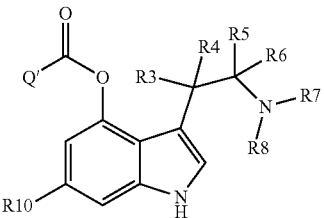
(IG)

$R^3$ to $R^6$ are independently selected from the group consisting of hydrogen and deuterium;

$R^7$ and $R^8$ are independently selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, wherein $R^7$ and $R^8$ may be taken together with the atoms to which they are attached form a 3- or 7-membered cyclic or heterocyclic ring; $R^{10}$ is selected from the group consisting of hydrogen, halogen, cyano and lower alkyl;

Q' is selected from the group consisting of:

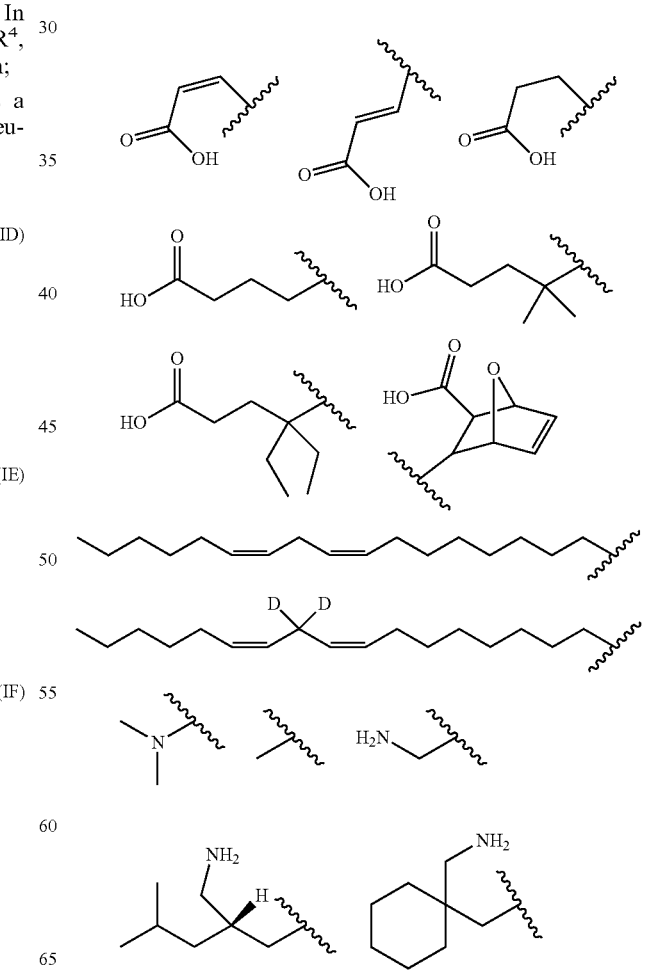

In an embodiment, the application includes a compound of Formula (IB) and Formula (1C) or a pharmaceutically acceptable salt, solvate or prodrug thereof:

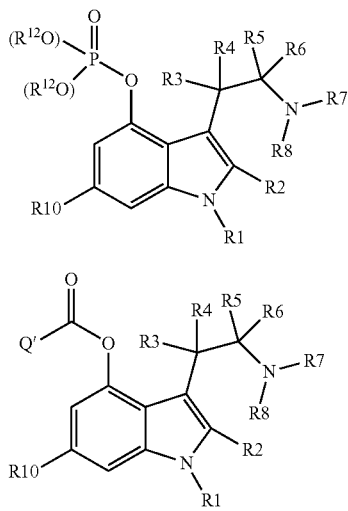

(IB')

(IC')

wherein R¹ is selected from the group consisting of hydrogen, $C_1$-$C_3$ alkyl, —$(CH_2)P(O)(OR^{12})$; $CO(R^{12})$, $COO(R^{12})$, $C(O)N(R^{12})_2$, $SO(R^{12})$ and $SO_2(R^{12})$;

$R^2$ to $R^6$ are independently selected from the group consisting of hydrogen and lower alkyl;

$R^7$ and $R^8$ are independently selected from the group consisting of hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl, wherein $R^7$ and $R^8$ may be taken together with the atoms to which they are attached form a 3- or 7-membered cyclic or heterocyclic ring;

$R^{10}$ is selected from the group consisting of hydrogen, halogen, cyano and lower alkyl;

wherein $R^{12}$ is selected from hydrogen, substituted or unsubstituted alkyl, substituted or unsubstituted alkenyl, substituted or unsubstituted alkynyl, substituted or unsubstituted haloalkyl, substituted or unsubstituted cycloalkyl, substituted or unsubstituted heterocycloalkyl, substituted or unsubstituted aryl, and substituted or unsubstituted heteroaryl;

$R^{13}$ is selected from the group consisting of hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, $C_1$-$C_6$ alkyl substituted by $OR^{13}$, $C_1$-$C_6$ alkyl substituted by $SR^{13}$, $C_1$-$C_6$ alkyl substituted by $N(HR^{13})$, $N(R^{13})_2$, $C_2$-$C_6$ haloalkyl, $COOR^{13}$, $C(O)N(R^{13})_2$, $SO_2R^{13}$, $COOR^{13}$, $C_1$-$C_6$ alkyl, $C_2$-$C_6$, alkenyl, $C_2$-$C_6$ haloalkenyl, $C_2$-$C_6$ alkynyl, $C_2$-$C_6$ haloalkynyl, $C_3$-$C_7$ cycloalkyl, and a 3- to 7-membered heterocyclic ring including 1 to 2 ring members selected from the group consisting of O, S, N, and $N(R^{13})$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, and 3- to 7-membered heterocyclic ring groups are optionally substituted by one or more substituents independently selected from the group consisting of CN, $OR^{13}$, $N(R^{13})_2$, and $SR^{13}$, and wherein said $C_3$-$C_7$ cycloalkyl and 3- to 7-membered heterocyclic ring are each further optionally substituted with a member of the group consisting of $C_1$-$C_3$ alkyl and $C_1$-$C_3$ haloalkyl, halogen, CN, $OR^{13}$, $N(R^{13})_2$, $COOR^{13}$, $C(O)N(R^{13})_2$, $SR^{13}$, $SO_2R^{13}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^{13})$, wherein said $C_1$-$C_6$ alkyl, $C_2$-$C_6$ haloalkyl, $C_2$-$C_6$ alkenyl, $C_2$-$C_6$ haloalkenyl; and Q' is selected from the group consisting of:

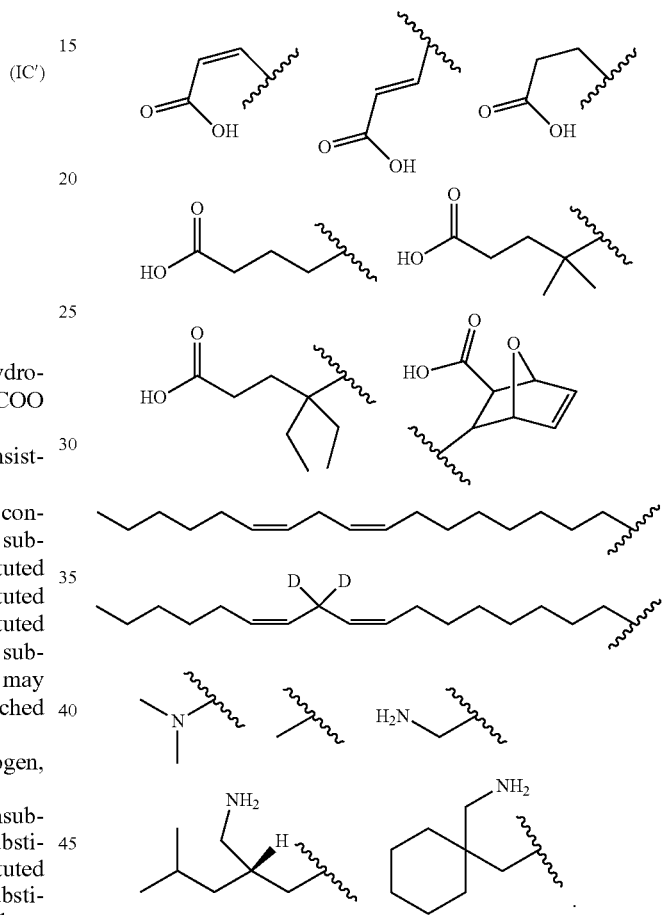

In an embodiment, the present application includes a compound of Formula (ID), (1E), (IF) and (IG) or a pharmaceutically acceptable salt, solvate or prodrug thereof:

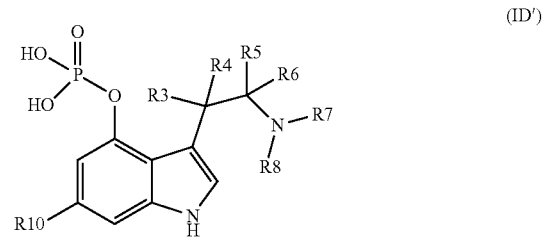

(ID')

-continued

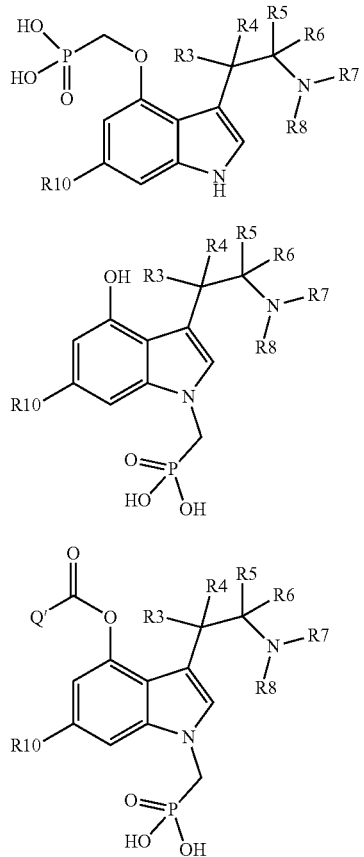

R³ to R⁶ are independently selected from the group consisting of hydrogen and deuterium;

R⁷ and R⁸ are independently selected from the group consisting of hydrogen, deuterium, lower alkyl and lower deuterated alkyl;

R¹⁰ is selected from the group consisting of hydrogen, halogen, cyano and lower alkyl; and Q' is selected from the groups defined above.

In one embodiment, the compounds of general formula (I), and pharmaceutically acceptable salts of the foregoing, the compounds are isotopically enriched with deuterium. In aspects of these embodiments, one or more of $R^3$, $R^4$, $R^5$, $R^6$, $R^7$, $R^8$ and $R^{10}$ may include deuterium;

In one embodiment, the compounds of general formula (I), and pharmaceutically acceptable salts of the foregoing, the compounds are isotopically enriched with deuterium. In aspects of these embodiments, one or more of $R^1$, $R^2$, $R^3$, $R^4$, $R^5$, $R^6$, $R^7$, $R^8$, $R^9$, $R^{10}$, $R^{11}$, $R^{12}$ and $R^{13}$ may include deuterium.

In one embodiment, the compounds of general formula (I), and pharmaceutically acceptable salts of the foregoing, the compounds are isotopically enriched with deuterium. In aspects of these embodiments, one or more of $R^3$, $R^4$, $R^5$, $R^6$, $R^7$, $R^8$ and $R^{10}$ may include deuterium.

In an embodiment, the compound of the present application is selected from the compounds of Examples 1 to 42 as illustrated below or a pharmaceutically acceptable salt, solvate and/or prodrug thereof:

TABLE 1

Representative compounds of compound of Formula (I).

| Compound ID # | Chemical Structure | IUPAC Name | Chemical Formula/ Molecular Weight |
|---|---|---|---|
| I-1 | 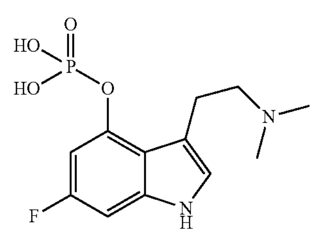 [SMILES: CN(C)CCc1c[nH]c2cc(F)cc(OP(=O)(O)O)c12] | 3-(2-(dimethylamino)ethyl)-6-fluoro-1H-indol-4-yl dihydrogen phosphate | C12H16FN2O4P 302.24 |
| I-2 | 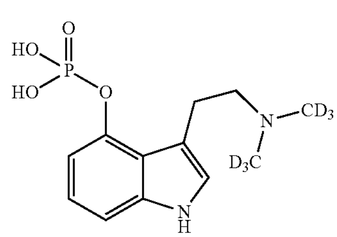 [SMILES: [2H]C([2H])([2H])N(CCc1c[nH]c2cccc(OP(=O)(O)O)c12)C([2H])([2H])[2H]] | 3-(2-(bis(methyl-d3)amino)ethyl)-1H-indol-4-yl dihydrogen phosphate | C12H11D6N2O4P 290.29 |

TABLE 1-continued

Representative compounds of compound of Formula (I).

| Compound ID # | Chemical Structure | IUPAC Name | Chemical Formula/ Molecular Weight |
|---|---|---|---|
| I-3 | 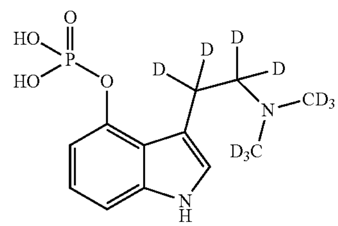 [SMILES: [2H]C([2H])([2H])N(C([2H])([2H])[2H])C([2H])([2H])C([2H])([2H])c1c[nH]c2cccc(OP(=O)(O)O)c12] | 3-(2-(bis(methyl-d3)amino)ethyl-1,1,2,2-d4)-1H-indol-4-yl dihydrogen phosphate | C12H7D10N2O4P 294.31 |
| I-4 | 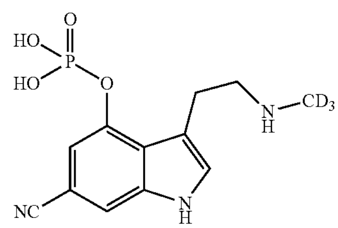 [SMILES: [2H]C([2H])([2H])NCCc1c[nH]c2cc(C#N)cc(OP(=O)(O)O)c12] | 6-cyano-3-(2-((methyl-d3)amino)ethyl)-1H-indol-4-yl dihydrogen phosphate | C12H11D3N3O4P 298.25 |
| I-5 | 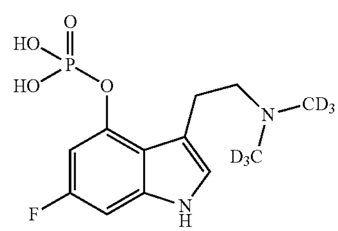 [SMILES: [2H]C([2H])([2H])N(CCc1c[nH]c2cc(F)cc(OP(=O)(O)O)c12)C([2H])([2H])[2H]] | 3-(2-(bis(methyl-d3)amino)ethyl)-6-fluoro-1H-indol-4-yl dihydrogen phosphate | C12H10D6FN2O4P 308.28 |
| I-6 | 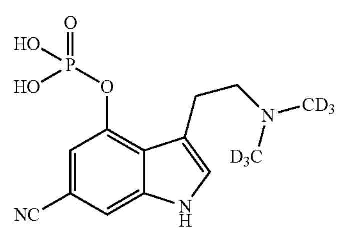 [SMILES: [2H]C([2H])([2H])N(CCc1c[nH]c2cc(C#N)cc(OP(=O)(O)O)c12)C([2H])([2H])[2H]] | 3-(2-(bis(methyl-d3)amino)ethyl)-6-cyano-1H-indol-4-yl dihydrogen phosphate | C13H10D6N3O4P 315.30 |
| I-7 | 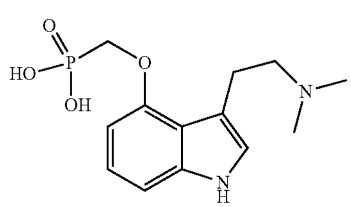 [SMILES: CN(C)CCc1c[nH]c2cccc(OCP(=O)(O)O)c12] | (((3-(2-(dimethylamino)ethyl)-1H-indol-4-yl)oxy)methyl)phosphonic acid | C13H19N2O4P 298.28 |
| I-8 | 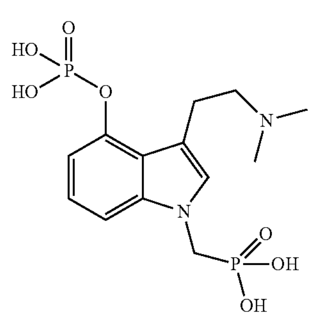 [SMILES: CN(C)CCc1cn(CP(=O)(O)O)c2cccc(OP(=O)(O)O)c12] | ((3-(2-(dimethylamino)ethyl)-4-(phosphonooxy)-1H-indol-1-yl)methyl)phosphonic acid | C13H20N2O7P2 378.26 |

TABLE 1-continued

Representative compounds of compound of Formula (I).

| Compound ID # | Chemical Structure | IUPAC Name | Chemical Formula/ Molecular Weight |
|---|---|---|---|
| I-9 | 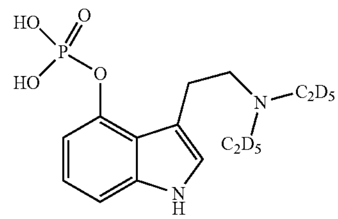 | 3-(2-(bis(methyl-d6)amino)ethyl)-1H-indol-4-yl dihydrogen phosphate | C14H11D10N2O4P 322.37 |
| I-10 | 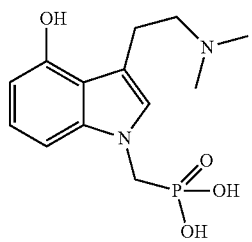 [SMILES: CN(C)CCc1cn(CP(=O)(O)O)c2cccc(O)c12] | ((3-(2-(dimethylamino)ethyl)-4-hydroxy-1H-indol-1-yl)methyl)phosphonic acid de | C13H19N2O4P: 298.28 |
| I-11 | 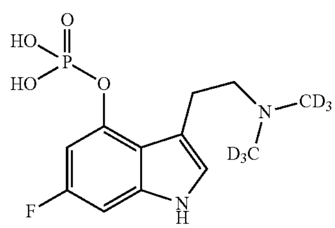 [SMILES: [2H]C([2H])([2H])N(CCc1c[nH]c2cc(F)cc(OP(=O)(O)O)c12)C([2H])([2H])[2H]] | 3-(2-(bis(methyl-d6)amino)ethyl)-6-fluoro-1H-indol-4-yl dihydrogen phosphate | C12H10D6FN2O4P 308.28 |
| I-12 | 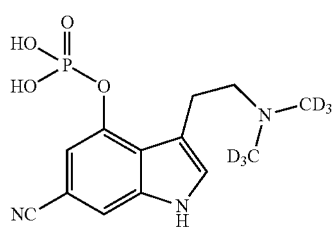 [SMILES: [2H]C([2H])([2H])N(CCc1c[nH]c2cc(C#N)cc(OP(=O)(O)O)c12)C([2H])([2H])[2H]] | 3-(2-(bis(methyl-d3)amino)ethyl)-6-cyano-1H-indol-4-yl dihydrogen phosphate | C13H10D6N3O4P 315.30 |
| I-13 | 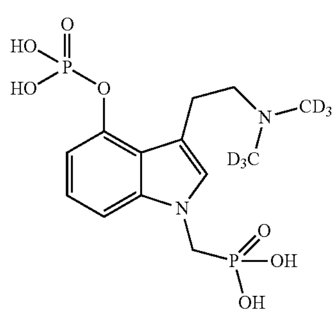 [SMILES: [2H]C([2H])([2H])N(CCc1cn(CP(=O)(O)O)c2cccc(OP(=O)(O)O)c12)C([2H])([2H])[2H]] | ((3-(2-(bis(methyl-d3)amino)ethyl)-4-(phosphonooxy)-1H-indol-1-yl)methyl)phosphonic acid | C13H14D6N2O7P2 384.29 |
| I-14 | 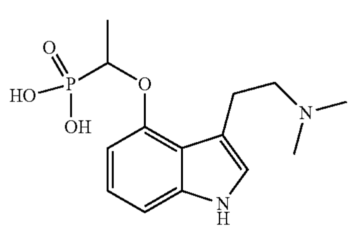 [SMILES: CC(Oc1cccc2[nH]cc(CCN(C)C)c12)P(=O)(O)O] | (1-((3-(2-(dimethylamino)ethyl)-1H-indol-4-yl)oxy)ethyl) phosphonic acid | C14H21N2O4P 312.31 |

TABLE 1-continued

Representative compounds of compound of Formula (I).

| Compound ID # | Chemical Structure | IUPAC Name | Chemical Formula/ Molecular Weight |
|---|---|---|---|
| I-15 | 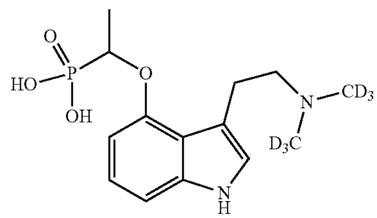 [SMILES: [2H]C([2H])([2H])N(CCc1c[nH]c2cccc(OC(C)P(=O)(O)O)c12)C([2H])([2H])[2H]] | (1-((3-(2-(bis(methyl-d3)amino)ethyl)-1H-indol-4-yl)oxy)ethyl) phosphonic acid | C14H15D6N2O4P 318.34 |
| I-16 | 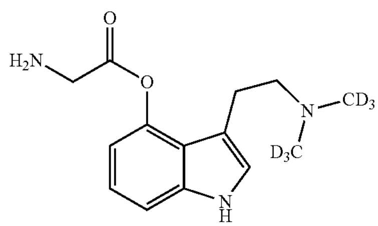 [SMILES: [2H]C([2H])([2H])N(CCc1c[nH]c2cccc(OC(=O)CN)c12)C([2H])([2H])[2H]] | 3-(2-(bis(methyl-d3)amino)ethyl)-1H-indol-4-yl glycinate | C14H13D6N3O2 267.36 |
| I-17 | 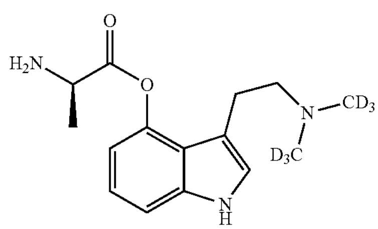 [SMILES: [2H]C([2H])([2H])N(CCc1c[nH]c2cccc(OC(=O)[C@@H](C)N)c12)C([2H])([2H])[2H]] | 3-(2-(bis(methyl-d3)amino)ethyl)-1H-indol-4-yl D-alaninate | C15H15D6N3O2 281.39 |
| I-18 | 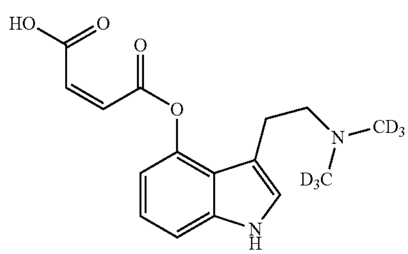 [SMILES: [2H]C([2H])([2H])N(CCc1c[nH]c2cccc(OC(=O)/C=C\C(=O)O)c12)C([2H])([2H])[2H]] | (Z)-4-((3-(2-(bis(methyl-d3)amino)ethyl)-1H-indol-4-yl)oxy)-4-oxobut-2-enoic acid | C16H12D6N2O4 308.37 |
| I-19 | 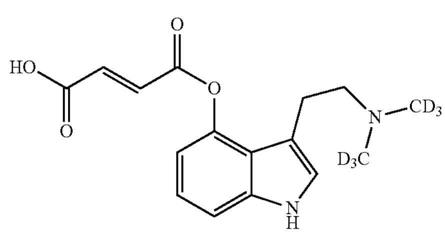 [SMILES: [2H]C([2H])([2H])N(CCc1c[nH]c2cccc(OC(=O)/C=C/C(=O)O)c12)C([2H])([2H])[2H]] | (E)-4-((3-(2-(bis(methyl-d3)amino)ethyl)-1H-indol-4-yl)oxy)-4-oxobut-2-enoic acid | C16H12D6N2O4 308.37 |
| I-20 | 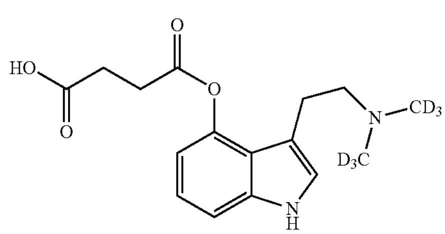 [SMILES: [2H]C([2H])([2H])N(CCc1c[nH]c2cccc(OC(=O)CCC(=O)O)c12)C([2H])([2H])[2H]] | 4-((3-(2-(bis(methyl-d3)amino)ethyl)-1H-indol-4-yl)oxy)-4-oxobutanoic acid | C16H14D6N2O4 310.38 |

TABLE 1-continued

Representative compounds of compound of Formula (I).

| Compound ID # | Chemical Structure | IUPAC Name | Chemical Formula/ Molecular Weight |
|---|---|---|---|
| I-21 | 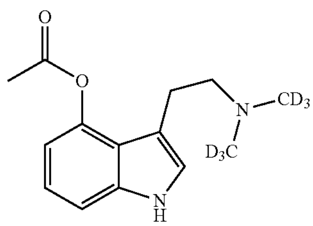 [SMILES: [2H]C([2H])([2H])N(CCc1c[nH]c2cccc(OC(C)=O)c12)C([2H])([2H])[2H]] | 3-(2-(bis(methyl-d3)amino)ethyl)-1H-indol-4-yl acetate | C14H12D6N2O2 252.35 |
| I-22 | 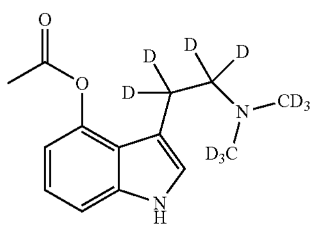 [SMILES: [2H]C([2H])([2H])N(C([2H])([2H])[2H])C([2H])([2H])C([2H])([2H])c1c[nH]c2cccc(OC(C)=O)c12] | 3 3-(2-(bis(methyl-d3)amino)ethyl-1,1,2,2-d4)-1H-indol-4-yl acetate | C14H8D10N2O2 256.37 |
| I-23 | 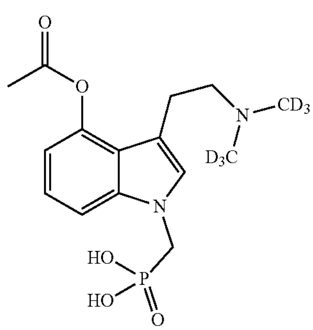 [SMILES: [2H]C([2H])([2H])N(CCc1cn(CP(=O)(O)O)c2cccc(OC(C)=O)c12)C([2H])([2H])[2H]] | ((4-acetoxy-3-(2-(bis(methyl-d3)amino)ethyl)-1H-indol-1-yl)methyl)phosphonic acid | C15H15D6N2O5P 346.35 |
| I-24 | | 3-(2-(dimethylamino)ethyl)-1H-indol-4-yl (9Z,12Z)-octadeca-9,12-dienoate | C30H46N2O2 466.71 |

TABLE 1-continued

Representative compounds of compound of Formula (I).

| Compound ID # | Chemical Structure | IUPAC Name | Chemical Formula/ Molecular Weight |
|---|---|---|---|
| 1-25 | 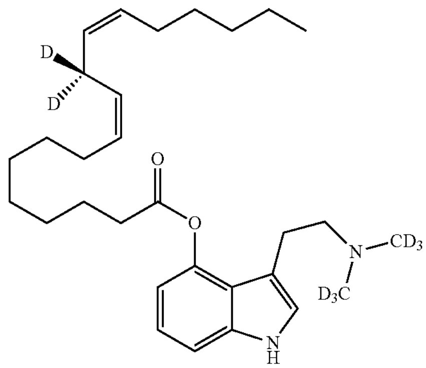 | 3-(2-(d6-dimethylamino)ethyl)-1H-indol-4-yl (9Z,12Z)-octadeca-9,12-dienoate-11,11-d2 | C30H38D8N2O2: 474.76 |
| 1-26 | 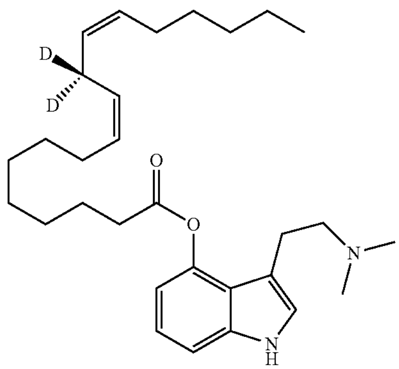 | 3-(2-(dimethylamino)ethyl)-1H-indol-4-yl (9Z,12Z)-octadeca-9,12-dienoate-11,11-d2 | C30H44D2N2O2 468.72 |
| 1-27 | 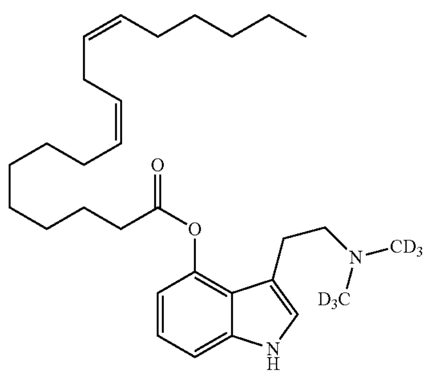 [SMILES: [2H]C([2H])([2H])N(CCc1c[nH]c2cccc(OC(=O)CCCCCCC/C=C\C/C=C\CCCCC)c12)C([2H])([2H])[2H]] | 3-(2-(bis(methyl-d3)amino)ethyl)-1H-indol-4-yl (9Z,12Z)-octadeca-9,12-dienoate | C30H40D6N2O2 472.75 |
| 1-28 | 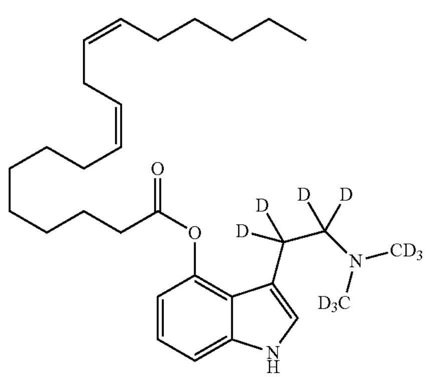 [SMILES: [2H]C([2H])([2H])N(C([2H])([2H])[2H])C([2H])([2H])C([2H])([2H])c1c[nH]c2cccc(OC(=O)CCCCCCC/C=C\C/C=C\CCCCC)c12] | 3-(2-(bis(methyl-d3)amino)ethyl-1,1,2,2-d4)-1H-indol-4-yl (9Z,12Z)-octadeca-9,12-dienoate | C30H36D10N2O2 476.77 |

TABLE 1-continued

Representative compounds of compound of Formula (I).

| Compound ID # | Chemical Structure | IUPAC Name | Chemical Formula/ Molecular Weight |
|---|---|---|---|
| I-29 | 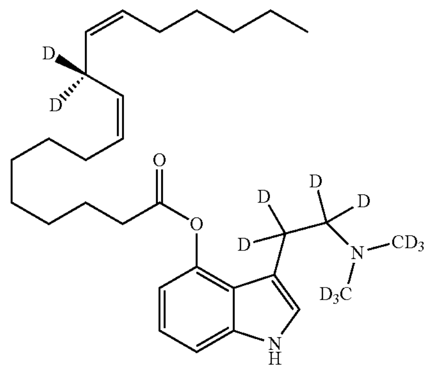 | 3-(2-(bis(methyl-d6)amino)ethyl-1,1,2,2-d4)-1H-indol-4-yl (9Z,12Z)-octadeca-9,12-dienoate-11,11-d2 | C30H34D12N2O2: 478.78 |
| I-30 | 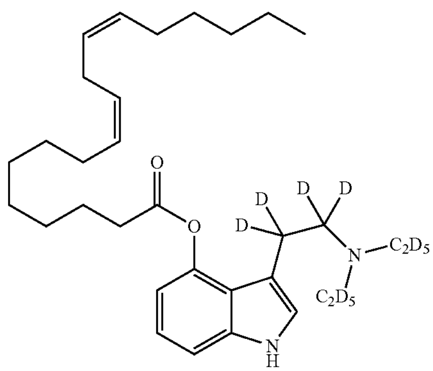 | 3-(2-(d10-diethylamino)ethyl-d4)-1H-indol-4-yl (9Z,12Z)-octadeca-9,12-dienoate | C32H36D14N2O2 508.85 |
| I-31 | | 3-(2-(d10-diethylamino)ethyl-d4)-1H-indol-4-yl (9Z,12Z)-octadeca-9,12-dienoate-11,11-d2 | C32H34D16N2O2 510.86 |
| I-32 | | 3-(2-(diethylamino)ethyl-d4)-1H-indol-4-yl (9Z,12Z)-octadeca-9,12-dienoate | C32H46D4N2O2 498.79 |

TABLE 1-continued

Representative compounds of compound of Formula (I).

| Compound ID # | Chemical Structure | IUPAC Name | Chemical Formula/ Molecular Weight |
|---|---|---|---|
| 1-33 | 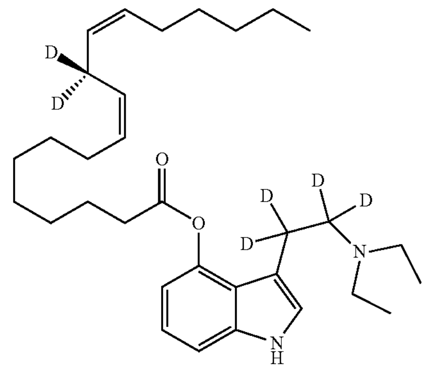 | 3-(2-(diethylamino)ethyl-d4)-1H-indol-4-yl (9Z,12Z)-octadeca-9,12-dienoate-11,11-d2 | C32H44D6N2O2 500.80 |
| 1-34 | 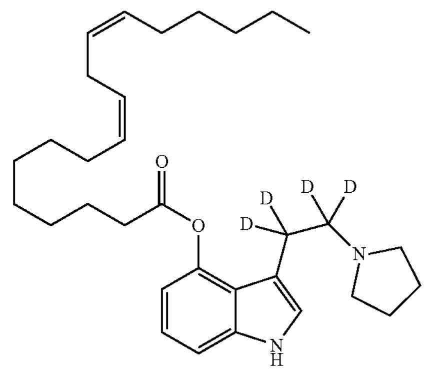 [SMILES: [2H]C([2H])(c1c[nH]c2cccc(OC(=O)CCCCCCC/C=C\C/C=C\CCCCC)c12)C([2H])([2H])N1CCCC1] | 3-(2-(pyrrolidin-1-yl)ethyl-1,1,2,2-d4)-1H-indol-4-yl (9Z,12Z)-octadeca-9,12-dienoate | C32H44D4N2O2 Exact Mass: 496.40 Molecular Weight: 496.77 |
| 1-35 | 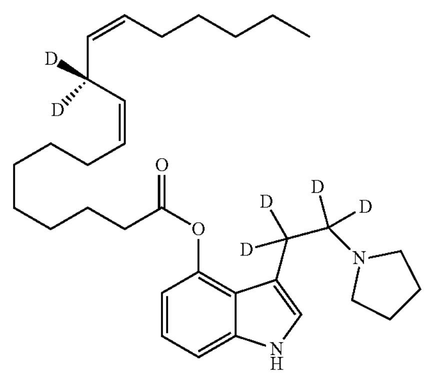 | 3-(2-(pyrrolidin-1-yl)ethyl-1,1,2,2-d4)-1H-indol-4-yl (9Z,12Z)-octadeca-9,12-dienoate-11,11-d2 | C32H42D6N2O2 498.78 |
| 1-36 | 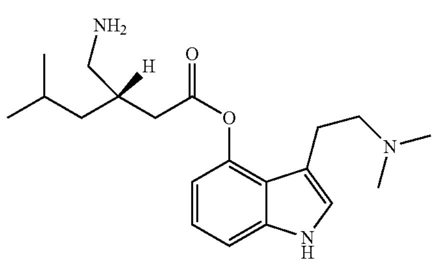 [SMILES: CC(C)C[C@H](CN)CC(=O)Oc1cccc2[nH]cc(CCN(C)C)c12] | 3-(2-(dimethylamino)ethyl)-1H-indol-4-yl (S)-3-(aminomethyl)-5-methylhexanoate | C20H31N3O2 345.49 |

TABLE 1-continued

Representative compounds of compound of Formula (I).

| Compound ID # | Chemical Structure | IUPAC Name | Chemical Formula/ Molecular Weight |
|---|---|---|---|
| 1-37 | 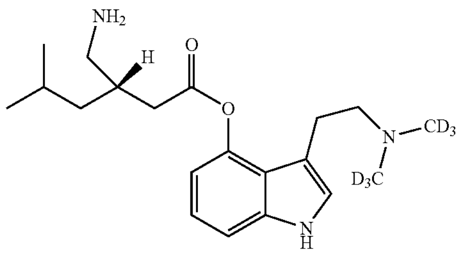 [SMILES: [2H]C([2H])([2H])N(CCc1c[nH]c2cccc(OC(=O)C[C@@H](CN)CC(C)C)c12)C([2H])([2H])[2H]] | 3-(2-(bis(methyl-d3)amino)ethyl)-1H-indol-4-yl (S)-3-(aminomethyl)-5-methylhexanoate | C20H25D6N3O2 351.52 |
| 1-38 | 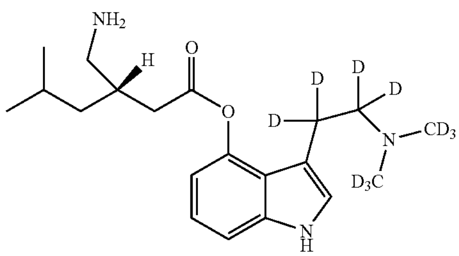 [SMILES: [2H]C([2H])([2H])N(C([2H])([2H])[2H])C([2H])([2H])C([2H])([2H])c1c[nH]c2cccc(OC(=O)C[C@@H](CN)CC(C)C)c12] | 3-(2-(bis(methyl-d3)amino)ethyl-1,1,2,2-d4)-1H-indol-4-yl (S)-3-(aminomethyl)-5-methylhexanoate | C20H21D10N3O2 355.55 |
| 1-39 | 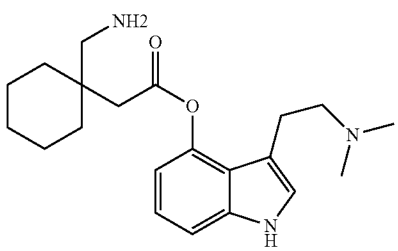 [SMILES: CN(C)CCc1c[nH]c2cccc(OC(=O)CC3(CN)CCCCC3)c12] | 3-(2-(dimethylamino)ethyl)-1H-indol-4-yl 2-(1-(aminomethyl)cyclohexyl)acetate | C21H31N3O2 357.50 |
| 1-40 | 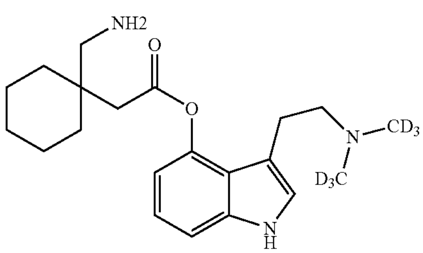 [SMILES: [2H]C([2H])([2H])N(CCc1c[nH]c2cccc(OC(=O)CC3(CN)CCCCC3)c12)C([2H])([2H])[2H]] | 3-(2-(bis(methyl-d3)amino)ethyl)-1H-indol-4-yl 2-(1-(aminomethyl)cyclohexyl)acetate | C21H25D6N3O2 363.53 |
| 1-41 | 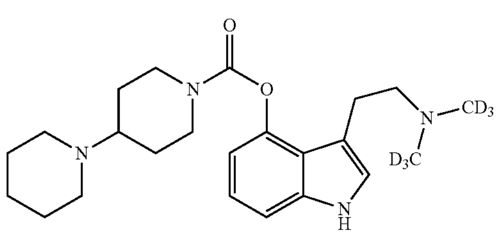 [SMILES: [2H]C([2H])([2H])N(CCc1c[nH]c2cccc(OC(=O)N3CCC(N4CCCCC4)CC3)c12)C([2H])([2H])[2H]] | 3-(2-(bis(methyl-d3)amino)ethyl)-1H-indol-4-yl [1,4'-bipiperidine]-1'-carboxylate | C23H28D6N4O2 404.59 |
| 1-42 | 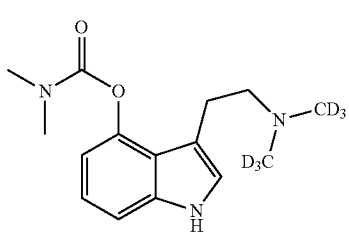 [SMILES: [2H]C([2H])([2H])N(CCc1c[nH]c2cccc(OC(=O)N(C)C)c12)C([2H])([2H])[2H]] | 3-(2-(bis(methyl-d3)amino)ethyl)-1H-indol-4-yl dimethylcarbamate | C15H15D6N3O2 281.39 |

Compounds that may be used in the compositions and methods described herein include any compound having the structure of Formula (I):

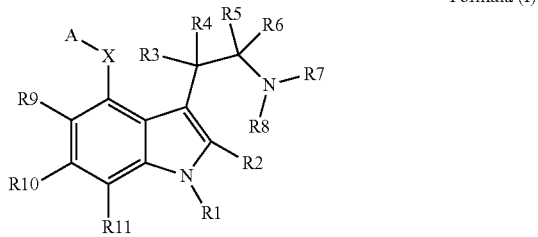

Formula (I)

or pharmaceutically acceptable salts thereof, as described herein. Uses of compounds of general formula (I) and processes for making compounds of general formula (I) are also disclosed.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), and Handbook of Pharmaceutical Salts. Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, abutyl amine, choline, and salts with amino acids such as arginine, lysine and the like. Basic nitrogen containing groups may be quartemized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention. In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

In some embodiments, the compounds of the present application can also include tautomeric forms, such as keto-enol tautomers and the like. Tautomeric forms can be in equilibrium or sterically locked into one form by appropriate substitution. It is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The compounds of the present application may further be radiolabeled and accordingly all radiolabeled versions of the compounds of the application are included within the scope of the present application. The compounds of the application also include those in which one or more radioactive atoms are incorporated within their structure.

III. Compositions

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of any of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, insufflation, epidurally, nasal, rectal, vaginal, patch, pump, minipump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate), or solvents (e.g. medium chain triglycerides, ethanol, water). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers, solvents or diluents include lactose, medium chain triglycerides, ethanol and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., medium chain triglycerides, almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiments, such compositions include mucomimetics such as hyaluronic acid, chondroitin sulfate, hydroxypropyl methylcellulose or polyvinyl alcohol, preservatives such as sorbic acid, EDTA or benzyl chromium chloride and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, Pa., 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts, solvates and/or prodrugs thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient and from about 1 wt % to about 99.95 wt % or about 30 wt % to about 99.90 wt % of a pharmaceutically acceptable carrier, all percentages by weight being based on the total composition.

In an embodiment of the application, compositions are formulated for oral administration and the one or more compounds are suitably in the form of tablets containing 0.1, 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet.

In the above, the term "a compound" also includes embodiments wherein one or more compounds are referenced.

In some embodiments, the compounds of the application including pharmaceutically acceptable salts, solvates and/or prodrugs thereof are used are administered in a composition comprising an additional therapeutic agent. Therefore the present application also includes a pharmaceutical composition comprising one of more compounds of the application, or pharmaceutically acceptable salts, solvates and/or prodrugs thereof and an additional therapeutic agent, and optionally one or more pharmaceutically acceptable excipients. In some embodiments, the additional therapeutic agent is another known agent useful for treatment of a disease, disorder or condition by activation of a serotonin receptor, for example those listed in the Methods and Uses section below. In some embodiments, the additional therapeutic agent is a psychoactive drug.

In the above, the term "a compound" also includes embodiments wherein one or more compounds are referenced.

IV. Methods and Uses of the Application

The compounds of the application are serotonergic binding agents that act as agonists or partial agonists at a serotonin receptor.

Accordingly, the present application includes a method for activating a serotonin receptor in a cell, either in a biological sample or in a patient, comprising administering an effective amount of one or more compounds of the application to the cell. The application also includes a use of one or more compounds of the application for activating a serotonin receptor in a cell as well as a use of one or more compounds of the application for the preparation of a medicament for activating a serotonin receptor in a cell. The application further includes one or more compounds of the application for use in activating a serotonin receptor in a cell.

As the compounds of the application are capable of activating a serotonin receptor, the compounds of the application are useful for treating diseases, disorders or conditions by activating a serotonin receptor. Therefore, the compounds of the present application are useful as medicaments. Accordingly, the application also includes a compound of the application for use as a medicament.

The present application also includes a method of treating a disease, disorder or condition by activation of a serotonin receptor comprising administering a therapeutically effective amount of one or more compounds of the application to a subject in need thereof.

The present application also includes a use of one or more compounds of the application for treatment of a disease, disorder or condition by activation of a serotonin receptor as well as a use of one or more compounds of the application for the preparation of a medicament for treatment of a disease, disorder or condition by activation of a serotonin receptor. The application further includes one or more compounds of the application for use in treating a disease, disorder or condition by activation of a serotonin receptor.

In some embodiments, the serotonin receptor is $5\text{-HT}_{2A}$. Accordingly, the present application includes a method for activating $5\text{-HT}_{2A}$ in a cell, either in a biological sample or in a patient, comprising administering an effective amount of one or more compounds of the application to the cell. The application also includes a use of one or more compounds of the application for activating 5-HT$_{2A}$ in a cell as well as a use of one or more compounds of the application for the preparation of a medicament for activating 5-HT$_{2A}$ in a cell. The application further includes one or more compounds of the application for use in activating 5-HT$_{2A}$ in a cell.

The present application also includes a method of treating a disease, disorder or condition by activation of 5-HT$_{2A}$ comprising administering a therapeutically effective amount of one or more compounds of the application to a subject in need thereof. The present application also includes a use of one or more compounds of the application for treatment of a disease, disorder or condition by activation of 5-HT$_{2A}$ as well as a use of one or more compounds of the application for the preparation of a medicament for treatment of a disease, disorder or condition by activation of 5-HT$_{2A}$. The application further includes one or more compounds of the application for use in treating a disease, disorder or condition by activation of 5-HT$_{2A}$.

In some embodiments, the compounds of the application are useful for preventing, treating and/or reducing the severity of a mental illness disorder and/or condition in a subject. Therefore, in some embodiments, the disease, disorder or condition that is treated by activation of a serotonin receptor is a mental illness. Accordingly, the present application also includes a method of treating a mental illness comprising administering a therapeutically effective amount of one or more compounds of the application to a subject in need thereof. The present application also includes a use of one or more compounds of the application for treatment a mental illness, as well as a use of one or more compounds of the application for the preparation of a medicament for treatment of a mental illness. The application further includes one or more compounds of the application for use in treating a mental illness.

In some embodiments, the mental illness is selected from anxiety disorders such as generalized anxiety disorder, panic disorder, social anxiety disorder and specific phobias; depression such as, hopelessness, loss of pleasure, fatigue and suicidal thoughts; mood disorders, such as depression, bipolar disorder, cancer-related depression, anxiety and cyclothymic disorder; psychotic disorders, such as hallucinations, delusions, schizophrenia; impulse control and addiction disorders, such as pyromania (starting fires), kleptomania (stealing) and compulsive gambling; alcohol addiction; drug addiction, such as opioid addiction; personality disorders, such as antisocial personality disorder, obsessive-compulsive personality disorder and paranoid personality disorder; obsessive-compulsive disorder (OCD), such as thoughts or fears that cause a subject to perform certain rituals or routines; post-traumatic stress disorder (PTSD); stress response syndromes (formerly called adjustment disorders); dissociative disorders, formerly called multiple personality disorder, or "split personality," and depersonalization disorder; factitious disorders; sexual and gender disorders, such as sexual dysfunction, gender identity disorder and the paraphilia's; somatic symptom disorders, formerly known as a psychosomatic disorder or somatoform disorder; and combinations thereof.

In some embodiments, the disease, disorder or condition that is treated by activation of a serotonin receptor comprises cognitive impairment; ischemia including stroke; neurodegeneration; refractory substance use disorders; sleep disorders; pain, such as social pain, acute pain, cancer pain, chronic pain, breakthrough pain, bone pain, soft tissue pain, nerve pain, referred pain, phantom pain, neuropathic pain, cluster headaches and migraine; obesity and eating disorders; epilepsies and seizure disorders; neuronal cell death; excitotoxic cell death; or a combination thereof.

In some embodiments, the mental illness is selected from hallucinations and delusions and a combination thereof.

In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations and chronoceptive hallucinations, and a combination thereof.

In some embodiments, the disease, disorder or condition that is treated by activation of a serotonin receptor is psychosis or psychotic symptoms. Accordingly, the present application also includes a method of treating psychosis or psychotic symptoms comprising administering a therapeutically effective amount of one or more compounds of the application to a subject in need thereof.

The present application also includes a use of one or more compounds of the application for treatment of psychosis or psychotic symptoms, as well as a use of one or more compounds of the application for the preparation of a medicament for treatment of psychosis or psychotic symptoms. The application further includes one or more compounds of the application for use in treating psychosis or psychotic symptoms.

In some embodiments, administering to said subject in need thereof a therapeutically effective amount of the compounds of the application does not result in a worsening of psychosis or psychotic symptoms such as, but not limited to, hallucinations and delusions. In some embodiments, administering to said subject in need thereof a therapeutically effective amount of the compounds of the application results in an improvement of psychosis or psychotic symptoms such as, but not limited to, hallucinations and delusions. In some embodiments, administering to said subject in need thereof a therapeutically effective amount of the compounds of the application results in an improvement of psychosis or psychotic symptoms.

In some embodiments, the compounds of the application are useful for treating a central nervous system (CNS) disease, disorder or condition and/or a neurological disease, disorder or condition in a subject in need of therapy, comprising administering a therapeutically effective amount of a compound of general formula (I), or a pharmaceutically acceptable salt thereof to the subject.

Therefore, in some embodiments, the disease, disorder or condition that is treated by activation of a serotonin receptor is a central nervous system (CNS) disease, disorder or condition and/or a neurological disease, disorder or condition. Accordingly, the present application also includes a method of treating a CNS disease, disorder or condition and/or a neurological disease, disorder or condition comprising administering a therapeutically effective amount of one or more compounds of the application to a subject in need thereof. The present application also includes a use of one or more compounds of the application for treatment a CNS disease, disorder or condition and/or a neurological disease, disorder or condition, as well as a use of one or more compounds of the application for the preparation of a medicament for treatment of a CNS disease, disorder or condition and/or a neurological disease, disorder or condition. The application further includes one or more compounds of the application for use in treating a CNS disease, disorder or condition and/or a neurological disease, disorder or condition.

In some embodiments the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-ontological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa ("AN") and bulimia nervosa ("BN"); and binge eating disorder ("BED"), trichotillomania, dermotillomania, nail biting; migraine; fibromyalgia; and peripheral neuropathy of any etiology, and combinations thereof.

In another embodiment, the compounds general formula (I) are directed towards a method for preventing, treating, and/or reducing the severity of a mental illness disorder and/or condition in a subject. For example, the illness disorder comprises anxiety disorders include generalized anxiety disorder, panic disorder, social anxiety disorder, and specific phobias; depression such as, hopelessness, loss of pleasure, fatigue, and suicidal thoughts; mood disorders, such as depression, bipolar disorder, cancer-related depression, anxiety, and cyclothymic disorder; psychotic disorders, such as hallucinations and delusions, schizophrenia; eating disorders e.g. anorexia nervosa, bulimia nervosa, and binge eating disorder; impulse control and addiction disorders e.g. Pyromania (starting fires), kleptomania (stealing), and compulsive gambling; alcohol addiction; drug addiction including opioid addiction; personality disorders include antisocial personality disorder, obsessive-compulsive personality disorder, and paranoid personality disorder; obsessive-compulsive disorder (OCD) e.g. thoughts or fears that cause them to perform certain rituals or routines; post-traumatic stress disorder (PTSD); stress response syndromes (formerly called adjustment disorders); dissociative disorders, formerly called multiple personality disorder, or "split personality," and depersonalization disorder are examples of dissociative disorders; factitious disorders; sexual and gender disorders e.g. sexual dysfunction, gender identity disorder, and the paraphilia's; somatic symptom disorders, formerly known as a psychosomatic disorder or somatoform disorder; attentional disorders including attentional deficit disorder, attentional deficit hyperactivity disorder and attentional deficits seen in other disorders included here; tic disorders: People with tic disorders such as, Tourette's syndrome; and other diseases or conditions, including various sleep-related problems and many forms of dementia, including Alzheimer's disease, Lewy body dementia, Parkinson's disease dementia and frontotemporal dementia. In embodiments, the condition comprises cognitive impairment, ischemia including stroke, neurodegeneration, refractory substance use disorders, sleep disorders, pain, e.g. surgical pain, social pain, acute pain, cancer pain, chronic pain, breakthrough pain, bone pain, soft tissue pain, nerve pain, referred pain, phantom pain, neuropathic pain, cluster headaches and migraine, obesity and eating disorders, epilepsies and seizure disorders, neuronal cell death, excitotoxic cell death, or a combination thereof.

In yet another embodiment relates to methods of treating a CNS disorder in a patient in need of therapy, comprising administering a therapeutically effective amount of a compound of general formula (I), or a pharmaceutically acceptable salt thereof to the patient. In aspects of this embodiment, CNS disorder is, but not limited to mental illness disorders above;

In some embodiments, the subject is a mammal. In another embodiment, the subject is human. In some embodiments, the subject is a non-human animal. In some embodiments, the subject is canine. In some embodiments, the subject is feline. Accordingly, the compounds, methods and uses of the present application are directed to both human and veterinary diseases, disorders and conditions.

In some embodiments, the compounds of the application are useful for treating behavioral problems in subjects that are felines or canines.

Therefore, in some embodiments, the disease, disorder or condition that is treated by activation of a serotonin receptor is behavioral problems in subjects that are felines or canines. Accordingly, the present application also includes a method of treating a behavioral problem comprising administering a therapeutically effective amount of one or more compounds of the application to a non-human subject in need thereof. The present application also includes a use of one or more compounds of the application for treatment a behavioral problem in a non-human subject, as well as a use of one or more compounds of the application for the preparation of a medicament for treatment of a behavioral problem in a non-human subject. The application further includes one or more compounds of the application for use in treating a behavioral problem in a non-human subject.

In some embodiments, the behavioral problems are selected from, but are not limited to, anxiety, fear, stress, sleep disturbances, cognitive dysfunction, aggression, excessive noise making, scratching, biting and a combination thereof.

In some embodiments, the non-human subject is canine. In some embodiments, the non-human subject is feline.

The present application also includes a method of treating a disease, disorder or condition by activation of a serotonin receptor comprising administering a therapeutically effective amount of one or more compounds of the application in combination with another known agent useful for treatment of a disease, disorder or condition by activation of a serotonin receptor to a subject in need thereof. The present application also includes a use of one or more compounds of the application in combination with another known agent useful for treatment of a disease, disorder or condition by activation of a serotonin receptor for treatment of a disease, disorder or condition by activation of a serotonin receptor, as well as a use of one or more compounds of the application in combination with another known agent useful for treatment of a disease, disorder or condition by activation of a serotonin receptor for the preparation of a medicament for treatment of a disease, disorder or condition by activation of a serotonin receptor. The application further includes one or more compounds of the application in combination with another known agent useful for treatment of a disease, disorder or condition by activation of a serotonin receptor for use in treating a disease, disorder or condition by activation of a serotonin receptor.

In some embodiments, the disease, disorder or condition that is treated by activation of a serotonin receptor is a mental illness. In some embodiments, the disease, disorder or condition that is treated by activation of a serotonin receptor is a central nervous system (CNS) disease, disorder or condition and/or a neurological disease, disorder or condition. In some embodiments, the disease, disorder or condition that is treated by activation of a serotonin receptor is psychosis or psychotic symptoms. In some embodiments, the disease, disorder or condition that is treated by activation of a serotonin receptor is behavioral problems in a non-human subject.

In some embodiments, the disease, disorder or condition that is treated by activation of a serotonin receptor is a mental illness and the one or more compounds of the application are administered in combination with one or more additional treatments for a mental illness. In some embodiments, the additional treatments for a mental illness is selected from antipsychotics, including typical antipsychotics and atypical antipsychotics; antidepressants including selective serotonin reuptake inhibitors (SSRIs) and selective norepinephrine reuptake inhibitors (SNRIs), tricyclic antidepressants and monoamine oxidase inhibitors (MAOIs) (e.g. bupropion); anti-anxiety medication including benzodiazepines such as alprazolam; mood stabilizers such as lithium and anticonvulsants such carbamazepine, divalproex (valproic acid), lamotrigine, gabapentin and topiramate.

In some embodiments, the disease, disorder or condition that is treated by activation of a serotonin receptor is selected from attention deficit hyperactivity disorder and attention deficit disorder and a combination thereof. In some embodiments, the disease, disorder or condition that is treated by activation of a serotonin receptor is attention deficit hyperactivity disorder and/or attention deficit disorder and a combination thereof and the one or more compounds of the application are administered in combination with one or more additional treatments for attention deficit hyperactivity disorder and/or attention deficit disorder and a combination thereof. In some embodiments, the additional treatments for attention deficit hyperactivity disorder and/or attention deficit disorder and a combination thereof are selected from methylphenidate, atomoxetine and amphetamine and a combination thereof.

In some embodiments, the disease, disorder or condition that is treated by activation of a serotonin receptor is dementia or Alzheimer's disease and the one or more compounds of the application are administered in combination with one or more additional treatments for dementia or Alzheimer's disease. In some embodiments, the additional treatments for dementia and Alzheimer's disease are selected acetylcholinesterase inhibitors, NMDA antagonists and muscarinic agonists and antagonists, and nicotinic agonists.

In some embodiments, the acetylcholinesterase inhibitors are selected from donepezil, galantamine, rivastigmine, and phenserine, and combinations thereof.

In some embodiments, the NMDA antagonists are selected from MK-801, ketamine, phencyclidine, and memantine, and combinations thereof.

In some embodiments, the nicotinic agonists is nicotine, nicotinic acid, nicotinic alpha7 agonists or alpha2 beta4 agonists or combinations thereof.

In some embodiments, the muscarinic agonists is a muscarinic M1 agonist or a muscarinic M4 agonist, or combinations thereof.

In some embodiments, the muscarinic antagonist is a muscarinic M2 antagonist.

In some embodiments, the disease, disorder or condition that is treated by activation of a serotonin receptor is psychosis or psychotic symptoms and the one or more compounds of the application are administered in combination with one or more additional treatments for psychosis or psychotic symptoms. In some embodiments, the additional treatments for psychosis or psychotic symptom are selected typical antipsychotics and atypical antipsychotics.

In some embodiments, the typical antipsychotics are selected from acepromazine, acetophenazine, benperidol, bromperidol, butaperazine, carfenazine, chlorproethazine, chlorpromazine, chlorprothixene, clopenthixol, cyamemazine, dixyrazine, droperidol, fluanisone, flupentixol, fluphenazine, fluspirilene, haloperidol, levomepromazine, lenperone, loxapine, mesoridazine, metitepine, molindone, moperone, oxypertine, oxyprotepine, penfluridol, perazine, periciazine, perphenazine, pimozide, pipamperone, piperacetazine, pipotiazine, prochlorperazine, promazine, prothipendyl, spiperone, sulforidazine, thiopropazate, thioproperazine, thioridazine, thiothixene, timiperone, trifluoperazine, trifluperidol, triflupromazine and zuclopenthixol and combinations thereof.

In some embodiments, the atypical antipsychotics are selected from amoxapine, amisulpride, aripiprazole, asenapine, blonanserin, brexpiprazole, cariprazine, carpipramine, clocapramine, clorotepine, clotiapine, clozapine, iloperidone, levosulpiride, lurasidone, melperone, mosapramine, nemonapride, olanzapine, paliperidone, perospirone, quetiapine, remoxipride, reserpine, risperidone, sertindole, sulpiride, sultopride, tiapride, veralipride, ziprasidone and zotepine, and combinations thereof.

In some embodiments, the disease, disorder or condition that is treated by activation of a serotonin receptor is a mental illness and the one or more compounds of the application are administered in combination with one or more additional treatments for a mental illness. In some embodiments, the additional treatments for a mental illness is selected typical antipsychotics and atypical antipsychotics.

In some embodiments, effective amounts vary according to factors such as the disease state, age, sex and/or weight of the subject or species. In some embodiments, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated and the like, but can nevertheless be routinely determined by one skilled in the art.

In some embodiment, the compounds of the application are administered one, two, three or four times a year. In some embodiments, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 1, 2, 3, 4, 5 or 6 times daily. The length of the treatment period depends on a variety of factors, such as the severity of the disease, disorder or condition, the age of the subject, the concentration and/or the activity of the compounds of the application and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In some embodiments, the compounds of the application are administered at doses that are hallucinogenic or psychotomimetic and taken in conjunction with psychotherapy or therapy and may occur once, twice, three, or four times a year. However, in some embodiments, the compounds are administered to the subject once daily, once every two days, once every 3 days, once a week, once every two weeks, once a month, once every two months, or once every three months at doses that are not hallucinogenic or psychotomimetic.

A compound of the application is either used alone or in combination with other known agents useful for treating diseases, disorders or conditions by activation of a serotonin receptor, such as the compounds of the application. When used in combination with other known agents useful in treating diseases, disorders by activation of a serotonin receptor, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In some embodiments, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent and a pharmaceutically acceptable carrier.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any and the clearance rate of the compound in the subject to be treated. One of skill in the art can determine the appropriate dosage based on the above factors. In some embodiments, one or more compounds of the application are administered initially in a suitable dosage that is adjusted as required, depending on the clinical response. Dosages will generally be selected to maintain a serum level of the one or more compounds of the application from about 0.01 μg/cc to about 1000 μg/cc, or about 0.1 μg/cc to about 100 μg/cc. As a representative example, oral dosages of one or more compounds of the application will range between about 10 μg per day to about 1000 mg per day for an adult, suitably about 10 μg per day to about 500 mg per day, more suitably about 10 μg per day to about 200 mg per day. For parenteral administration, a representative amount is from about 0.0001 mg/kg to about 10 mg/kg, about 0.0001 mg/kg to about 1 mg/kg, about 0.01 mg/kg to about 0.1 mg/kg or about 0.0001 mg/kg to about 0.01 mg/kg will be administered. For oral administration, a representative amount is from about 0.001 μg/kg to about 10 mg/kg, about 0.1 μg/kg to about 10 mg/kg, about 0.01 μg/kg to about 1 mg/kg or about 0.1 μg/kg to about 1 mg/kg. For administration in suppository form, a representative amount is from about 0.1 mg/kg to about 10 mg/kg or about 0.1 mg/kg to about 1 mg/kg. In some embodiments of the application, compositions are formulated for oral administration and the one or more compounds are suitably in the form of tablets containing 0.1, 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient (one or more compounds of the application) per tablet. In some embodiments of the application the one or more compounds of the application are administered in a single daily, weekly or monthly dose or the total daily dose is divided into two, three or four daily doses.

In some embodiments, the compounds of the application are used or administered in an effective amount which comprises administration of doses or dosage regimens that are devoid of clinically meaningful psychedelic/psychotomimetic actions. In some embodiments, the compounds of the application are used or administered in an effective amount which comprises administration of doses or dosage regimens that provide clinical effects similar to those exhibited by a human plasma psilocin Cmax of 4 ng/mL or less and/or human 5-HT$_{2A}$ human CNS receptor occupancy of 40% or less or those exhibited by a human plasma psilocin Cmax of 1 ng/mL or less and/or human 5-HT$_{2A}$ human CNS receptor occupancy of 30% or less. In some embodiments, the compounds of the application are used or administered in an effective amount which comprises administration of doses or dosage regimens that provide clinical effects similar to those exhibited by a human plasma psilocin Tmax in excess of 60 minutes, in excess of 120 minutes or in excess of 180 minutes.

V. Preparation of Compounds

Compounds of the present application can be prepared by various synthetic processes. The choice of particular structural features and/or substituents may influence the selection of one process over another. The selection of a particular process to prepare a given compound of the application is within the purview of the person of skill in the art. Some starting materials for preparing compounds of the present application are available from commercial chemical sources or may be extracted from cells, plants, animals or fungi. Other starting materials, for example as described below, are readily prepared from available precursors using straightforward transformations that are well known in the art. In the Schemes below showing some embodiments of methods of preparation of compounds of the application, all variables are as defined in Formula (I), unless otherwise stated.

In some embodiments of the application, the compounds of the application are generally prepared according to the process illustrated in Schemes II-IV.

In some embodiments, the compounds of Formula (I) are prepared as shown in Scheme II. Therefore, ortho-iodoanilin compounds of Formula (A) are coupled with suitable unsaturated precursors such as disubstituted alkyne compound of Formula (B) in the presence of a catalyst, such as a Pd catalyst, to provide a compound of Formula (I) through known methods, for example, using the Pd catalysis procedure found in Chem. Eur. J. 2019, 25, 897-903.

Scheme II

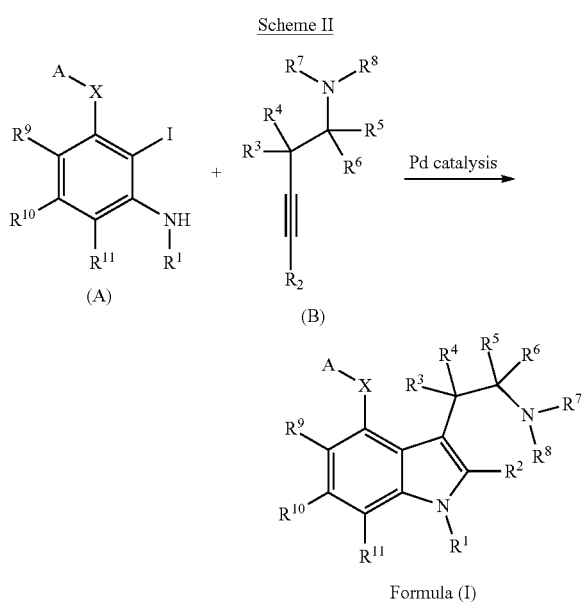

Formula (I)

In some embodiments, the compounds of Formula (I) are synthesized according to Scheme III. Therefore, a substituted indole compound of Formula (C) is coupled with a suitable amino compound of Formula (E) in the present of suitable coupling reagents such as oxalyl chloride to provide compounds of Formula (D). The compounds of Formula (D) are reduced with suitable reducing agents such as Al-based reducing agents to provide the compounds of general Formula (I).

Scheme III

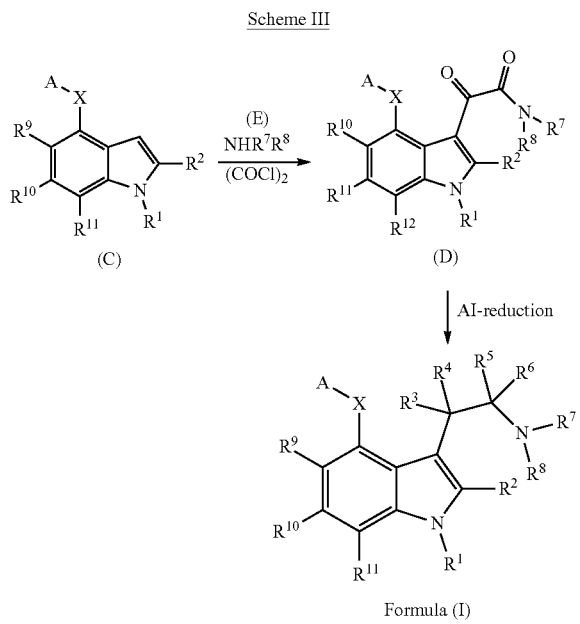

Formula (I)

A person skilled in the art would appreciate that further manipulation of the substituent groups using known chemistry can be performed on the intermediates and final compounds in the Schemes above to provide alternative compounds of the application.

Salts of compounds of the application may be formed by methods known to those of ordinary skill in the art, for example, by reacting a compound of the application with an amount of acid or base, such as an equivalent amount, in a medium such as one in which the salt precipitates or in aqueous medium followed by lyophilization.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Isotopically-enriched compounds of the application and pharmaceutically acceptable salts, solvates and/or prodrug thereof, can be prepared without undue experimentation by conventional techniques well known to those skilled in the art or by processes analogous to those described in the Schemes and Examples herein using suitable isotopically-enriched reagents and/or intermediates.

Throughout the processes described herein it is to be understood that, where appropriate, suitable protecting groups will be added to and subsequently removed from, the various reactants and intermediates in a manner that will be readily understood by one skilled in the art. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities and ways to circumvent them by carrying out appropriate transformations and synthetic steps in a suitable order, will be readily understood to one skilled in the art. Examples of transformations are given herein and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application. General Methods All starting materials used herein were commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as an internal reference, in deuterated chloroform as solvent unless otherwise indicated. All reported chemical shifts are in ppm on the delta-scale, and the fine splitting of the signals as appearing in the recordings is generally indicated, for example as s: singlet, br s: broad singlet, d: doublet, t: triplet, q: quartet, m: multiplet. Unless otherwise indicated, in the tables below, $^1$H NMR data was obtained at 400 MHz, using CDCl$_3$ as the solvent.

Purification of products was carried out using Chem Elut Extraction Columns (Varian, cat #1219-8002), Mega BE-SI (Bond Elut Silica) SPE Columns (Varian, cat #12256018; 12256026; 12256034) or by flash chromatography in silica-filled glass columns.

The following compounds were prepared using one or more of the synthetic methods outlined in Schemes I to IV.

A. Synthesis of Exemplary Compounds of the Application

Example 1: 2-(4-fluoro-1H-indol-3-yl)-N,N-bis(methyl-d$_3$)ethan-1-amine-1,1,2,2-d$_4$ (I-43)

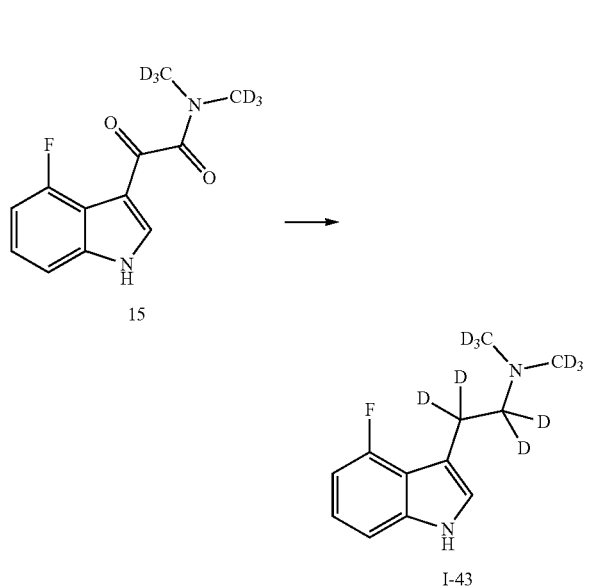

Synthesis of 2-(4-fluoro-1H-indol-3-yl)-N,N-bis(methyl-d)-2-oxoacetamide (15)

A solution of 4-fluoro-1H-indole (1.0 g, 7.39 mmol) in dry ether (20 mL) was treated with oxalyl chloride (0.63 mL, 7.39 mmol) at 0° C. The reaction was brought to room temperature and stirred for additional 16 h. The reaction was cooled to 0° C., treated with bis(methyl-d$_3$)amine hydrochloride (1.62 g, 18.49 mmol, free based with K$_2$CO$_3$ in THF) over a period of 5 min. The reaction was brought to room temperature and stirred for 4 h. The reaction was quenched with water (50 mL) and product was extracted into ethyl acetate (2×75 mL). Combined ethyl acetate layer was washed with brine (25 mL) and dried (Na$_2$SO$_4$). Solvent was evaporated and crude was purified by flash column chromatography (MeOH: CH$_2$Cl$_2$, 5:95) on silica gel to obtain the title compound 15 (0.49 g, 27.6%) as an off-white solid. $^1$H NMR (CDC$_3$): δ 10.71 (s, 1H), 7.72 (d, 1H, J=3.0 Hz), 7.15-7.10 (m, 2H), 6.94-6.87 (m, 1H); ESI-MS (m/z, %): 263 (M+Na, 100).

Synthesis of 2-(4-fluoro-1H-indol-3-yl)-N,N-bis(methyl-d$_3$)ethan-1-amine-1,1,2,2-d4 (I-43)

A suspension of Lithium aluminum deuteride (0.19 g, 1.12 mmol) in dry THF (5 mL) was treated with 2-(4-fluoro-1H-indol-3-yl)-N,N-bis(methyl-d3)-2-oxoacetamide (0.27 g, 1.33 mmol) in dry THF (10 mL) at 0° C. over a period of 10 min. The reaction was brought to room temperature, then refluxed for additional 16 hours, after work-up and column chromatography purification led to the title compound 17 (0.1 g, 42%) as a pale yellow semi-solid. $^1$H NMR (DMSO-d$_6$): δ 11.08 (s, 1H), 7.17-7.14 (m, 2H), 7.05-6.97 (m, 1H), 6.75-6.67 (m, 1H); ESI-MS (m/z, %): 217 (MH*, 100).

Example 2: 2-(4-methoxy-1H-indol-3-yl)-N,N-bis(methyl-d3)ethan-1-amine-1,1,2,2-d4 (I-44)

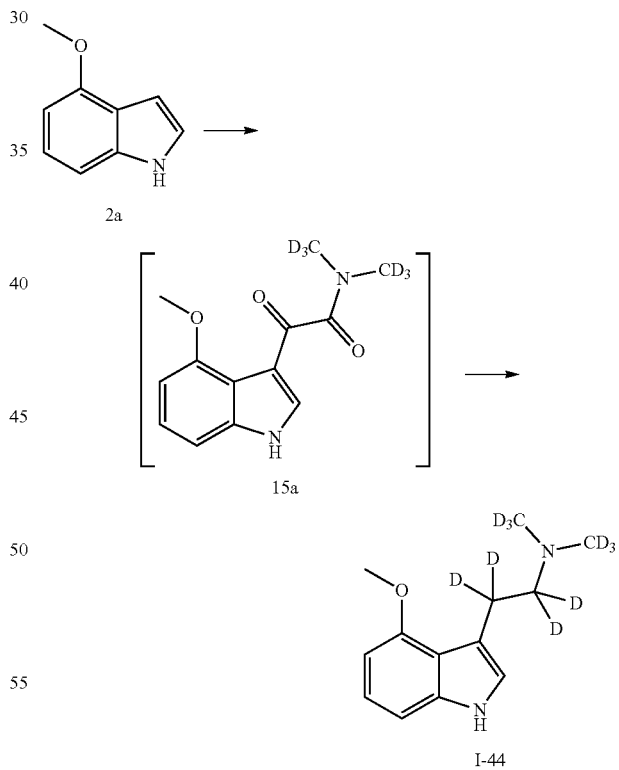

In a similar manner as described for I-43, compound 2-(4-methoxy-1H-indol-3-yl)-N,N-bis(methyl-d3)ethan-1-amine-1,1,2,2-d4 was prepared from 2 g of 4-methoxy-1H-indole through 2-(4-methoxy-1H-indol-3-yl)-N,N-bis(methyl-d3)-2-oxoacetamide reduction with Lithium aluminum deuteride to obtain the title compound (150 mg, 71%) as a light weight solid.

Example 3 and Example 4

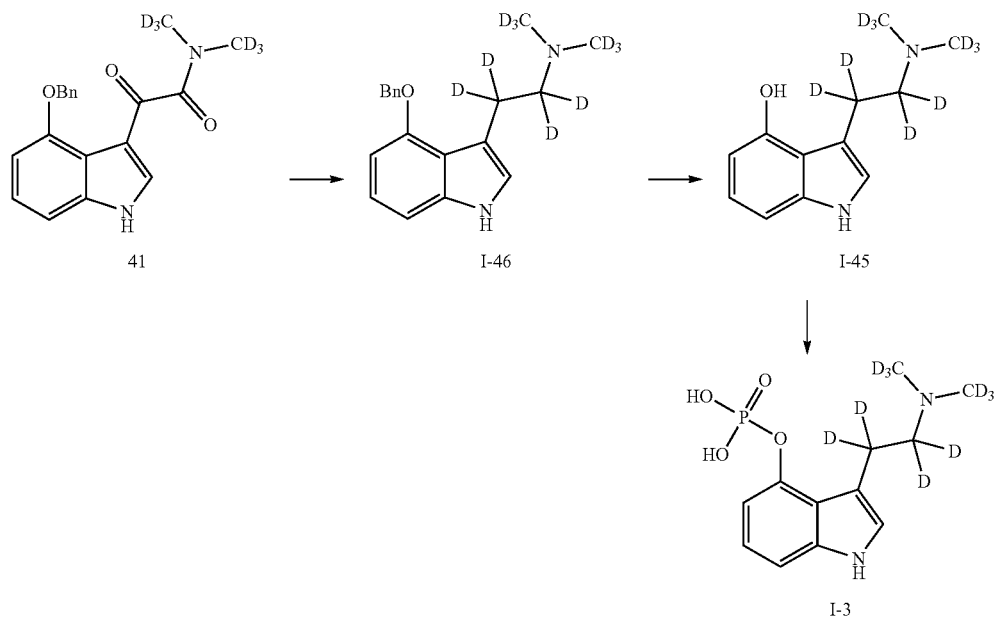

Example 3: Synthesis of 3-(2-(bis(methyl-d3)amino)ethyl-1,1,2,2-d4)-1H-indol-4-ol (I-45)

Synthesis of 2-(4-(benzyloxy)-1H-indol-3-yl)-N,N-bis(methyl-d3)ethan-1-amine-1,1,2,2-d4 (I-46)

Prepared from 2-(4-(benzyloxy)-1H-indol-3-yl)-N,N-bis(methyl-d3)-2-oxoacetamide (1.9 g, 5.78 mmol) as described for compound I-44 to obtain the title compound I-46 (0.91 g, 51.7%) as a tan solid. $^1$H NMR (CDCl$_3$): δ 8.16 (s, 1H), 7.54-7.52 (m, 2H), 7.43-7.33 (m, 2H), 7.08 (t, 1H, J=6.0 Hz), 6.98 (d, 1H, J=6.0 Hz), 6.90 (d, 1H, J=3.0 Hz), 6.57 (d, 1H, J=6.0 Hz), 5.24-5.20 (m, 2H); ESI-MS (m/z, %): 305 (MH$^+$, 100).

Synthesis of 3-(2-(bis(methyl-d3)amino)ethyl-1,1,2,2-d$_4$)-1H-indol-4-ol (I-45)

A solution of 2-(4-(benzyloxy)-1H-indol-3-yl)-N,N-bis(methyl-d3)ethan-1-amine-1,1,2,2-d$_4$ (0.88 g, 2.89 mmol)) in dry methanol (20 mL) was treated with Pd—C(0.25 g) and hydrogenated under hydrogen atm. for additional 2 h. The reaction was filtered through a pad of celite and washed with methanol (2×15 mL). Combined methanol layer was evaporated and crude was purified by flash column chromatography (2M NH$_3$ in MeOH: CH$_2$Cl$_2$, 5:95) on silica gel to obtain the title compound to obtain the title compound I-45 (0.53 g, 85.6%) as an off-white solid. $^1$H NMR of TFA salt (DMSO-d$_6$): δ 10.81 (s, 1H), 9.55 (s, 1H), 9.38 (s, 1H), 7.06 (d, 1H, J=1.5 Hz), 6.88-6.80 (m, 2H), 6.38-6.36 (m, 1H); ESI-MS (m/z, %): 215 (MH+, 100).

Example 4: Synthesis of 3-(2-(bis(methyl-d3)amino)ethyl-1,1,2,2-d4)-1H-indol-4-yl dihydrogen phosphate (I-3)

A solution of 3-(2-(bis(methyl-d$_3$)amino)ethyl-1,1,2,2-d$_4$)-1H-indol-4-ol (1.1 g, 5.13 mmol) in dry THF (20 mL) was treated with n-butyl lithium (2.36 mL, 5.90 mmol) at −78° C. The reaction was treated with tetrabenzylpyrophosphate (3.59 g, 6.67 mmol) in dry THF (20 mL) after stirring for 10 min. at same temperature. The reaction was brought to 0° C. over a period of 1 h and stirred for additional 1 h at same temperature. The reaction was treated with aminopropyl silica gel (4.4 g) and diluted with ethyl acetate (50 mL). The reaction was filtered though a pad of celite and washed with ethyl acetate (2×50 mL). Combined organic layer was evaporated and dried under vacuum to obtain crude dibenzyl (3-(2-(bis(methyl-d$_3$)amino)ethyl-1,1,2,2-d4)-1H-indol-4-yl) phosphate as light brown semi-solid.

A solution of above crude dibenzyl (3-(2-(bis(methyl-d$_3$)amino)ethyl-1,1,2,2-d4)-1H-indol-4-yl) phosphate in methanol (50 mL) was treated with Pd—C(0.5 g) and hydrogenated under hydrogen atm. for 2 h. water (15 mL) was added and hydrogenation was carried for additional 14 h. The reaction was filtered through a pad of celite and washed with methanol (2×50 mL). Solvent was evaporated, dried under high vacuum and crystallized from ethanol to obtain the title compound (1.2 g, 79%) as a light blue solid. $^1$H NMR (D20): δ 7.26-7.16 (m, 1H), 7.11-7.04 (m, 2H), 6.95 (d, 1H, J=6.0 Hz); ESI-MS (m/z, %): 295 (MH+), 306 (100), 317 (M+Na).

B. Biological Testing

Example 5: FLIPR Assay: Human 5-HT2A

I. Assessment of the activated effect of compounds of Formula I targeting on human 5-HT2A (h5-HT2A) receptor under agonist mode:
Compound Preparation and Assay Controls
I.a. Reagent and Materials:

| Regents | Vendor | Cat# |
| --- | --- | --- |
| DMEM | Gibco | 10569010 |
| FBS | Hyclone | SH30406 |
| Penicillin-Streptomycin | Invitrogen | 15140 |

-continued

| Regents | Vendor | Cat# |
|---|---|---|
| Hygromycin B | Invivogen | Ant-hg-5 |
| G418 | Invitrogen | 11811031 |
| Tetracycline hydrochloride | Abcam | ab141223 |
| DPBS | Gibco | 14190250 |
| DMSO | Millipore | 1029312500 |
| Probenecid | Sigma | P8761 |
| FLIPR Calcium 6 Assay Kit | Molecular Device | R8191 |
| HEPES | Invitrogen | 15630 |
| Hank's Buffered Saline Solution | Invitrogen | 14025 |
| Serotonin HCl | Selleck | S4244 |

I.b. Instrumentation and Consumables:

| Item | Supplier | Cat# |
|---|---|---|
| Fluorometric Imaging Plate Reader (FLIPR) | Molecular Device | Tetra |
| Countess Automated Cell Counter | Invitrogen | Countess |
| Cell Counting Chamber Slides | Invitrogen | C10312 |
| STERI-CYCLE $CO_2$ Incubator | Thermo | 371 |
| 1300 Series Class II Biological Safety Cabinet | Thermo | 1389 |
| Table-type Large Capacity Low Speed Centrifuge | Cence | L550 |
| Centrifuge | Eppendorf | 5702 |
| Echo | Labcyte | 550 |
| Echo | Labcyte | 655 |
| Electro-thermal incubator | Shanghai Yiheng | DHP-9031 |
| plate shaker | IKA | MS3 digital |
| Water Purification System | ULUPURE | UPH-III-20T |
| Versatile and Universal pH and Conductivity Meters | Mettler Toledo | S220 |
| 384-Well plate | Corning | 356663 |
| 384-Well LDV Clear microplate | LABCYTE | LP-0200 |
| 384-Well Polypropylene microplate | LABCYTE | PP-0200 |
| 384-well compound plate | Corning | 3657 |
| T25 cell culture flask | Corning | 430639 |
| 50 mL Polypropylene Centrifuge Tube | JET | CFT011500 |
| 15 mL Polypropylene Centrifuge Tube | JET | CFT011150 |

I.c. Experimental Methods and Procedures:

1. Culture the cells in cell culture medium (DMEM containing 10% FBS, 1× penicillin-streptomycin 300 µg/ml G418 and 100 µg/ml hygromycin B) at 37° C., 5% (v/v) CO2.

2. One day before the assays, detach the cell using TrypLE™ Express and count cells using cell counter. Only cells with >85% viability are used for the assay.

3. Seed 20000 cells/well in 30 µl/well culture medium to a 384-well cell plate and incubate the cells overnight at 37° C., 5% (v/v) CO2.

4. On the assay day, prepare 2×dye solution following the manual of the FLIPR@ Calcium 6 Assay Kit: i. Dilute the dye with assay buffer(20 mM HEPES in 1×HBSS, PH7.4); ii. Add probenecid to the final concentration of 5 mM; iii. Vortex vigorously for 1-2 minutes.

5. Remove medium from cell plate by flicking the cell plate on towel papers.

6. Add 10 µl of assay buffer and 10 µl of 2×dye solution to each well of the cell plate.

7. Put the cell plate on plate shaker, agitate the plate at 600 rpm for 2 minutes. Incubate the plate at 37° C. for 2 hours followed by additional 15-minute incubation at 25° C.

8. Prepare 3×compound in assay buffer: a. Dilute reference compounds to required concentration with DMSO. Add the compounds to a 384-well compound plate; b. Perform serial dilutions; c. Add 10 mM test compounds to the compound plate, perform 3-fold serial dilutions. d. Transfer 60 nl/well of compounds from source plate to a 384-well compound plate (Corning, 3657) by using an Echo; e. Add 20 µl/well assay buffer to the compound plate; f. Mix the plate on plate shaker for 2 mins;

9. Put the cell plate, compound plate and tips into FLIPR, transfer 10 µl of 3×compound to the cell plate per well with FLIPR.

II. Data Analysis i. The normalized fluorescence reading (RFU) is calculated as shown follow, while Fmax and Fmin stand for maximum and minimum of calcium signal during defined time window: RFU=Fmax−Fmin ii. Calculate the percentage activation by using following equation:

$$\% \text{ Activation} = \frac{(RFU \text{ compound} - RFU \text{ low control})}{(RFU \text{ top concentration of reference agonist} - RFU \text{ low control})} * 100\%$$

iii. Calculate $EC_{50}$ by fitting % activation against log of compound concentrations with Hill equation using XLfit.

The exemplary compounds of the application were found to be 5-HT2A agonists. The results of representative compounds are presented as $EC_{50}$ provided in Table 1. The letter "A" indicates an $EC_{50}$<1,000 nM; "B" indicates and $EC_{50}$>1,000 nM but <10,000 nM; and "C" indicates and $EC_{50}$>10,000 nM.

TABLE 1

Effect of exemplary compounds of Formula I targeting on human 5-HT2A (h5-HT2A) receptor under agonist mode:

| Compound ID#/Example | h5-HT2A EC50 [nM] |
|---|---|
| Psilocin | A |
| (I-43) Example 1 | A |
| (I-44) Example 2 | A |
| (I-45) Example 3 | A |
| (I-3) Example 4 | B |

III. Results & Discussion

Exemplary compounds of Formula I were evaluated functionally using FLIPR assay for their effect on h5-HT2A receptor under agonist mode. $EC_{50}$ (nM) concentrations are illustrated in Table 1. This assay confirms that compounds of the application are effective agonists of the target human 5-HT2A receptors.

Example 6: Human 5-HT2A: Radioligand Binding Assay

Materials and Instruments:

| Materials | Vendor | Cat# |
|---|---|---|
| Ketanserin Hydrochloride, [Ethylene-3H]- | PerkinElmer | NET791250UC |
| Ketanserin | MedChemExpress | HY-10562 |
| Bovine Serum Albumin (BSA) | Sigma | A1933 |
| Calcium chloride ($CaCl_2$) | Sigma | C5670 |

-continued

| Materials | Vendor | Cat# |
|---|---|---|
| Tris(hydroxymethyl)aminomethane (Tris) | Alfa Aesar | A18494 |
| Polyethylenimine, branched (PEI) | Sigma | 408727 |

Instrumentation and Consumables:

| Item | Supplier | Cat# |
|---|---|---|
| Microbeta[2] Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

Experiment Procedure:
i. Prepare the assay buffer following the table below; Reagent Concentration

| Reagent | Concentration |
|---|---|
| Tris | 50 mM |
| CaCl$_2$ | 4 mM |
| BSA | 0.1% (w/v) |
| Adjust pH to 7.4 followed by 0.2 µM sterile filtration | | ii. Preparation of 8 doses of reference and test compounds starting from 10 mM stock solution as requested by 5-fold serial dilutions with 100%;
iii. Prepare (v/v) DMSO: a. Add 50 µl/well of 0.5% (v/v) PEI to UniFilter-96 GF/B plates. Seal the plates and incubate at 4° C. for 3 hrs; b. After incubation, wash the plates 3 times with ice-cold wash buffer (50 mM Tris, pH7.4);
iv. Preparation of assay plates: a. Dilute cell membrane with assay buffer and add 330 µl/well to 96 round deep well plates to reach a concentration of 20 µg/well; b. Prepare 8 concentrations of reference or exemplary compounds of the application and add 110 µl/well to 96 round deep well plates; c. Dilute [3H]-ketanserin with assay buffer to 5 nM (5λ final concentration) and add 110 µl/well to 96 round deep well plates.
v. Centrifuge the plate at 1000 rpm for 30 secs and then agitate at 600 rpm, R.T. for 5 min.
vi. Seal the plates and incubate the plate at 27° C. for 90 min.
vii. Stop the incubation by vacuum filtration onto GF/B filter plates followed by 4 times washing with ice-cold wash buffer (50 mM Tris, pH7.4).
viii. Dry the plates at 37° C. for 45 min.
ix. Seal the filter plates and add 40 µl/well of scintillation cocktail.
x. Read the plate by using a Microbeta2 microplate counter.
Data Analysis:
For reference and exemplary test compounds of the application, the results are expressed as % Inhibition, using the normalization equation: N=100−100×(U−C2)/(C1−C2), where U is the unknown value, C1 is the average of high controls, and C2 is the average of low controls. The IC50 is determined by fitting percentage of inhibition as a function of compound concentrations with Hill equation using XLfit.
Results and Discussion:
The results of potential competition binding properties of the representative compounds targeting on human 5-hydroxytryptamine receptors 2A (5-HT2A) are summarized in Table 2. The results of representative compounds are presented as IC50 provided in Table XX. The symbol "#" indicates an IC50<500 nM; "# #" indicates and IC50>500 nM but<5,000 nM; and "# # #" indicates IC50>5,000 nM.

Table 2: Effect of exemplary compounds of Formula I using Radioligand binding assay on human 5-HT2A receptor.

| Compound ID#/Example | h5-HT2A IC50 [nM] |
|---|---|
| Psilocin | # |
| (I-43) Example 1 | # |
| (I-44) Example 2 | # |
| (I-45) Example 3 | # |
| (I-3) Example 4 | ## |

Exemplary compounds of Formula I were evaluated using radioligand binding assay on human 5-HT2A receptor. EC$_{50}$ (nM) concentrations are illustrated in Table 2. This assay confirms that compounds of the application are effective ligands of the target human 5-HT2A receptor.

Example 7: Human, Rat and Mouse Liver Microsomes Stability

Objective
The objective of this study was to estimate in vitro metabolic stability of I-45 in pooled human and male mouse liver microsomes. The concentrations of exemplary compounds in reaction systems were evaluated by LC-MS/MS for estimating the stability in pooled human and male mouse liver microsomes. The in vitro intrinsic clearances of test compounds were determined as well.
Protocol
A master solution in the "Incubation Plate" containing phosphate buffer, ultra-pure H$_2$O, MgCl$_2$ solution and liver microsomes was made according to Table—. The mixture was pre-warmed at 37° C. water bath for 5 minutes.

TABLE 3

Preparation of master solution

| Reagent | Stock Concentration | Volume | Final Concentration |
|---|---|---|---|
| Phosphate buffer | 200 mM | 200 µL | 100 mM |
| Ultra-pure H$_2$O | — | 106 µL | — |
| MgCl$_2$ solution | 50 mM | 40 µL | 5 mM |
| Microsomes | 20 mg/mL | 10 µL | 0.5 mg/mL |

40 µL of 10 mM NADPH solution was added to each well. The final concentration of NADPH was 1 mM. The negative control samples were prepared by replacing NADPH with 40 µL of ultra-pure H$_2$O. Samples were prepared in duplicate. Negative controls were prepared in singlet.
The reaction was started with the addition of 4 µL of 200 µM test compounds or control compounds to each master solution to get the final concentration of 2 µM. This study was performed in duplicate.

Aliquots of 50 μL were taken from the reaction solution at 0, 15, 30, 45 and 60 minutes. The reaction solutions were stopped by the addition of 4 volumes of cold methanol with IS (100 nM alprazolam, 200 nM imipramine, 200 nM labetalol and 2 μM ketoprofen). Samples were centrifuged at 3,220 g for 40 minutes. Aliquot of 90 μL of the supernatant was mixed with 90 μL of ultra-pure H2O and then was used for LC-MS/MS analysis.

LC/MS analysis was performed for all samples from this study using a Shimadzu liquid chromatograph separation system equipped with degasser DGU-20A5R; solvent delivery unit LC-30AD; system controller SIL-30AC; column oven CTO-30A; CTC Analytics HTC PAL System. Mass spectrometric analysis was performed using an Triple Quad™ 5500 instrument.

All calculations were carried out using Microsoft Excel. Peak area ratios of test compound to internal standard (listed in the below table) were determined from extracted ion chromatograms.

All calculations were carried out using Microsoft Excel. Peak areas were determined from extracted ion chromatograms. The slope value, k, was determined by linear regression of the natural logarithm of the remaining percentage of the parent drug vs. incubation time curve.

The in vitro half-life (in vitro $t_{1/2}$) was determined from the slope value:

$$\text{in vitro } t_{1/2} = -(0.693/k)$$

Conversion of the in vitro $t_{1/2}$ (min) into the in vitro intrinsic clearance (in vitro $CL_{int}$, in μL/min/mg proteins) was done using the following equation (mean of duplicate determinations):

$$\text{in vitro } CL_{int} = \left(\frac{0.693}{(t_{1/2})}\right) * \left(\frac{\text{volume of incubation }(\mu L)}{\text{amount of proteins(mg)}}\right)$$

For the exemplary compound of the application or control compound that showed an initial fast disappearance followed by a slow disappearance, only the time points that were within the initial rate were included in the calculation.

Results & Discussion

Human, rat and mouse liver microsomes contain a wide variety of drug metabolizing enzymes and are commonly used to support in vitro ADME (absorption, distribution, metabolism and excretion) studies. These microsomes are used to examine the potential first-pass metabolism by-products of orally administered drugs. Exemplary compounds of the application were evaluated for their stability in human, rat and mouse liver microsomes. A majority of the compounds of the application in three species, human, rat and mouse liver microsomes were recovered within a 60 minute time period indicating that the compounds were not rapidly cleared (see Table 4 for representative compounds of Formula I).

TABLE 4

Metabolic stability of representative example of Formula I and control compound verapamil in human, rat and mouse with NADPH

| Compound ID# | Remaining Percentage (%) after 60 min | | | $t_{1/2}$ (min) | | | $CL_{int}$ (μL/min/mg protein) | | |
|---|---|---|---|---|---|---|---|---|---|
| | Human | Rat | Mouse | Human | Rat | Mouse | Human | Rat | Mouse |
| Verapamil | 3.81 | 1.73 | 1.73 | 14.21 | 9.70 | 10.25 | 97.5 | 142.92 | 135.18 |
| Psilocin | 70.16 | 62.68 | 96.89 | 117.32 | 89.01 | 141.71 | 11.81 | 15.57 | 9.78 |
| (1-45) Example 3 | 73.65 | 3.34 | 64.91 | 135.96 | 12.23 | 96.22 | 10.19 | 113.28 | 14.40 |

Example 8: In Viva Assessment of the Pharmacokinetics in Mice and Rats

1. Formulation Preparation and Storage

| Group ID | Formulation | Storage |
|---|---|---|
| 1, 3, 5, 7 & 9 | A 0.2 mg/mL formulation of the appropriate TA will be freshly prepared in saline on the day of dosing. | −80° C. |
| 2, 4, 6, 8 & 10 | A 1 mg/mL formulation of the appropriate TA will be freshly prepared in saline on the day of dosing. | |

2. Sample Collection

| Group ID | Blood collection time (h) | Volume/ time-point |
|---|---|---|
| 1, 3, 5, 7 & 9 | 0.0833, 0.25, 0.5, 1, 2, 4, 6 & 8 | ~0.03 mL (tail snip in mouse) |
| | 24 | ~0.4 mL blood via cardiac puncture |
| 2, 4, 6, 8 & 10 | 0.25, 0.5, 1, 2, 4, 6, & 8 | ~0.03 mL (tail snip in mouse) |
| | 24 | ~0.4 mL blood via cardiac puncture |

3. Study Details

Animals:
Male C57BL/6 mice (25-30 g) and male Sprague-Dawley rats (250-325 g) from Charles River Labs were acclimatized for a minimum of 5 days prior to dosing. Body weights were recorded on the day of dosing.

Food Restriction:
Animals dosed p.o. were deprived of food overnight and fed ~2 h following dosing.

Clinical Observations:
Animals were observed at the time of dosing and each sample collection. Any abnormalities will be documented.

Dosing:
Formulations were administered intravenously (i.v.) via the tail vein or orally (p.o.) by gavage with disposable feeding needles.

Sample Collection:

Serial blood samples were collected via tail snip. Terminal blood samples were collected under isoflurane anesthesia by cardiac puncture.

Sample Processing/Storage:

All blood samples were transferred into $K_2$EDTA tubes on wet ice and centrifuged within 5 min (3200×g for 5 min at 4° C.) to obtain plasma. Plasma was stored at −80° C. until analysis.

Sample Retention:

Plasma samples were analyzed and any remaining samples were stored frozen at −80° C. until the study is completed.

4. Bioanalytical Method Development and Sample Analysis

Matrix:

Mouse or Rat Plasma, as Applicable.

Instrumentation:

AB Sciex QTRAP 4000 or 6500 MS/MS system equipped with an LC system with a binary pump, a solvent degasser, a thermostatted column compartment and a multiplate autosampler.

5. Method Development:

i. selection of the ion transition for the test compounds (i.e. identification of the parent and product ions).

ii. optimization of mass spectrometric operating parameters.

iii. establishment of the chromatographic conditions.

iv. selection of an appropriate internal standard(s) (IS).

v. sample clean-up method using protein precipitation.

6. Method Qualification:

i. the determination of the quantification dynamic range using non-zero calibration standards (STDs) in singlet. The STDs consisted of a blank matrix sample (without IS), a zero sample (with IS), and at least 6 non-zero STDs covering the expected range and including the lower level of quantitation (LLOQ).

ii. 3 injections of a system suitability sample (neat solution containing the analyte and IS) bracketing the batch.

7. Method Acceptance Criteria:

i. at least 75% of non-zero STDs were included in the calibration curve with all back-calculated concentrations within ±20% deviation from nominal concentrations (±25% for the lower level of quantification, LLOQ).

ii. the correlation coefficient (r) of the calibration curve was greater than or equal to 0.99.

iii. the area ratio variation between the pre- and post-run injections of the system suitability samples is within ±25%.

8. Sample Analysis Batch:

i. 3 injections of a system suitability sample bracketing the batch.

ii. the STDs in ascending order.

iii. the study samples and the dosing solutions diluted as 3 independent dilutions into blank matrix (plasma).

iv. for more than 40 study samples in a batch, two sets of STDs bracketing the samples were utilized.

v. samples which were 25% greater than the highest calibration standard, were diluted and re-assayed along with a corresponding dilution quality control standard. Dilution standards were acceptable if they were within 25% accuracy of the target concentration.

9. PK Analysis i. Analysis software: Phoenix® WinNonlin® 8.2 (Pharsight, Certara, Mountainview, Calif.)

ii. Analysis methods: non-compartmental analysis, linear up/log down trapezoidal rule iii. PK parameters: $C_0$, $t_{1/2}$, $AUC_{0\text{-}tlast}$, $AUC_{0\text{-}\infty}$, CL, $V_{ss}$, MRT, $t_{max(po)}$, $C_{max(po)}$, F, as appropriate 10. Results and discussion

TABLE 5

Pharmacokinetic parameters for exemplary compound 1-45 following i.v administration to male C57BL/6 mice at 1 mg/kg

| Male C57BL/6 mice (I.V. Dosing) | |
|---|---|
| Parameter | I-45 (Example 3) |
| Dose (mg/kg) | 1 |
| $C_0$ (ng/mL) | 566 ± 85.0 |
| $t_{max}$ (h) | n/a |
| $C_{max}$ (ng/mL) | n/a |
| $C_{max}$/Dose (kg*ng/mL/mg) | n/a |
| Apparent $t_{1/2}$ (h) | 5.32 ± 2.99 |
| $AUC_{0\text{-}tlast}$ (h * ng/mL) | 178 ± 32.2 |
| $AUC_{0\text{-}inf}$ (h * ng/mL) | 181 ± 30.8 |
| $AUC_{0\text{-}inf}$/Dose (h * kg * ng/mL/mg) | 181 ± 30.8 |
| CL (mL/h/kg) | 5640 ± 895 |
| $MRT_{0\text{-}inf}$(h) | 1.49 ± 0.536 |
| $V_{ss}$(mL/kg) | 8340 ± 3150 |
| $f_m$ | n/a |

TABLE 6

Pharmacokinetic parameters for exemplary compound 1-45 following p.o. administration to male C57BL/6 mice at 10 mg/kg.

| Male C57BL/6 mice (P.O. Dosing) | |
|---|---|
| Parameter | I-45 (Example 3) |
| Dose (mg/kg) | 10 |
| $t_{max}$ (h) | 0.250 ± 0.00 |
| $C_{max}$ (ng/mL) | 704 ± 128 |
| $C_{max}$/Dose (kg * ng/mL/mg) | 70.4 ± 12.8 |
| Apparent $t_{1/2}$ (h) | 4.52 ± 0.481 |
| $AUC_{0\text{-}tlast}$ (h * ng/mL) | 792 ± 120 |
| $AUC_{0\text{-}inf}$ (h * ng/mL) | 795 ± 121 |
| $AUC_{0\text{-}inf}$/Dose (h * kg * ng/mL/mg) | 79.5 ± 12.1 |
| $MRT_{0\text{-}inf}$(h) | 2.00 ± 0.227 |
| F (%) | 44.0 ± 6.70 |

$C_0$ concentration extrapolated to time zero following an i.v. dose
$t_{max}$ time at which maximum concentration is observed
$C_{max}$ maximum observed concentration
Apparent $t_{1/2}$ apparent terminal half-life
$AUC_{0\text{-}tlast}$ area under the concentration vs time curve from time 0 to the time of the last measurable concentration
$AUC_{0\text{-}inf}$ area under the concentration vs time curve from time 0 to infinity
CL systemic clearance
$MRT_{0\text{-}inf}$ mean residence time from time zero to infinity
$V_{ss}$ steady-state volume of distribution
F bioavailability = $(Dose^{iv} * AUC^{po})/(Dose^{po} * AUC^{iv}) * 100$

TABLE 7

Pharmacokinetic parameters for exemplary compound 1-45 following i.v administration to male Sprague-Dawley rats at 0.3 mg/kg Male Sprague Dawley rat (i.v. Dosing)

| Parameter | 1-45 (Example 3) |
|---|---|
| Dose (mg/kg) | 0.3 |
| $C_0$ (ng/mL) | 76.5 ± 7.49 |
| $t_{max}$ (h) | n/a |
| $C_{max}$ (ng/mL) | n/a |
| $C_{max}$/Dose (kg * ng/mL/mg) | n/a |
| Apparent $t_{1/2}$ (h) | 34.6 ± 3.17 |
| $AUC_{0-tlast}$ (h * ng/mL) | 35.2 ± 3.45 |
| $AUC_{0-inf}$ (h * ng/mL) | 117 ± 11.5 |
| $AUC_{0-inf}$/Dose (h * kg * ng/mL/mg) | 181 ± 30.8 |
| CL (mL/h/kg) | 8590 ± 874 |
| $MRT_{0-inf}$ (h) | 1.49 ± 0.536 |
| $V_{ss}$ (mL_/kg) | 0.945 ± 0.142 |
| $f_m$ | n/a |

TABLE 8

Pharmacokinetic parameters for exemplary compound 1-45 following s.c. administration to male Sprague-Dawley rats at 0.3 mg/kg

| Parameter | 1-45 (Example 3) |
|---|---|
| Dose (mg/kg) | 0.3 |
| $t_{max}$ (h) | 0.278 ± 0.210 |
| $C_{max}$ (ng/mL) | 30.2 ± 12.2 |
| $C_{max}$/Dose (kg * ng/mL/mg) | 101 ± 40.7 |
| Apparent $t_{1/2}$ (h)$^a$ | 0.647 ± 0.212 |
| $AUC_{0-tlast}$ (h * ng/mL) | 32.0 ± 9.20 |
| $AUC_{0-inf}$ (h * ng/mL) | 35.9 ± 8.71 |
| $AUC_{0-inf}$/Dose (h * kg * ng/mL/mg) | 120 ± 29.0 |
| $MRT_{0-inf}$ (h) | 0.991 ± 0.228 |
| F (%) | 125 ± 30.4 |

TABLE 9

Pharmacokinetic parameters for exemplary compound I-45 following p.o administration to male Sprague-Dawley rats at 3.0 mg/kg Male Sprague Dawley rat (p.o. Dosing)

| Parameter | 1-45 (Example 3) |
|---|---|
| Dose (mg/kg) | 10 |
| $t_{max}$ (h) | 0.333 ± 0.144 |
| $C_{max}$ (ng/mL) | 238 ± 73.3 |
| $C_{max}$/Dose (kg * ng/mL/mg) | 79.2 ± 24.4 |
| Apparent $t_{1/2}$ (h) | 2.61 ± 0.795 |
| $AUC_{0-tlast}$ (h * ng/mL) | 534 ± 38.7 |
| $AUC_{0-inf}$ (h * ng/mL) | 543 ± 43.7 |
| $AUC_{0-inf}$/Dose (h * kg * ng/mL/mg) | 181 ± 14.6 |
| $MRT_{0-inf}$ (h) | 2.77 ± 0.486 |
| F (%) | 155 ± 12.4 |

$C_0$ concentration extrapolated to time zero following an i.v. dose
$t_{max}$ time at which maximum concentration is observed
$C_{max}$ maximum observed concentration
Apparent $t_{1/2}$ apparent terminal half-life
$AUC_{0-tlast}$ area under the concentration vs time curve from time 0 to the time of the last measurable concentration
$AUC_{0-inf}$ area under the concentration vs time curve from time 0 to infinity
CL systemic clearance
$MRT_{0-inf}$ mean residence time from time zero to infinity
$V_{ss}$ steady-state volume of distribution
F bioavailability = $(Dose^{iv} * AUC^{po})/(Dose^{po} * AUC^{iv}) * 100$ Example 9: Psychedelic-Like Effects of Exemplary Compounds of Formula I The effect of different doses of exemplary compounds of Formula I were evaluated on head-twitch response (HTR) as a behavior-based model of psychedelic activity.

1. Protocols

Mouse Head Twitch

Male, C57BL/6J mice (body weight range 20-30 g) were dosed with the appropriate dose of test article, and following a 1-minute pre-treatment time, placed in individual observation chambers. Animals were visually assessed for the incidence head twitches continuously over a 1 hr period. Head twitches were defined as a rapid jerk of the head which was not elicited by an external tactile stimulus (Corne and Pickering, Psychopharmacologia, 1967, 11(1): 65-78). Each head twitch was individually counted by a trained observer, and the data expressed as the mean+SEM of 6-10 mice per group. Mice were used in a single experiment only.

Rat Behavioural Test

Male, Sprague-Dawley rats (body weight range 250-400 g) are dosed with the appropriate dose of test article and following a 1-minute pre-treatment time, placed in locomotor activity boxes (dimensions 17" W×17" L×12" H) and continuously monitored for a 1 hr period with data collected into 10 minute time bins. Animals are visually assessed for overt behavioural signs, including behaviours characteristic of 5-HT2A receptor activation (wet dog shakes, back muscle contractions), 5-HT2A receptor activation (yawning, penile grooming) and 5-HT1A behaviours (forepaw treading, hindlimb abduction) (Halberzettl et al, Behav Brain Res. 256: 328-345, 2013). Additional behavioural and somatic signs characteristic of 5-HT syndrome (e.g. tremor, salivation, flat body posture, core body temperature change) are also measured. Simultaneously, the spontaneous activity of the rats is measured using an automated tracking system (Med Associates, VT, USA). Activity data collected includes total distance traveled, rearing counts and ambulatory episodes. All data are expressed as the mean+SEM of 6-10 rats per group.

Drug Discrimination in the Rat

Male Sprague-Dawley rats are initially food restricted by presentation of 18-20 g food at day end (single housing). After 7 days acclimatisation to the food restriction procedure, they are trained daily to lever press for food (45 mg Bioserve pellet) in standard 2-lever operant conditioning chambers controlled by Med-PC software over a period of 1 week (Med. Associates Ins., St. Albans, Vt.). The rats are trained to lever press for food to an FR10 value (i.e 10 lever presses for a single food reward). Once stable food responding is acquired to both response levers, discrimination training began. Over a period of 20-50 training sessions, the rats are trained to associate one lever to a psilocybin training dose of 1 mg/kg SC, and the second lever to a neutral stimulus (saline, SC) (Winter et al, Pharmacol Biochem Behav. 87(4): 472-480, 2007). Training sessions last 30-min or until the delivery of 50 pellets and continue until the animals attain appropriate stimulus control (defined as six consecutive sessions where animals make no more than 16 lever presses before the delivery of the first reward, and at least 95% total responses on the appropriate lever). The rats continue to receive daily food ration in their home cage at day end.

Once trained, tests of substitution are conducted. On test days, both levers are designated active, i.e., every 10th response on either lever results in delivery of a food pellet.

Test sessions continue until 50 pellets have been obtained or 30 min has elapsed. During these sessions response rate is also measured.

Results and Discussion

Exemplary compound I-45: Dose response (0.3-10 mg/kg SC) vs 5-HT2A signs of mouse head twitch measured over 1 h (Table 9; FIG. 1). Also, locomotor activity and other 5-HT receptor signs were measured. Mice showed a dose dependent increase in head twitch frequency compared to vehicle control, which is consistent with 5HT2A activation and associated with the hallucinogenic response in humans.

TABLE 9

Dose response versus mouse head twitch measured over 1 h

| Animal ID | Treatment (mg/kg) | Body Weight (g) | Head Twitch 10 mins | 20 mins | 30 mins | 40 mins | 50 mins | 60 mins | Total |
|---|---|---|---|---|---|---|---|---|---|
| O1 | Vehicle | 25.1 | 0 | 1 | 0 | 0 | 0 | 0 | 1 |
| O2 | | 29.5 | 0 | 0 | 0 | 0 | 0 | 0 | 0 |
| O3 | | 21.5 | 0 | 0 | 0 | 0 | 0 | 0 | 0 |
| O4 | | 19.3 | 1 | 0 | 0 | 0 | 0 | 0 | 1 |
| O5 | | 20.3 | 0 | 0 | 0 | 0 | 0 | 0 | 0 |
| O6 | | 19.7 | 0 | 0 | 0 | 0 | 0 | 0 | 0 |
| AVG | | 22.6 | 0.2 | 0.2 | 0.0 | 0.0 | 0.0 | 0.0 | 0.3 |
| SEM | | 1.6 | 0.2 | 0.2 | 0.0 | 0.0 | 0.0 | 0.0 | 0.2 |
| C1 | I-45 | 23.2 | 0 | 0 | 0 | 0 | 0 | 0 | 0 |
| C2 | (0.03 mg/kg) | 24.4 | 1 | 0 | 0 | 0 | 0 | 0 | 1 |
| C3 | | 25.0 | 3 | 0 | 0 | 0 | 1 | 0 | 4 |
| C4 | | 24.4 | 2 | 0 | 0 | 0 | 0 | 0 | 2 |
| C5 | | 23.3 | 2 | 0 | 0 | 0 | 0 | 0 | 2 |
| C6 | | 25.1 | 0 | 1 | 0 | 0 | 0 | 0 | 1 |
| AVG | | 24.2 | 1.3 | 0.2 | 0.0 | 0.0 | 0.2 | 0.0 | 1.7 |
| SEM | | 0.3 | 0.5 | 0.2 | 0.0 | 0.0 | 0.2 | 0.0 | 0.6 |
| P1 | I-45 | 26.3 | 3 | 1 | 0 | 1 | 0 | 0 | 5 |
| P2 | (0.1 mg/kg) | 28.6 | 6 | 0 | 1 | 0 | 2 | 0 | 9 |
| P3 | | 25.5 | 0 | 2 | 1 | 0 | 0 | 0 | 3 |
| P4 | | 28.7 | 1 | 0 | 0 | 1 | 0 | 0 | 2 |
| P5 | | 27.7 | 0 | 0 | 0 | 0 | 1 | 0 | 1 |
| P6 | | 28.5 | 2 | 1 | 1 | 0 | 0 | 0 | 4 |
| P7 | | 25.1 | 1 | 1 | 0 | 0 | 0 | 0 | 2 |
| P8 | | 21.8 | 0 | 2 | 0 | 0 | 0 | 0 | 2 |
| P9 | | 25.2 | 1 | 1 | 1 | 0 | 0 | 0 | 3 |
| P10 | | 24.3 | 2 | 0 | 0 | 0 | 1 | 0 | 3 |
| AVG | | 26.2 | 1.6 | 0.8 | 0.4 | 0.2 | 0.4 | 0.0 | 3.4 |
| SEM | | 0.7 | 0.6 | 0.2 | 0.2 | 0.1 | 0.2 | 0.0 | 0.7 |
| Q1 | I-45 | 26.0 | 3 | 0 | 1 | 0 | 0 | 0 | 4 |
| Q2 | (0.3 mg/kg) | 27.6 | 1 | 1 | 0 | 0 | 0 | 0 | 2 |
| Q3 | | 26.1 | 0 | 0 | 1 | 0 | 0 | 0 | 1 |
| Q4 | | 27.7 | 1 | 1 | 0 | 0 | 0 | 0 | 2 |
| Q5 | | 26.9 | 2 | 1 | 0 | 1 | 0 | 0 | 4 |
| Q6 | | 28.9 | 2 | 1 | 0 | 0 | 0 | 0 | 3 |
| Q7 | | 22.5 | 1 | 1 | 3 | 0 | 1 | 0 | 6 |
| Q8 | | 23.6 | 2 | 1 | 1 | 0 | 0 | 0 | 4 |
| Q9 | | 24.7 | 0 | 0 | 0 | 0 | 0 | 0 | 0 |
| Q10 | | 25.1 | 1 | 0 | 0 | 2 | 1 | 0 | 4 |
| AVG | | 25.9 | 1.3 | 0.6 | 0.6 | 0.3 | 0.2 | 0.0 | 3.0 |
| SEM | | 0.6 | 0.3 | 0.2 | 0.3 | 0.2 | 0.1 | 0.0 | 0.6 |
| R1 | I-45 | 27.1 | 0 | 0 | 1 | 0 | 0 | 0 | 1 |
| R2 | (1 mg/kg) | 27.2 | 4 | 2 | 0 | 0 | 0 | 0 | 6 |
| R3 | | 29.9 | 1 | 1 | 0 | 0 | 0 | 0 | 2 |
| R4 | | 26.1 | 3 | 0 | 0 | 0 | 0 | 0 | 3 |
| R5 | | 30.6 | 3 | 7 | 3 | 2 | 0 | 0 | 15 |
| R6 | | 27.1 | 3 | 8 | 1 | 2 | 0 | 0 | 14 |
| AVG | | 28.0 | 2.3 | 3.0 | 0.8 | 0.7 | 0.0 | 0.0 | 6.8 |
| SEM | | 0.7 | 0.6 | 1.5 | 0.5 | 0.4 | 0.0 | 0.0 | 2.5 |
| S1 | I-45 | 26.1 | 1 | 2 | 2 | 2 | 1 | 0 | 8 |
| S2 | (3 mg/kg) | 25.3 | 3 | 1 | 1 | 0 | 0 | 0 | 5 |
| S3 | | 27.0 | 1 | 2 | 0 | 0 | 0 | 0 | 3 |
| S4 | | 25.5 | 2 | 0 | 1 | 0 | 1 | 0 | 4 |
| S5 | | 26.8 | 6 | 3 | 2 | 3 | 0 | 0 | 14 |
| S6 | | 27.2 | 0 | 5 | 1 | 0 | 0 | 1 | 7 |
| AVG | | 26.3 | 2.2 | 2.2 | 1.2 | 0.8 | 0.3 | 0.2 | 6.8 |
| SEM | | 0.3 | 0.9 | 0.7 | 0.3 | 0.5 | 0.2 | 0.2 | 1.6 |
| T1 | I-45 | 28.5 | 3 | 1 | 0 | 0 | 0 | 0 | 4 |
| T2 | (10 mg/kg) | 30.0 | 1 | 0 | 0 | 1 | 0 | 0 | 2 |
| T3 | | 28.3 | 1 | 0 | 0 | 1 | 0 | 3 | 5 |
| T4 | | 29.3 | 0 | 0 | 0 | 0 | 0 | 0 | 0 |
| T5 | | 26.0 | 0 | 1 | 0 | 0 | 0 | 0 | 1 |
| T6 | | 30.0 | 0 | 0 | 0 | 0 | 0 | 0 | 0 |
| AVG | | 28.7 | 0.8 | 0.3 | 0.0 | 0.3 | 0.0 | 0.5 | 2.0 |
| SEM | | 0.6 | 0.5 | 0.2 | 0.0 | 0.2 | 0.0 | 0.5 | 0.9 |

While the present application has been described with reference to examples, it is to be understood that the scope of the claims should not be limited by the embodiments set forth in the examples, but should be given the broadest interpretation consistent with the description as a whole.

All patents, patent applications and publications cited herein are hereby incorporated by reference in their entirety. The disclosures of these publications in their entireties are hereby incorporated by reference into this application in order to more fully describe the state of the date of the application described and claimed herein.

The invention claimed is:

1. A compound of Formula I-2 or a pharmaceutically acceptable salt, solvate or prodrug thereof:

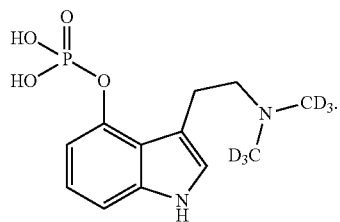

(I-2)

2. A compound of Formula I-2, or a pharmaceutically acceptable salt or solvate thereof:

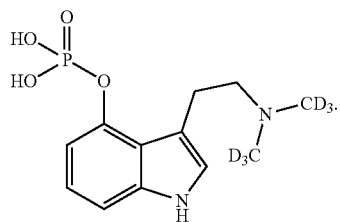

(I-2)

3. A composition comprising the compound of claim 1, or a pharmaceutically acceptable salt, solvate or prodrug thereof.

4. A composition comprising the compound of claim 2, or a pharmaceutically acceptable salt or solvate thereof.

5. A pharmaceutical composition comprising the compound of claim 1, or a pharmaceutically acceptable salt or solvate.

6. The composition of claim 5, wherein the composition further comprises a pharmaceutically acceptable carrier.

7. The composition of claim 6, wherein the composition is suitable for oral administration.

8. The composition of claim 6, wherein the composition is suitable for intravenous (IV) administration.

9. The composition of claim 7, wherein the composition is a tablet, buccal tablet, troch, capsule, caplet, pellet, granule, lozenge, chewing gum, powder, syrup, elixir, wafer, aqueous solution or suspension.

10. The composition of claim 5, wherein the composition comprises 0.1 mg to 1000 mg of the compound of Formula I-2, or a pharmaceutically acceptable salt or solvate thereof.

11. The composition of claim 5, wherein the composition comprises 500 mg of the compound of Formula I-2, or a pharmaceutically acceptable salt or solvate thereof.

12. The composition of claim 5, wherein the composition comprises 10 mg to 250 mg of the compound of Formula I-2, or a pharmaceutically acceptable salt or solvate thereof.

13. The composition of claim 5, wherein the composition comprises 0.5 mg to 250 mg of the compound of Formula I-2, or a pharmaceutically acceptable salt or solvate thereof.

14. The composition of claim 5, wherein the composition comprises 0.5 mg to 50 mg of the compound of Formula I-2, or a pharmaceutically acceptable salt or solvate thereof.

15. The composition of claim 5, wherein the composition comprises 10 mg to 50 mg of the compound of Formula I-2, or a pharmaceutically acceptable salt or solvate thereof.

16. The composition of claim 5, comprising the compound of Formula I-2, or a pharmaceutically acceptable salt thereof.

17. A method for activating a serotonin receptor in a subject comprising administering the compound of claim 1, or a pharmaceutically acceptable salt, solvate or prodrug thereof, to the subject.

18. A method of treating a subject having a condition that is treated by activation of a serotonin receptor, comprising administering the compound of claim 1, or a pharmaceutically acceptable salt solvate or prodrug thereof.

19. The method of claim 18, wherein the condition is a neurological or psychiatric disorder.

20. The method of claim 18, wherein the condition is psychosis or psychotic symptoms.

21. The method of claim 18, wherein the condition is a mental illness disorder.

22. The method of claim 21, wherein the mental illness disorder is selected from generalized anxiety disorders, phobias, depression, mood disorders, psychotic disorders, eating disorders, impulse control disorders, addiction disorders, personality disorders, dissociative disorders, factitious disorders, sexual disorders, gender disorders, somatic symptom disorders, attentional disorders, tic disorders, sleep-related disorders, and a combination thereof.

23. The method of claim 21, wherein the mental illness disorder is selected from panic disorder, social anxiety disorder, hopelessness, loss of pleasure, fatigue, suicidal thoughts, bipolar disorder, cancer-related depression, anxiety, cyclothymic disorder, hallucinations, delusions, schizophrenia, anorexia nervosa, bulimia nervosa, binge eating disorder, pyromania, kleptomania, compulsive gambling, alcohol addiction; drug addiction, antisocial personality disorder, obsessive-compulsive personality disorder, paranoid personality disorder; obsessive-compulsive disorder (OCD), post-traumatic stress disorder (PTSD), stress response syndromes, sexual dysfunction, gender identity disorder, paraphilia, attentional deficit disorder, attentional deficit hyperactivity disorder, Tourette's syndrome, and a combination thereof.

24. The method of claim 21, wherein the mental illness disorder is selected from hallucinations, delusions, and a combination thereof.

25. The method of claim 24, wherein the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and a combination thereof.

26. The method of claim 21, wherein the mental illness disorder comprises cognitive impairment, ischemia, neurodegeneration, refractory substance use disorders, sleep disorders, pain, obesity, eating disorders, seizure disorders, neuronal cell death, excitotoxic call death, or a combination thereof.

27. The method of claim 18, wherein the condition is a CNS disorder that is a form of dementia.

28. The method of claim 18, comprising administering the compound of Formula I-2, or a pharmaceutically acceptable salt or solvate thereof.

29. The method of claim 18, wherein the subject is a feline or canine and the condition is anxiety, fear, stress, sleep disturbances, cognitive dysfunction, aggression, or a combination thereof.

* * * * *

UNITED STATES PATENT AND TRADEMARK OFFICE
CERTIFICATE OF CORRECTION

PATENT NO. : 11,597,738 B2
APPLICATION NO. : 17/743718
DATED : March 7, 2023
INVENTOR(S) : Abdelmalik Slassi et al.

It is certified that error appears in the above-identified patent and that said Letters Patent is hereby corrected as shown below:

In the Claims

At Claim 26, Column 97, Line 2, "call" should read -- cell --.

Signed and Sealed this
Thirtieth Day of January, 2024

Katherine Kelly Vidal
*Director of the United States Patent and Trademark Office*